US010603018B2

(12) United States Patent
Wilson et al.

(10) Patent No.: US 10,603,018 B2
(45) Date of Patent: Mar. 31, 2020

(54) INTRAVASCULAR DEVICES, SYSTEMS, AND METHODS FOR THE CONTROLLED DISSECTION OF BODY LUMENS

(71) Applicant: INTERVENE, INC., Mountain View, CA (US)

(72) Inventors: Fletcher T. Wilson, San Francisco, CA (US); Michi Garrison, Half Moon Bay, CA (US); David Batten, Los Gatos, CA (US); Benjamin J. Clark, Redwood City, CA (US); Luke Clauson, Redwood City, CA (US); David Lari, San Francisco, CA (US)

(73) Assignee: InterVene, Inc., South San Francisco, CA (US)

( * ) Notice: Subject to any disclaimer, the term of this patent is extended or adjusted under 35 U.S.C. 154(b) by 505 days.

(21) Appl. No.: 14/972,006

(22) Filed: Dec. 16, 2015

(65) Prior Publication Data

US 2016/0166243 A1 Jun. 16, 2016

Related U.S. Application Data

(60) Provisional application No. 62/092,809, filed on Dec. 16, 2014.

(51) Int. Cl.
*A61B 17/32* (2006.01)
*A61B 17/00* (2006.01)
(Continued)

(52) U.S. Cl.
CPC .... *A61B 17/00234* (2013.01); *A61B 17/3209* (2013.01); *A61B 17/320016* (2013.01);
(Continued)

(58) Field of Classification Search
CPC ............... A61B 17/32; A61B 17/3207; A61B 17/320725; A61B 17/320016;
(Continued)

(56) References Cited

U.S. PATENT DOCUMENTS 3,704,711 A 12/1972 Park
4,898,574 A 2/1990 Uchiyama et al.
(Continued)

FOREIGN PATENT DOCUMENTS

CA 1281381 C 3/1991
CA 2678971 A1 8/2008
(Continued)

OTHER PUBLICATIONS

Corcos, I., "A new autologous venous valve by intimal flap: One cases report." Note Di Tecnica, Minerva Cardioangiol, 2003, 51, 10 pages.
(Continued)

*Primary Examiner* — Melanie R Tyson
(74) *Attorney, Agent, or Firm* — Perkins Coie LLP

(57) ABSTRACT

Devices, systems, and methods for treating damaged or diseased valves are disclosed. A representative embodiment includes an elongated shaft having a longitudinal axis, a proximal portion, and a distal portion, and a dissection arm at the distal portion. The dissection arm can have a longitudinal axis and be moveable between a low-profile state and a deployed state. In the deployed state, a portion of the arm can flex outwardly away from the longitudinal axis of the shaft. The arm is configured to be deployed within a space within a vessel wall such that, as the arm moves from the low-profile state to the deployed state, the arm pushes against vessel wall tissue at a periphery of the space, thereby separating tissue at the periphery to form a dissection pocket having a predetermined shape.

18 Claims, 35 Drawing Sheets

(51) Int. Cl.
*A61B 17/3209* (2006.01)
*A61B 17/3207* (2006.01)
*A61F 2/24* (2006.01)

(52) U.S. Cl.
CPC ... *A61B 17/3207* (2013.01); *A61B 17/320725* (2013.01); *A61B 2017/00292* (2013.01); *A61B 2017/00778* (2013.01); *A61B 2017/00783* (2013.01); *A61B 2017/320044* (2013.01); *A61B 2017/320056* (2013.01); *A61F 2/2475* (2013.01)

(58) Field of Classification Search
CPC ...... A61B 17/3209; A61B 2017/32096; A61B 17/00234; A61B 2017/00292; A61B 2017/00778; A61B 2017/00783; A61B 2017/320044; A61B 2017/320056; A61B 2017/22071; A61B 2017/22095; A61B 2017/22044; A61M 25/0194; A61M 2025/0197
USPC .................................................. 606/167, 170
See application file for complete search history.

(56) References Cited

U.S. PATENT DOCUMENTS

| | | | |
|---|---|---|---|
| 4,932,962 A | 6/1990 | Yoon et al. | |
| 5,112,339 A | 5/1992 | Zelman et al. | |
| 5,190,046 A | 3/1993 | Shturman et al. | |
| 5,372,601 A | 12/1994 | Lary et al. | |
| 5,443,443 A | 8/1995 | Shiber et al. | |
| 5,464,395 A | 11/1995 | Faxon et al. | |
| 5,601,588 A | 2/1997 | Tonomura et al. | |
| 5,606,975 A | 3/1997 | Liang et al. | |
| 5,695,507 A | 12/1997 | Auth | |
| 5,738,901 A | 4/1998 | Wang et al. | |
| 5,795,322 A | 8/1998 | Boudewijn | |
| 5,810,847 A | 9/1998 | Laufer et al. | |
| 5,836,945 A | 11/1998 | Perkins | |
| 5,989,276 A | 11/1999 | Houser et al. | |
| 6,190,353 B1 | 2/2001 | Makower et al. | |
| 6,379,319 B1 | 4/2002 | Garibotto et al. | |
| 6,475,226 B1 | 11/2002 | Farrell et al. | |
| 6,506,178 B1 | 1/2003 | Schubart et al. | |
| 6,514,217 B1 | 2/2003 | Selmon et al. | |
| 6,676,665 B2 | 1/2004 | Foley et al. | |
| 6,685,648 B2 | 2/2004 | MacAulay et al. | |
| 6,692,466 B1 | 2/2004 | Chow et al. | |
| 6,702,744 B2 | 3/2004 | Mandrusov et al. | |
| 6,758,836 B2 | 7/2004 | Zawacki et al. | |
| 6,902,576 B2 | 6/2005 | Drasler et al. | |
| 7,008,411 B1 | 3/2006 | Mandrusov et al. | |
| 7,056,325 B1 | 6/2006 | Makower et al. | |
| 7,150,738 B2 | 12/2006 | Ray et al. | |
| 7,179,249 B2 | 2/2007 | Steward et al. | |
| 7,273,469 B1 | 9/2007 | Chan et al. | |
| 7,357,795 B2 | 4/2008 | Kaji et al. | |
| 7,517,352 B2 | 4/2009 | Evans et al. | |
| 7,775,968 B2 | 8/2010 | Mathis | |
| 7,780,592 B2 | 8/2010 | Tronnes et al. | |
| 7,918,870 B2 | 4/2011 | Kugler et al. | |
| 7,927,305 B2 | 4/2011 | Yribarren et al. | |
| 7,938,819 B2 | 5/2011 | Atkinson et al. | |
| 7,955,346 B2 | 6/2011 | Mauch et al. | |
| 8,025,655 B2 | 9/2011 | Atkinson et al. | |
| 8,083,727 B2 | 12/2011 | Kugler et al. | |
| 8,100,860 B2 | 1/2012 | von Oepen et al. | |
| 8,114,123 B2 | 2/2012 | Brenzel et al. | |
| 8,267,947 B2 | 9/2012 | Ellingwood et al. | |
| 8,323,261 B2 | 12/2012 | Atkinson et al. | |
| 8,460,316 B2 | 6/2013 | Wilson et al. | |
| 8,636,712 B2 | 1/2014 | Atkinson et al. | |
| 9,320,504 B2 | 4/2016 | Wilson et al. | |
| 9,545,289 B2 | 1/2017 | Yu et al. | |
| 2001/0041899 A1 | 11/2001 | Foster | |
| 2002/0029052 A1 | 3/2002 | Evans et al. | |
| 2002/0072706 A1 | 6/2002 | Hiblar et al. | |
| 2002/0091362 A1 | 7/2002 | Maginot et al. | |
| 2002/0103459 A1 | 8/2002 | Sparks et al. | |
| 2004/0167558 A1 | 8/2004 | Igo et al. | |
| 2004/0215339 A1 | 10/2004 | Drasler et al. | |
| 2005/0014995 A1 | 1/2005 | Amundson et al. | |
| 2005/0075665 A1 | 4/2005 | Brenzel et al. | |
| 2005/0165466 A1 | 7/2005 | Morris et al. | |
| 2005/0273159 A1 | 12/2005 | Opie et al. | |
| 2006/0094929 A1 | 5/2006 | Tronnes et al. | |
| 2006/0136045 A1 | 6/2006 | Flagle et al. | |
| 2006/0178646 A1 | 8/2006 | Harris et al. | |
| 2006/0184187 A1 | 8/2006 | Surti | |
| 2006/0235449 A1 | 10/2006 | Schubart et al. | |
| 2006/0271090 A1 | 11/2006 | Shaked et al. | |
| 2007/0005093 A1* | 1/2007 | Cox | A61B 17/32001 606/198 |
| 2007/0093780 A1 | 4/2007 | Kugler et al. | |
| 2007/0093781 A1 | 4/2007 | Kugler et al. | |
| 2007/0208368 A1 | 9/2007 | Katoh et al. | |
| 2008/0033467 A1 | 2/2008 | Miyamoto et al. | |
| 2008/0103480 A1 | 5/2008 | Bosel et al. | |
| 2008/0228171 A1 | 9/2008 | Kugler et al. | |
| 2008/0243065 A1 | 10/2008 | Rottenberg et al. | |
| 2009/0005793 A1 | 1/2009 | Pantages et al. | |
| 2009/0112059 A1 | 4/2009 | Nobis et al. | |
| 2009/0182192 A1 | 7/2009 | Shiono et al. | |
| 2009/0209910 A1 | 8/2009 | Kugler et al. | |
| 2009/0254051 A1 | 10/2009 | von Oepen et al. | |
| 2010/0076476 A1* | 3/2010 | To | A61B 17/1617 606/170 |
| 2010/0152682 A1 | 6/2010 | Mauch et al. | |
| 2010/0152843 A1 | 6/2010 | Mauch et al. | |
| 2010/0256599 A1 | 10/2010 | Kassab et al. | |
| 2011/0264125 A1 | 10/2011 | Wilson et al. | |
| 2011/0264127 A1 | 10/2011 | Mauch et al. | |
| 2011/0264128 A1 | 10/2011 | Mauch et al. | |
| 2012/0143234 A1 | 6/2012 | Wilson et al. | |
| 2012/0289987 A1 | 11/2012 | Wilson et al. | |
| 2013/0066346 A1 | 3/2013 | Pigott et al. | |
| 2013/0103070 A1 | 4/2013 | Kugler et al. | |
| 2013/0116715 A1* | 5/2013 | Weber | A61B 17/32072 606/159 |
| 2013/0216114 A1 | 8/2013 | Courtney et al. | |
| 2013/0317534 A1 | 11/2013 | Zhou et al. | |
| 2014/0012301 A1 | 1/2014 | Wilson et al. | |
| 2015/0057566 A1 | 2/2015 | Vetter et al. | |
| 2015/0094532 A1 | 4/2015 | Wilson et al. | |
| 2015/0265263 A1 | 9/2015 | Wilson et al. | |
| 2015/0342631 A1 | 12/2015 | Wilson et al. | |
| 2015/0359630 A1 | 12/2015 | Wilson et al. | |
| 2016/0166243 A1 | 6/2016 | Wilson et al. | |
| 2016/0235428 A1 | 8/2016 | Wilson et al. | |
| 2017/0035450 A1 | 2/2017 | Fletcher et al. | |
| 2017/0035455 A1 | 2/2017 | Fletcher et al. | |
| 2018/0000509 A1 | 1/2018 | Wilson et al. | |
| 2018/0214173 A1 | 8/2018 | Wilson et al. | |
| 2018/0289441 A1 | 10/2018 | Wilson et al. | |
| 2018/0333166 A1 | 11/2018 | Wilson et al. | |

FOREIGN PATENT DOCUMENTS

| | | |
|---|---|---|
| CN | 1907243 A | 2/2007 |
| CN | 1957861 A | 5/2007 |
| JP | 2002514111 A | 5/2002 |
| JP | 2003033357 A | 2/2003 |
| JP | 2003267160 A | 9/2003 |
| JP | 2009165822 A | 7/2009 |
| JP | 2009183516 A | 8/2009 |
| RU | 2108751 C1 | 4/1998 |
| RU | 2160057 C2 | 12/2000 |
| WO | 99000059 A1 | 1/1999 |
| WO | 2008063621 A2 | 5/2008 |
| WO | 2010074853 A1 | 7/2010 |
| WO | 2009133634 A1 | 8/2011 |
| WO | 2011106735 A1 | 9/2011 |

(56) References Cited

FOREIGN PATENT DOCUMENTS

| WO | 2012145444 A2 | 10/2012 |
| WO | 2013119849 A1 | 8/2013 |
| WO | 2014110460 A1 | 7/2014 |

OTHER PUBLICATIONS

Lugli et al., Neovalve construction in the deep venous incompetence. J. Vasc. Surg., Jan. 2009, 49(1), 156-62.
Maleti, O., Neovalve construction in postthrombotic syndrome. Journal of Vascular Surgery, vol. 34, No. 4, 6 pages.
International Search Report and Written Opinion dated Jun. 15, 2016, International Application No. PCT/US2015/066205, 18 pages.
JP Patent Application No. 2017-533328, Foreign Office Action with English Translation dated Sep. 2, 2019, 13 pages.
EP Patent Application No. 15817748.5, Foreign Office Action dated Sep. 10, 2019, 6 pages.

* cited by examiner

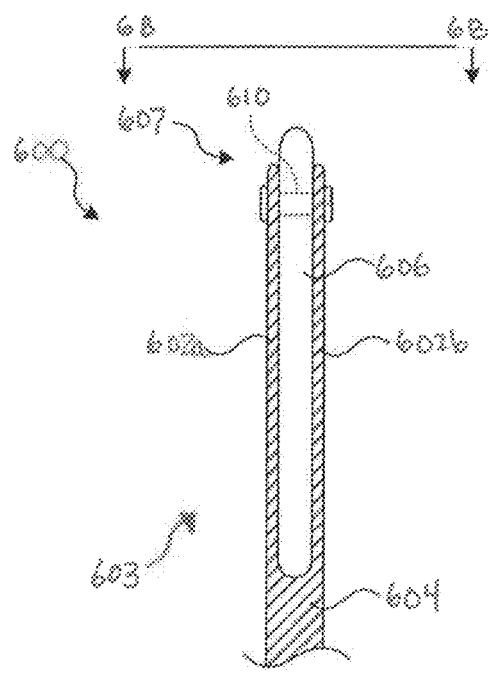
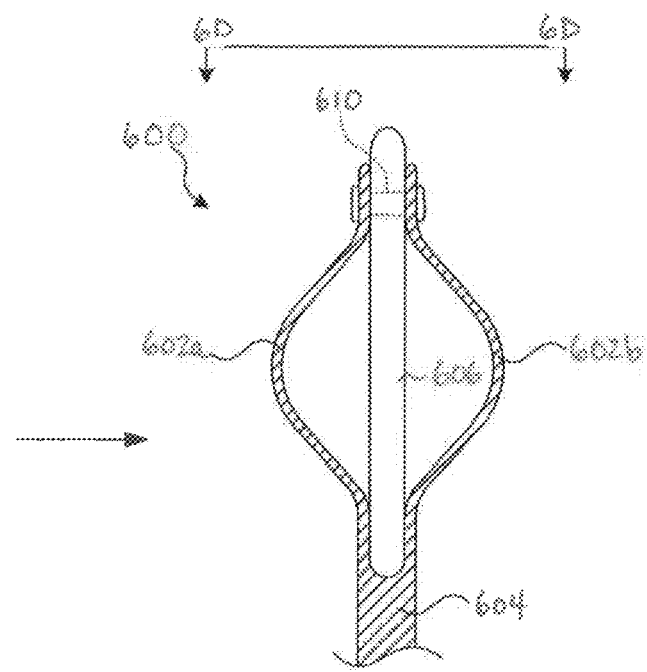
FIG. 6A
FIG. 6C
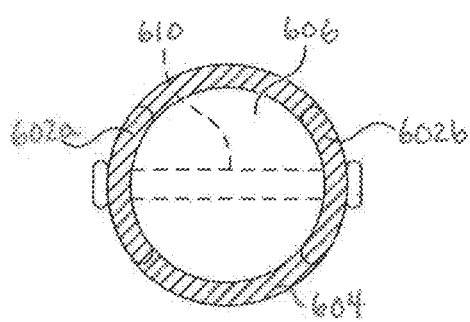
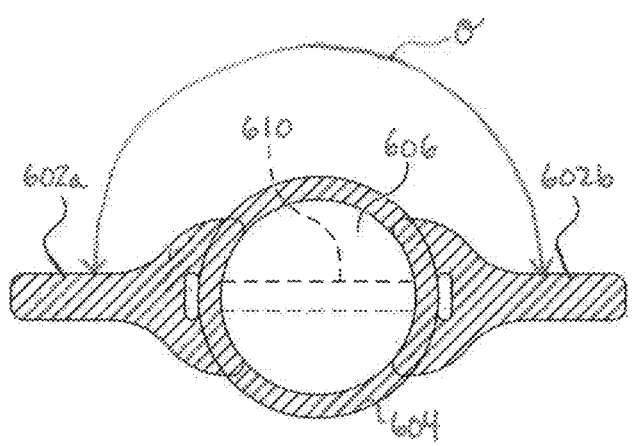
FIG. 6B
FIG. 6D

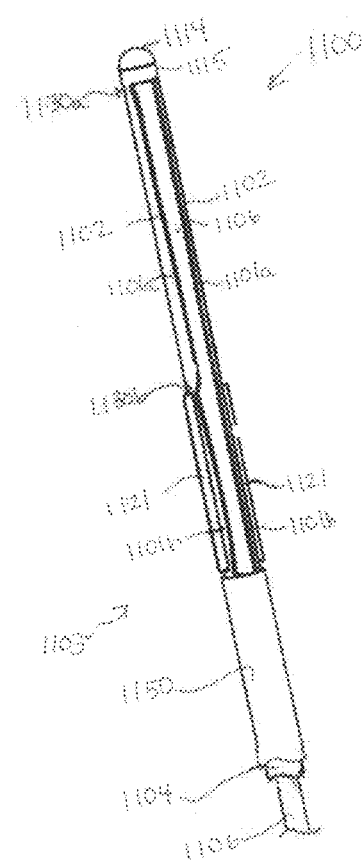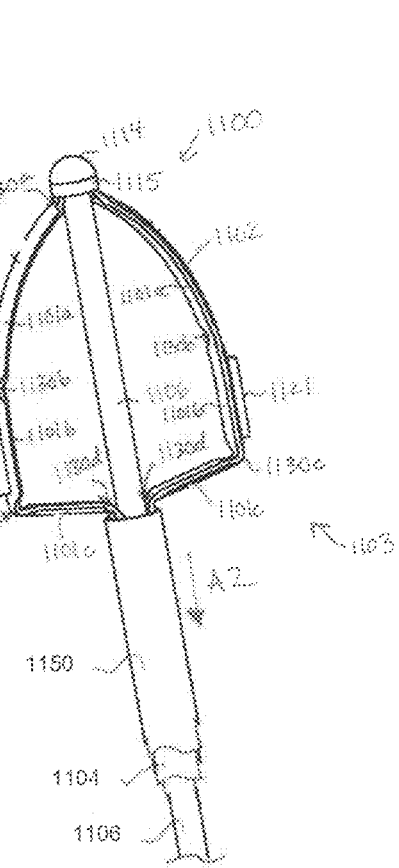
FIG. 11A  FIG. 11B  FIG. 11C

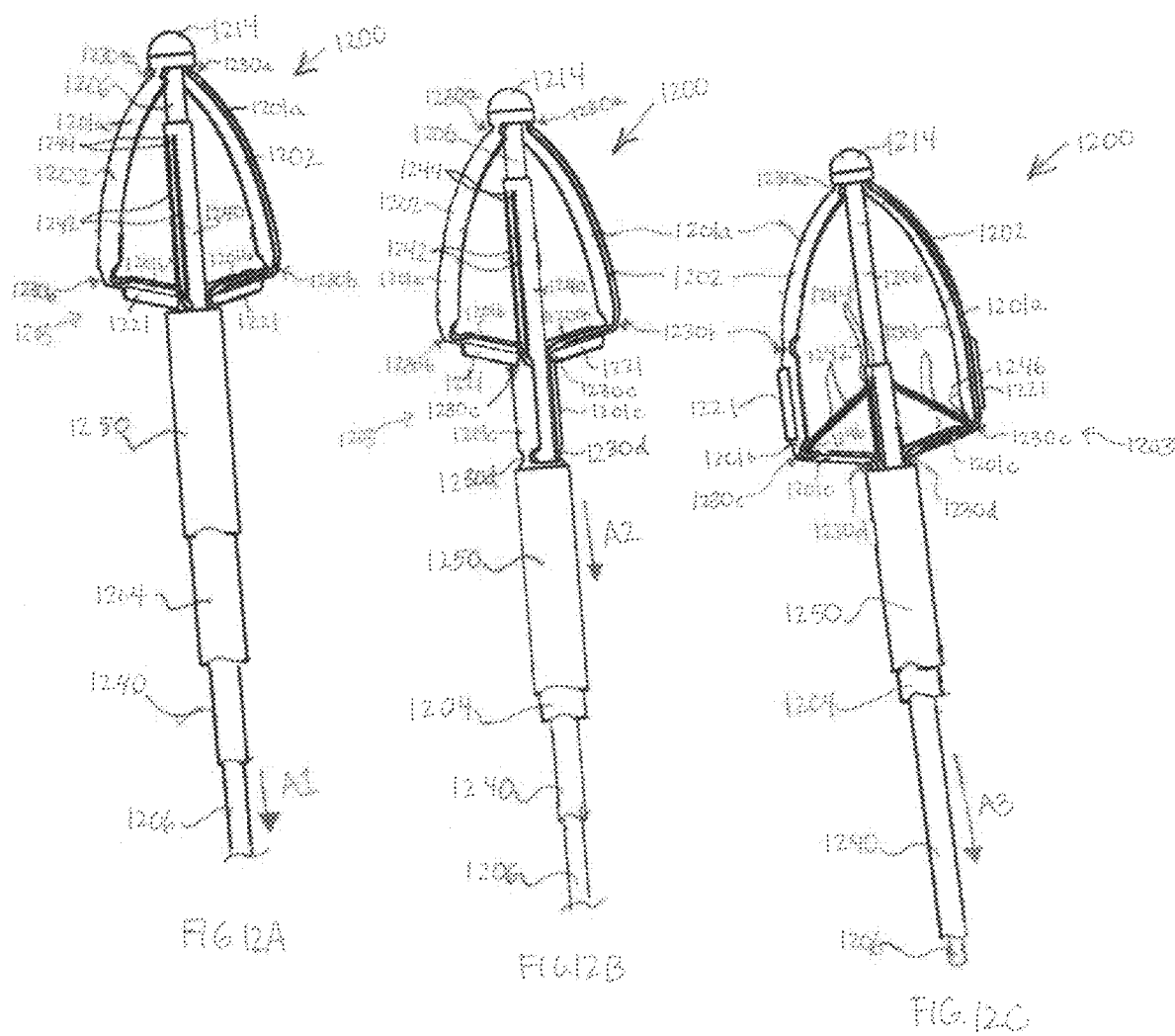

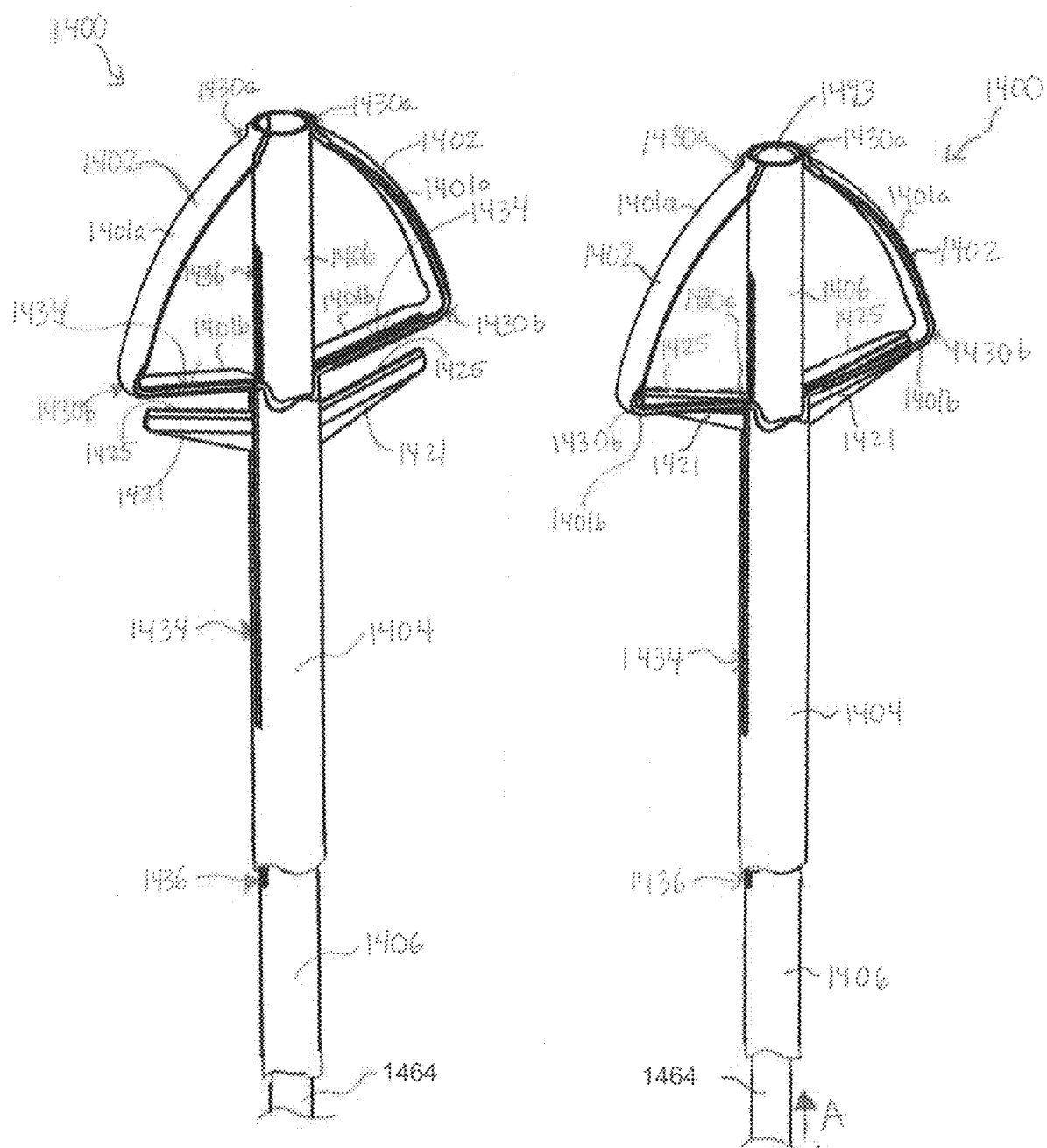

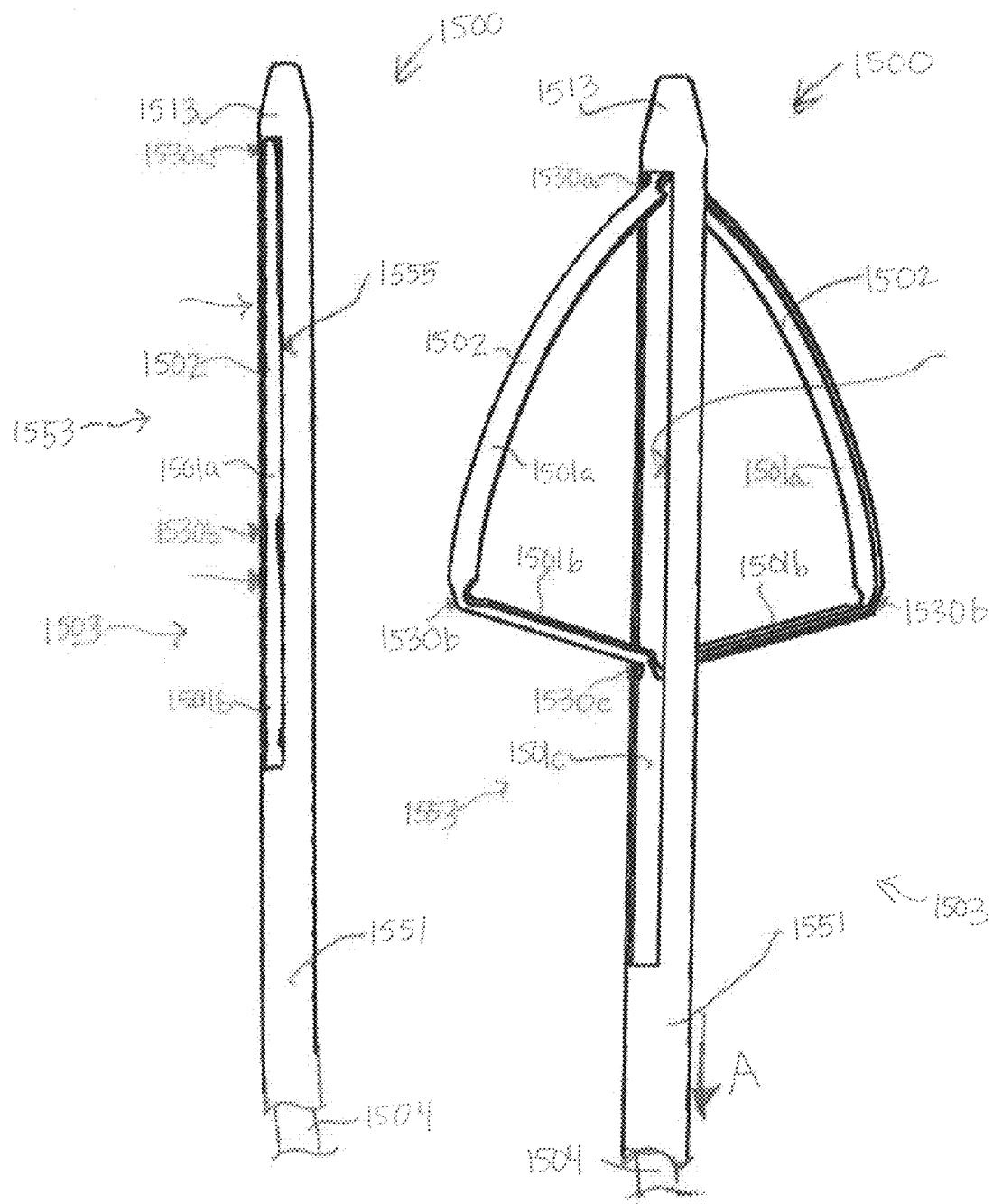

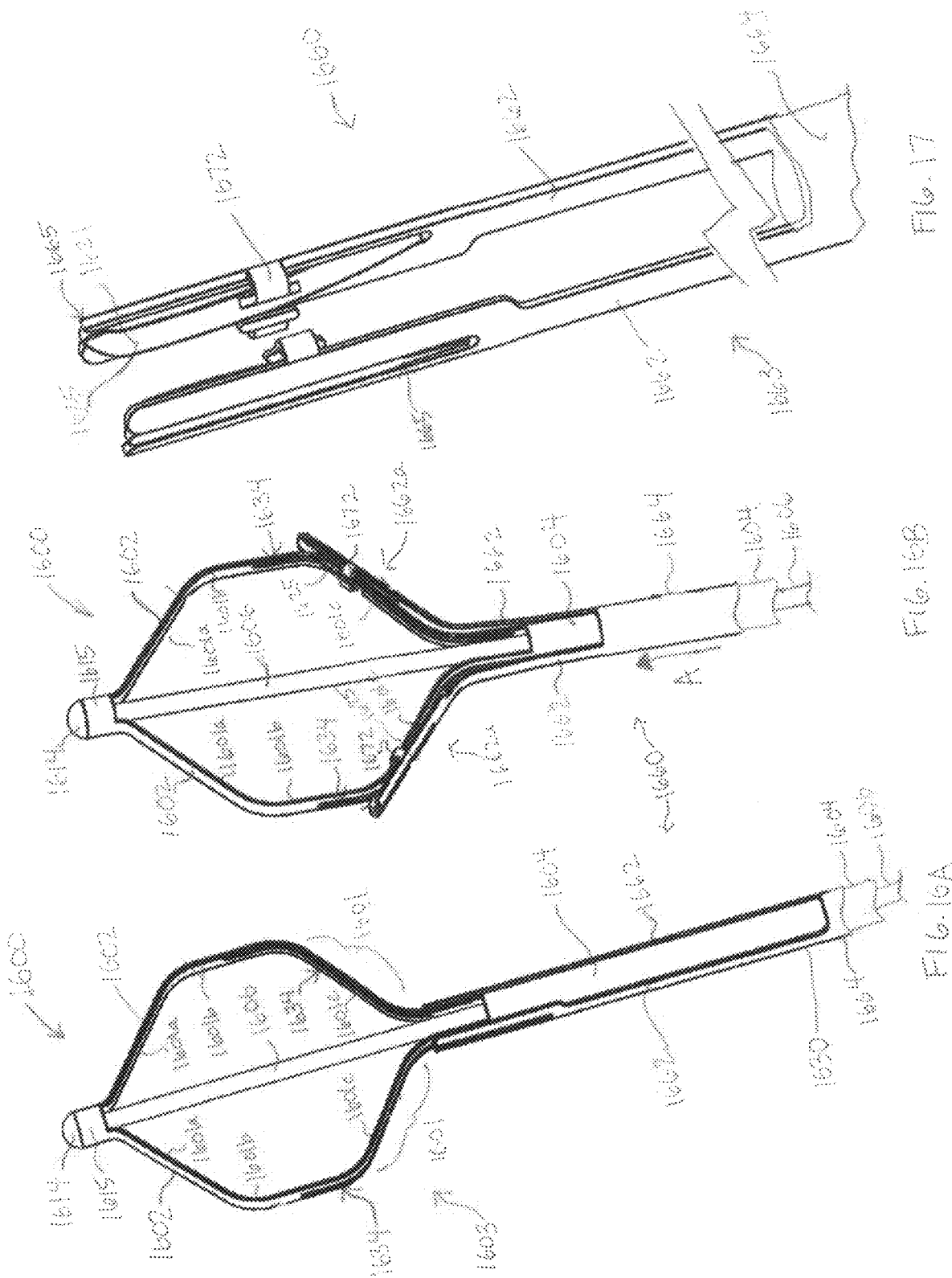

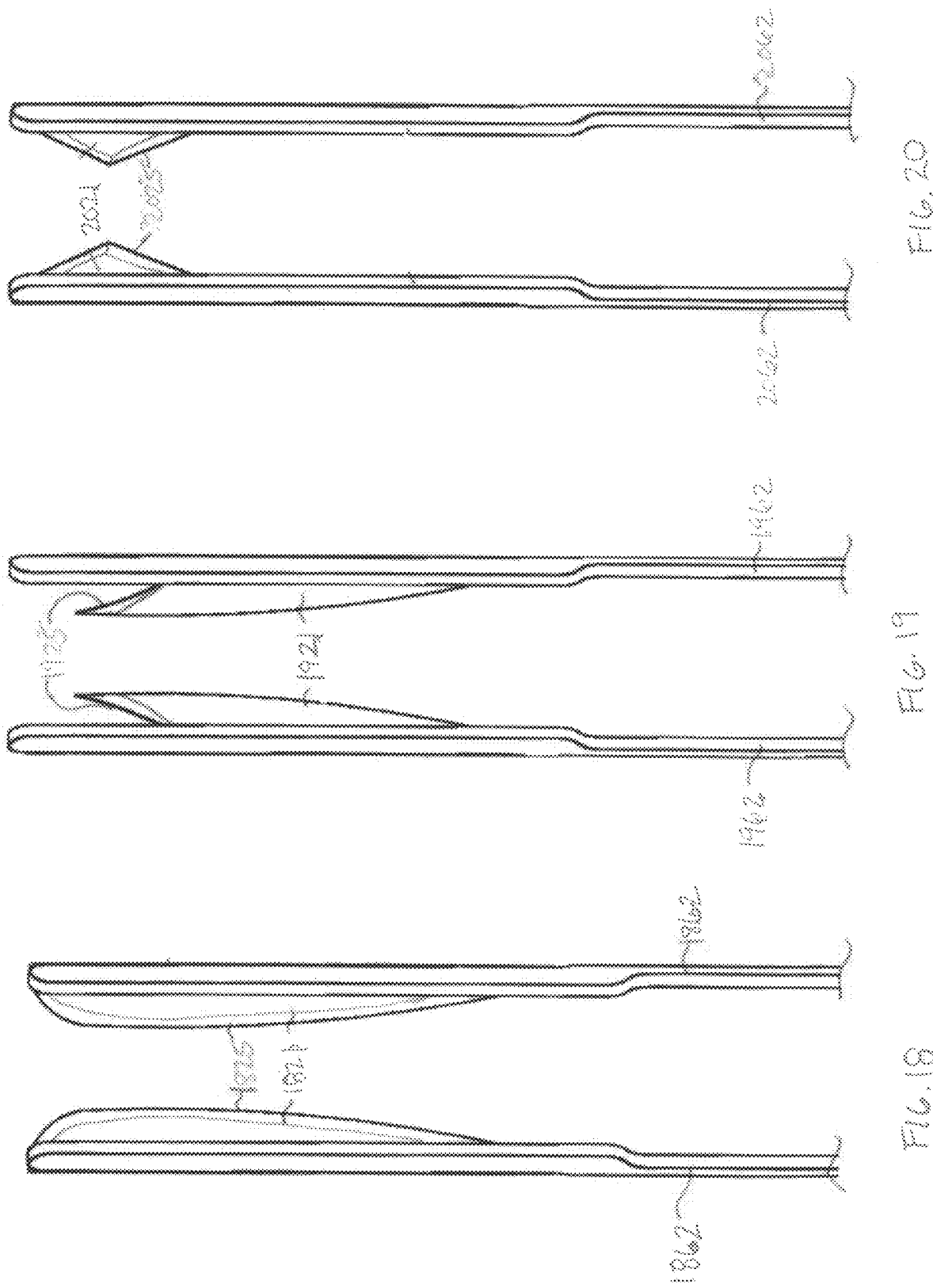

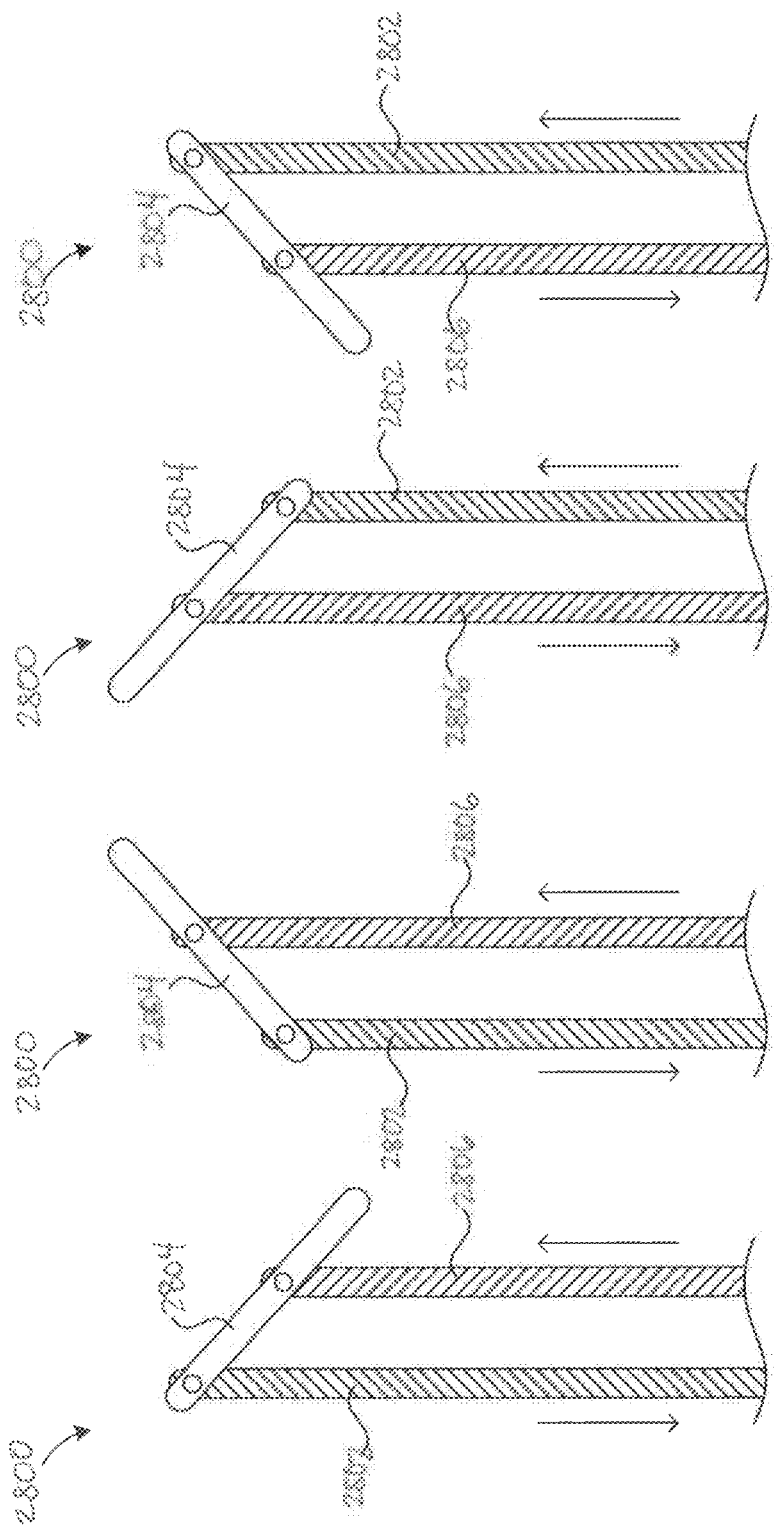

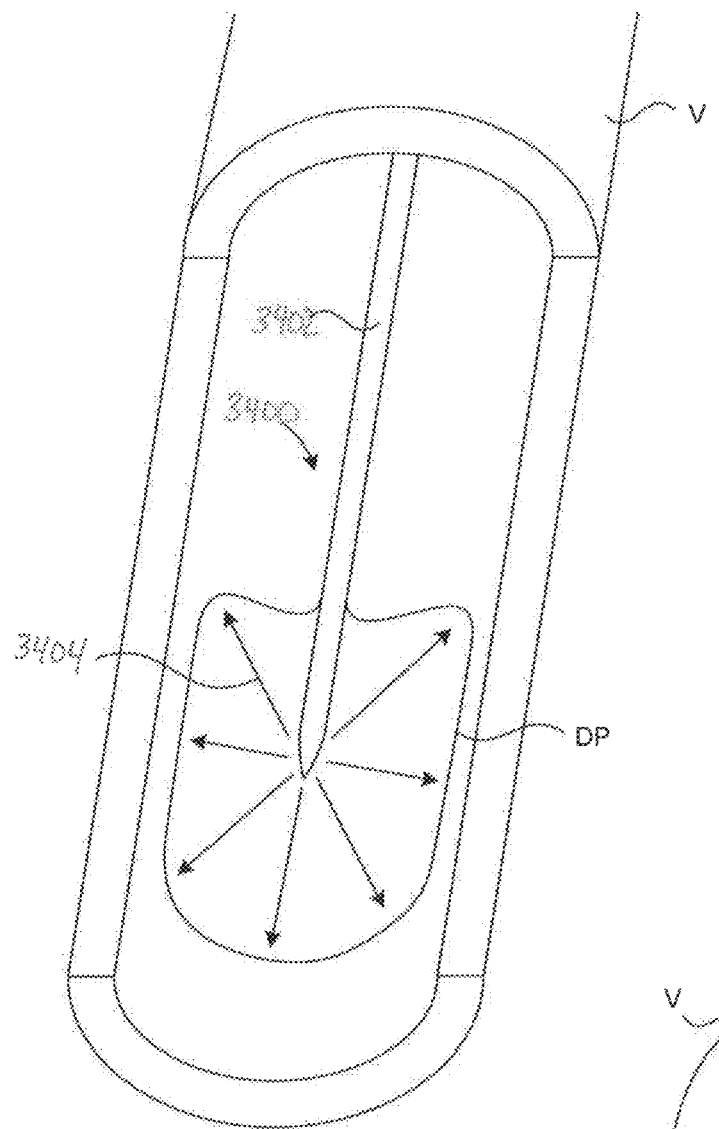
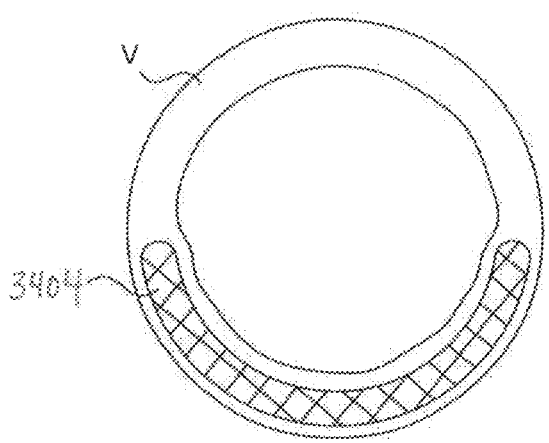
FIG. 34A
FIG. 34B

INTRAVASCULAR DEVICES, SYSTEMS, AND METHODS FOR THE CONTROLLED DISSECTION OF BODY LUMENS

CROSS-REFERENCE TO RELATED APPLICATIONS

The present application claims the benefit of U.S. Provisional Patent Application No. 62/092,809, filed Dec. 16, 2014, entitled "INTRAVASCULAR DEVICES, SYSTEMS, AND METHODS FOR CONTROLLED DISSECTION OF BODY LUMENS," which is incorporated herein by reference in its entirety.

TECHNICAL FIELD

The present technology relates generally to devices and methods for intravascular modification of body lumens. Some embodiments of the present technology relate to the intravascular creation of valve leaflets within blood vessels.

BACKGROUND

FIGS. 1A and 1B are schematic cross-sectional views of a normal human vein V. The vein V includes a valve formed of two leaflets L. FIG. 1A shows the valve in an open position in which the leaflets L separate to allow blood to flow towards the heart in the direction indicated by arrows A1. FIG. 1B shows the valve in a closed position in which the leaflets L come together to block the flow of blood away from the heart in the direction indicated by arrows A2. FIG. 1C shows a vein V' having a diseased or otherwise damaged valve comprised of leaflets L'. As shown in FIG. 1C, the leaflets L' are structurally incompetent and allow venous reflux, or the flow of venous blood away from the heart (arrows A2). Venous reflux can lead to varicose veins, pain, swollen limbs, leg heaviness and fatigue, and skin ulcers, amongst other symptoms.

Venous reflux can occur anywhere throughout the venous system, which includes superficial veins (veins closer to the skin) and deep veins. Because deep veins are harder to access, deep veins are also harder to treat surgically. Existing methods for treating damaged or diseased vein valves in deep veins include surgical repair of the diseased vein and/or valve, removal of the damaged vein, and/or vein bypass. However, all of the foregoing treatment options include relatively lengthy recovery times and expose the patient to the risks involved in any surgical procedure, such as infection and clotting. Experimental treatments such as implantable venous valves, external venous valve banding, and heat-induced vein shrinkage have been attempted but each treatment has significant shortcomings. In addition, compression stockings are sometimes used to ameliorate symptoms but do not address the underlying problem. Accordingly, there exists a need for improved devices, systems, and methods for treating damaged or diseased valves.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIG. 6A is a top view of a dissection device in a low-profile state configured in accordance with an embodiment of the present technology.

FIG. 6B is an end view of the dissection device shown in FIG. 6A.

FIG. 6C is a top view of the dissection device of FIG. 6A in a deployed state configured in accordance with an embodiment of the present technology.

FIG. 6D is an end view of the dissection device shown in FIG. 6C.

FIG. 11A is an isometric view of a dissection device configured in accordance with another embodiment of the present technology, shown in a low-profile state.

FIG. 11B is an isometric view of the dissection device shown in FIG. 11A, shown in a partially-deployed state.

FIG. 11C is an isometric view of the dissection device shown in FIGS. 11A and 11B, shown in a fully-deployed state.

FIGS. 12A-12C are isometric views of a dissection device configured in accordance with another embodiment of the present technology, shown during various stages of deployment.

FIGS. 14A and 14B are isometric views of another embodiment of a dissection device configured in accordance with the present technology, shown during various stages of deployment.

FIGS. 15A and 15B are isometric views of another embodiment of a dissection device configured in accordance with the present technology, shown in a low-profile state and a deployed state, respectively, FIGS. 16A and 16B are isometric views of another embodiment of a dissection device configured in accordance with the present technology, shown during various stages of deployment.

FIG. 17 is an isometric view of a cutting device of the dissection device shown in FIGS. 16A and 16B, shown isolated from the dissection device.

FIGS. 18-20 are front views of cutting devices that are useful with dissection devices of the present technology.

FIGS. 28A-28D are top views of a dissection device showing various states of deployment configured in accordance with an embodiment of the present technology.

FIG. 34A is a top perspective view of a dissection device shown within a blood vessel and configured in accordance with an embodiment of the present technology. The blood vessel is shown in partial cross-section for ease of illustration.

FIG. 34B is a cross-sectional end view of a gel deployed within the vessel wall.

DETAILED DESCRIPTION

The present technology provides devices, systems, and methods for the controlled dissection of tissue adjacent a body lumen. For example, some embodiments of the present technology are directed to the intravascular creation of one or more dissection pockets within a blood vessel wall, as well as the intravascular creation of one or more valve leaflets from a blood vessel wall. An overview of the novel methodology of the present technology in conjunction with general aspects of one of the anatomical environments in which the disclosed technology operates is described below under heading 1.0 ("Overview") with reference to FIGS. 2A-2F. Particular embodiments of the technology are described further under heading 2.0 ("Representative Embodiments") with reference to FIGS. 3A-26. Additional embodiments are described under heading 3.0 ("Additional Embodiments") with reference to FIGS. 27A-34B.

1.0 OVERVIEW

Figure 1A:
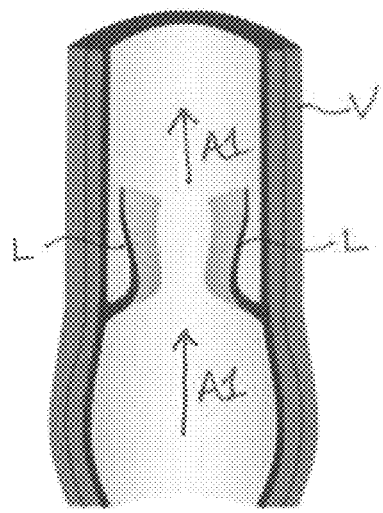
FIGS. 1A and 1B are schematic cross-sectional views of a normal human vein.
Figure 1B:
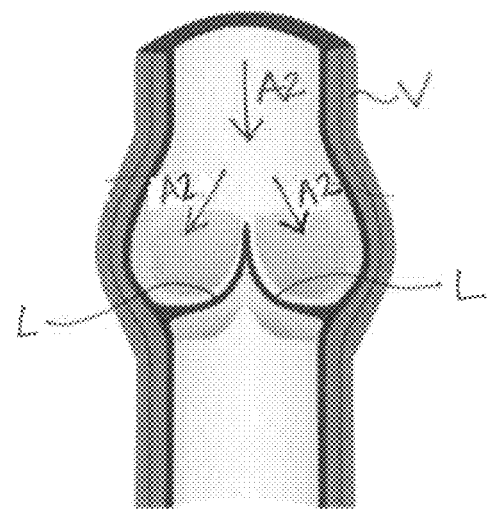
Figure 1C:
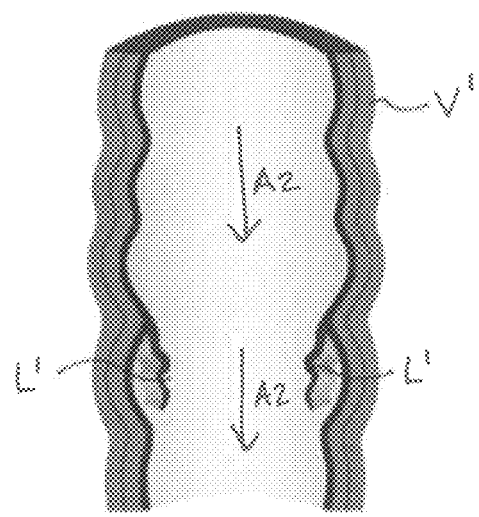
FIG. 1C is a schematic cross-sectional view of an irregular human vein having a damaged or diseased valve.
Figure 2A:
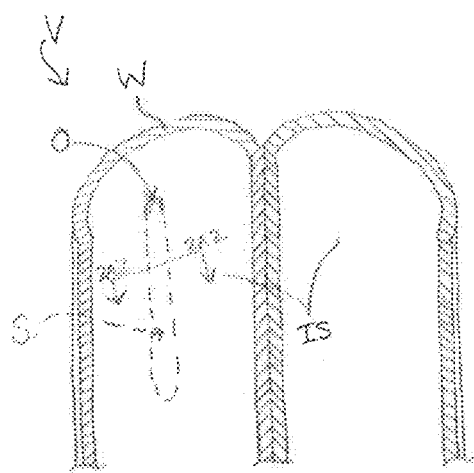
FIG. 2A is a front-elevated, splayed view of a blood vessel showing an opening at an interior surface of the blood vessel wall and a space within the blood vessel wall.
Figure 2B:
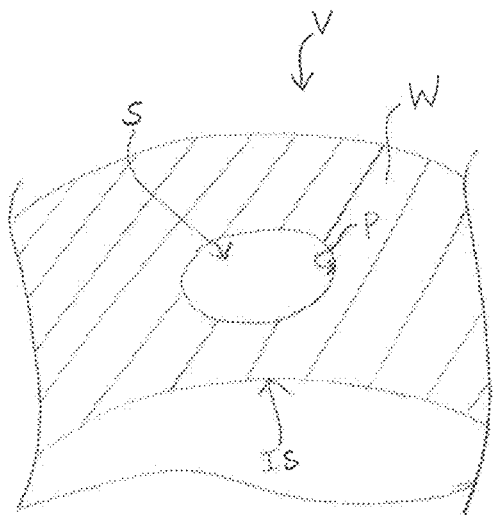
FIG. 2B is a cross-sectional end view of the space shown in FIG. 2A.

FIGS. 2A-2F are schematic, splayed views of a blood vessel V (e.g., a vein) showing the interior of the blood vessel V during various stages of a method for the intravascular creation of a dissection pocket and/or a valve leaflet from a blood vessel wall W in accordance with the present technology. FIGS. 2A and 2B illustrate a first stage of the method in which an opening O is made in the interior surface IS of the vessel wall W to gain access to an interior portion of the vessel wall W. During this first stage, an access space S is created within the vessel wall W for the subsequent delivery of one or more dissection devices of the present technology. Creation of the opening O and/or space S can be achieved using a dissection device of the present technology and/or a separate device, such as one or more of the dissection assemblies and/or inner members disclosed in U.S. patent application Ser. No. 14/667,670, filed Mar. 24, 2015, U.S. patent application Ser. No. 13/035,752, filed Feb. 25, 2011, and U.S. patent application Ser. No. 13/450,432, filed Apr. 18, 2012, all of which are incorporated herein by reference in their entireties. Once the dissection device is positioned within the space S, the dissection device can be deployed to separate tissue at the periphery P (FIG. 2B) of the space S. As shown in FIGS. 2A-2D, the enlarged space S forms a dissection pocket DP having a predetermined size and shape and extending along a dissection plane P within the vessel wall W. To transform the dissection pocket DP into a leaflet L (shown in FIGS. 2E and 2F), the dissection device and/or a separate cutting device of the present technology can be used to cut the tissue at the proximal edge E of the dissection pocket DP adjacent the opening O. For example, the dissection device and/or cutting device can cut the vessel wall tissue at the edge of the dissection pocket DP that extends laterally away from the opening O, as indicated by arrows A in FIG. 2C.

It will be appreciated that the foregoing description is intended as a reference as and does not limit the description of the present technology presented herein. Additionally, with regard to the terms "distal" and "proximal" within this description, unless otherwise specified, the terms can reference a relative position of the portions of a dissection device and/or an associated delivery device with reference to an operator and/or a location in the vasculature.

2.0 REPRESENTATIVE EMBODIMENTS OF CONTROLLED DISSECTION DEVICES AND METHODS OF USE

Figure 3A:
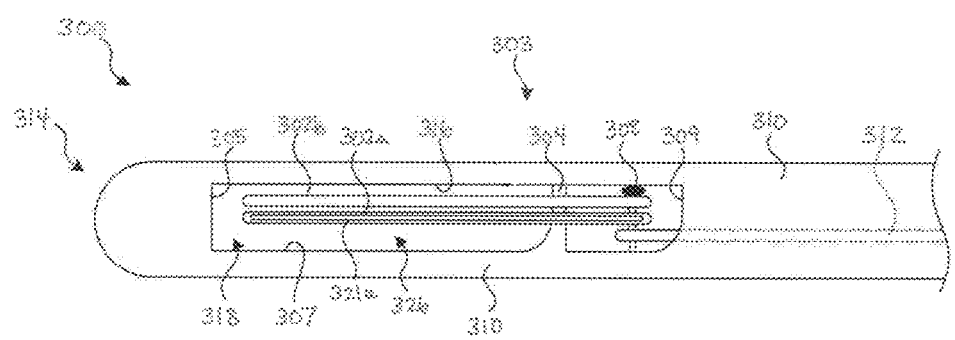
FIG. 3A is a side view of a distal portion of a dissection device configured in accordance with an embodiment of the present technology.

FIG. 3A is a side view of a distal portion of a dissection device 300 in a low-profile state configured in accordance with the present technology. The dissection device 300 can include an elongated shaft 310 having a proximal portion (not shown) and a distal portion 303 configured to be delivered intravascularly to a treatment site proximate the wall of a body lumen (e.g., a blood vessel) and positioned within the wall at the treatment site. In some embodiments, the elongated shaft 310 can be configured to be slidably received within a lumen of a delivery and/or guide catheter (not shown) for intravascular delivery to the treatment site. As shown in FIG. 3A, the dissection device 300 can include one or more moveable arms (referred to collectively as dissection arms 302, referred to individually as first and second dissection arms 302a, 302b) configured to extend laterally beyond the shaft 310 and into a portion of the lumen wall adjacent the shaft 310, thereby separating the portion into two distinct layers, as described in greater detail below.

Figure 3B:
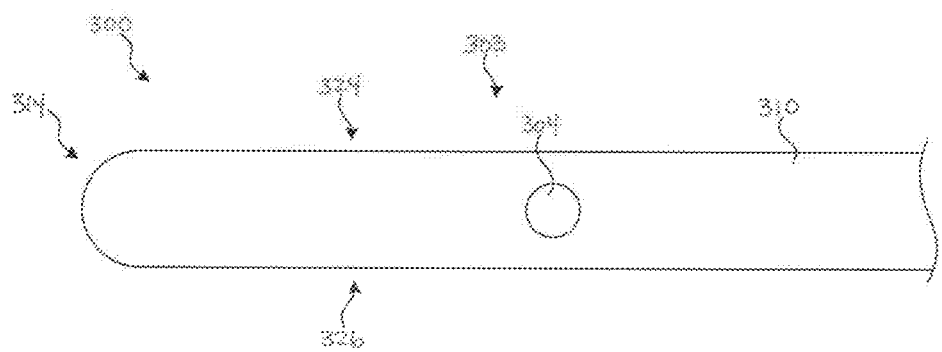
FIG. 3B is a top view of the distal portion shown in FIG. 3A.

FIG. 3B is a top view of the distal portion of the dissection device 300 shown in FIG. 3A. Referring to FIGS. 3A and 3B together, the distal portion 303 of the elongated shaft 310 can include a rounded, atraumatic end region 314 and an aperture 318 (FIG. 3A) proximal of the end region 314 that extends laterally through the shaft 310. In some embodiments, the end region 314 can alternatively include a sharpened tip (not shown) configured to gain access to the interior portion of the lumen wall. The aperture 318 can be bounded by a distal sidewall 305, a bottom sidewall 304, a proximal sidewall 309, and a top sidewall 320. As such, the shaft 310 can include a first opening 324 at one side of the aperture 318 and a second opening 326 at the opposite side of the aperture 318. At least the distal portion 303 can be positioned within the aperture 318 such that, when deployed, the first and second dissection arms 302a, 302b extend laterally through the first and second openings 324, 326, respectively. In some embodiments (not shown), one or more of the sidewalls 305, 307, 309 and 320 can be modular to facilitate device assembly. For example, in some embodiments, the top sidewall 320 can be a separate piece that, during assembly, can be fixed in place after positioning the dissection arms 302 within the aperture 318.

Figure 3C:
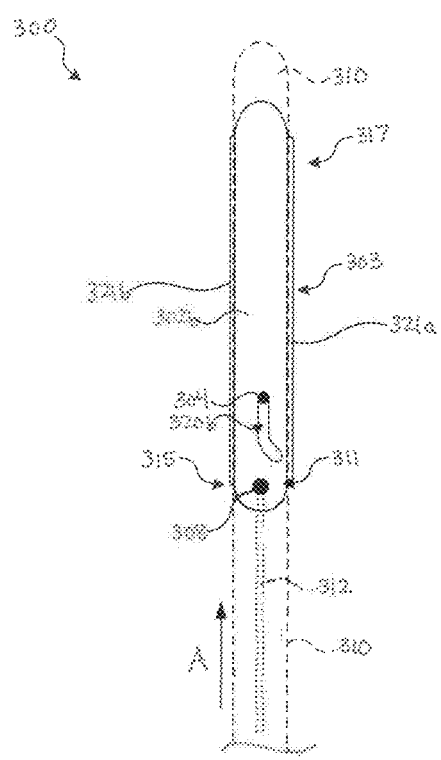
FIG. 3C is a top isolated view of a dissection device in a low-profile state configured in accordance with an embodiment of the present technology.
Figure 3D:
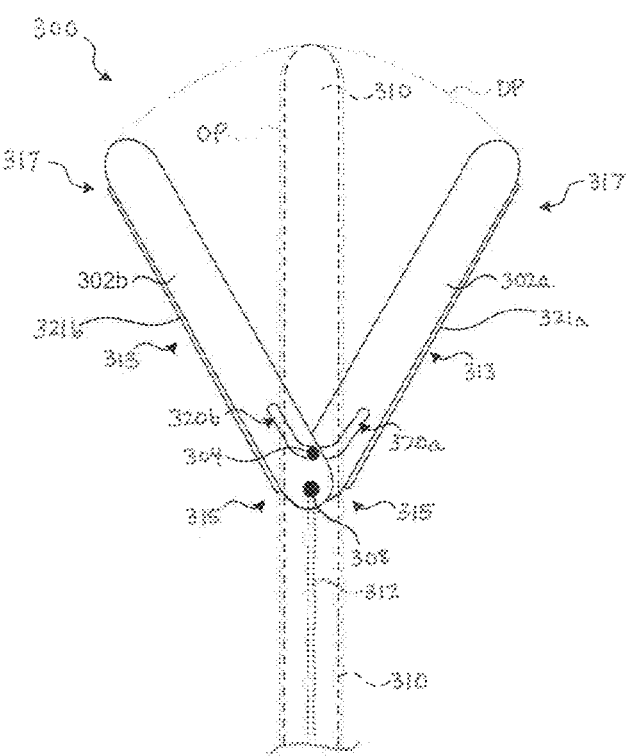
FIG. 3D is a top isolated view of a dissection device in a deployed state configured in accordance with an embodiment of the present technology.

FIG. 3C is a top view of the dissection device 300 in a low-profile state, and FIG. 3D is a top view of the dissection device 300 in a deployed state. The elongated shaft 310 is shown in phantom lines to better illustrate the dissection arms 302. Referring to FIGS. 3A-3D together, the dissection device 300 includes an elongated actuation member 312 configured to move from the low-profile state of FIG. 3C to the deployed state of FIG. 3D. Although the dissection device 300 is shown with two dissection arms 302 in FIGS. 3A-3D, in other embodiments the dissection device 300 can have a single arm or more than two arms. As shown in FIGS. 3C-3D, the dissection arms 302 can individually include a proximal region 315 rotatably coupled to the elongated actuation member 312 via a linkage 308, a distal region 317, and a curved slot (labeled individually as first and second slots 320a, 320b) positioned between the proximal and distal regions 315, 317. The curved slots 320 can be configured to receive a coupling element 307 extending from or affixed to the elongated shaft 310. For example, in the embodiment shown in FIGS. 3A-3D, the coupling element 307 can be a pin or other mechanical-linkage that extends from the elongated shaft 310 across the aperture 318 through the first and second slots 320a, 320b.

As best shown in FIGS. 3C and 3D, in some embodiments the dissection arms 302 can be generally flat and can have a rectangular shape with rounded corners. In other embodiments, the individual dissection arms 302 can have a slight bend along a longitudinal direction (e.g., non-flat) and/or can have any suitable shape and/or configuration. Although the slots 320 shown in FIGS. 3C and 3D are curved, in other embodiments the slots 320 can be linear and/or contain one or more linear segments. In the illustrated embodiment, a cutting element 321 (labeled individually as first and second cutting elements 321a, 321b) is attached to at least a portion of the outer edge 313 of each of the dissection arms 302. As such, the dissection arms 302 can have an atraumatic distal portion 317 configured for blunt dissection, and a sharpened portion along the length of the cutting element 321a, 321b. In some embodiments (not shown), the dissection arms 302 may not include any cutting element. Additionally, in particular embodiments, the entire outer edge 313 can be sharp or beveled to facilitate the outer edge 313 being able to cut through the vessel wall during deployment, if desired. In other embodiments, the outer edge 313 of each of the dissection arms 302 can be atraumatic.

Although the slots 320 shown in FIGS. 3C and 3D have a single bend, in other embodiments the slots 320 can have multiple bends, segments and/or can comprise complex shapes. For example, the shape of the slots 320 and/or position of the slots 320 along the dissection arms 302 can be chosen to affect a particular rotation of the dissection arms 302 around the coupling element 307, thereby creating a dissection pouch of a desired geometry within the vessel wall. Moreover, in some embodiments the dissection arms 302 can have slots 320 of the same size and/or shape, and in some embodiments the dissection arms 302 can have slots 320 of different sizes and/or shapes.

Referring still to FIGS. 3A-3D, the actuation member 312 can have a proximal portion (not shown) and a distal portion 311, and can be configured to move axially within the elongated shaft 310 to affect rotation of the dissection arms 302. The actuation member 312 can extend distally from the proximal portion through a lumen of the elongated shaft 310 to the distal portion of the shaft 310 and/or the aperture 318. In some embodiments, the actuation member 312 can be a push/pull rod. In other embodiments, other suitable actuation devices and methods known in the art can be used to deploy the dissection arms 302 of the dissection device 300.

In the low-profile state (FIG. 3C), the dissection arms 302 of the dissection device 300 can be generally aligned with the elongated shaft 310 (shown in phantom lines) such that the majority of each arm 302 lies within the lateral boundaries of the elongated shaft 310. In some embodiments, each of the arms 302 in their entireties lies within the lateral boundaries of the elongated shaft 310. To deploy the dissection device 300, the actuation member 312 can be pushed distally as indicated by arrow A (e.g., from the proximal portion), thereby urging the dissection arms 302 in a distal direction. As shown in FIG. 3D, as the dissection arms 302 are urged distally, the individual slots 320a, 320b slide along the coupling element 307, thereby forcing the dissection arms 302 to rotate based on the shape of each slot 320a, 320b. As the dissection arms 302 rotate, they extend laterally through the openings 324, 326 (FIG. 3A) in the elongated shaft 310 and engage the lumen wall tissue adjacent the shaft 310. The edge 313 of the individual dissection arms 302 separates layers or stratums of the wall tissue from each other as the dissection arms 302 move outwardly and away from the longitudinal axis of the shaft 310. The edge 313 of each arm 302 can separate the tissue by shear force (atraumatic edges) or by cutting the tissue (sharp edges), or both. As such, movement of the dissection arms 302 separates the tissue at the periphery of the space S (FIGS. 2A and 2B) in which it sits within the vessel wall and creates a dissection pocket DP (FIGS. 2C and 2D) having a geometry dictated, at least in part, by the size and shape of the dissection arms 302, as well as the path of the edges 313 of the dissection arms 302 through the tissue. For example, as shown in FIG. 3D, the dissection arms 302 of the dissection device 300 can be configured to create a dissection pocket having a rounded distal-most edge. A rounded distal periphery can be advantageous, especially when forming autologous leaflets within the vasculature, as the rounded contour promotes the flushing of old blood out of the dissection pocket DP during each venous pumping cycle, thereby preventing clotting within the dissection pocket DP.

Although the dissection arms 302 of FIGS. 3C-3D are shown rotating about 30 degrees from a longitudinal axis of the elongated shaft 310, in other embodiments the slots 320 and/or dissection arms 302 can be configured to rotate any suitable distance to achieve a desired dissection pocket shape (such as that shown in FIG. 2B).

One method for using the dissection device 300 is described with reference to FIGS. 2A-2F. The dissection device 300 can be positioned within the blood vessel V (e.g., a vein) proximate a treatment site. The dissection device 300 can then be inserted through the opening O (FIG. 2A) in the vessel wall W and be positioned within the access space S within the vessel wall W. In some embodiments, the dissection 300 can be used to create the opening O and/or access space S. For example, in some embodiments the dissection device 300 can have a sharp distal edge that can penetrate the vessel wall W. Upon placement of the distal portion 303 within the vessel wall W, the actuation member 312 can be advanced distally to expand the dissection arms 302 laterally away from a longitudinal axis of the dissection device 300. As the dissection arms 302 move outwardly, the edges 303 of the dissection arms 302 separate the vessel wall tissue into two layers (e.g., via blunt dissection and/or sharp dissection) to form a dissection pocket DP having a desired size and shape. Once the dissection pocket DP is formed, the dissection device 300 can be pulled proximally such that the cutting elements 321 engage tissue at a proximal edge E of the dissection pocket DP extending laterally from the opening O and cut the tissue to transform the opening O into a mouth M (FIG. 2C), thereby forming a leaflet L. In other embodiments, the opening O can be widened with a separate device. The mouth can extend along a circumferential length of the vessel wall between 90 or about 90 degrees and 330 or about 330 degrees. Depending on the size of the mouth M desired, the actuation member 312 can be withdrawn proximally to move the dissection arms 302 inwardly towards the longitudinal axis of the device 301, before retraction of the device 301, thereby decreasing the reach of the cutting elements 321 (and thus the size of the mouth M). In some embodiments, the device 301 can widen the opening O while being retracted in the low-profile state, as the proximal portion of the cutting elements 321 create the mouth M.

Figures 4A, 4C:
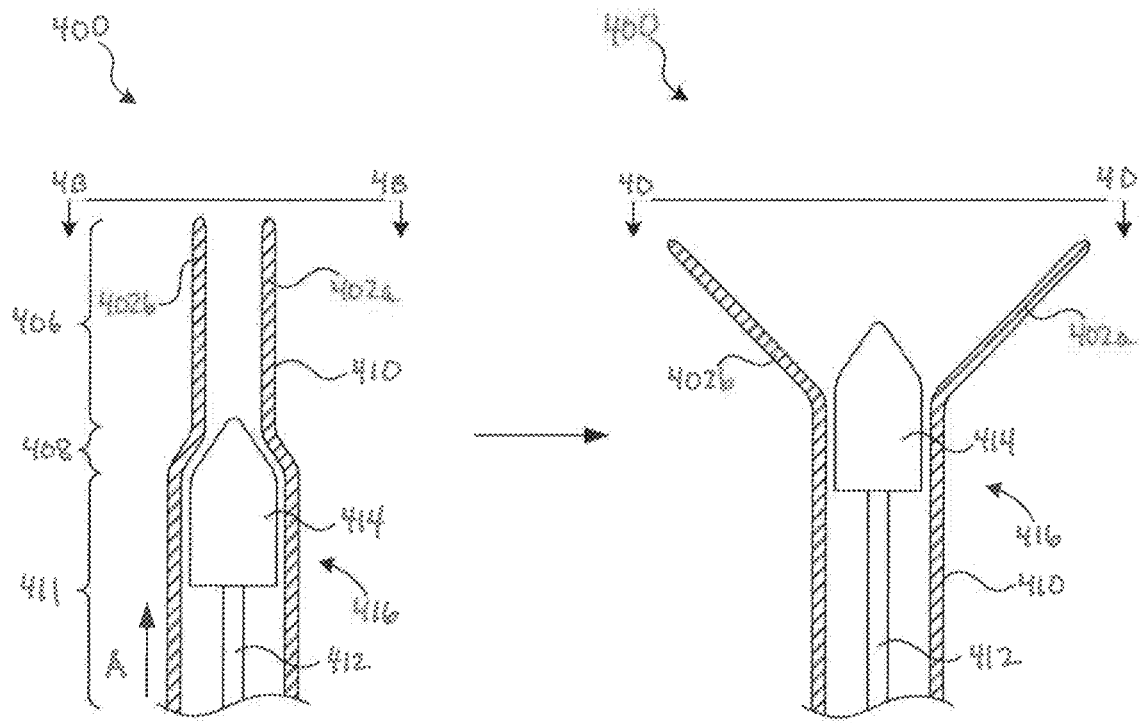
FIG. 4A is a cross-sectional side view of a dissection device in a low-profile state configured in accordance with an embodiment of the present technology.
FIG. 4C is a cross-sectional side view of the dissection device shown in FIG. 4A in the deployed state configured in accordance with an embodiment of the present technology.
Figures 4B, 4D:
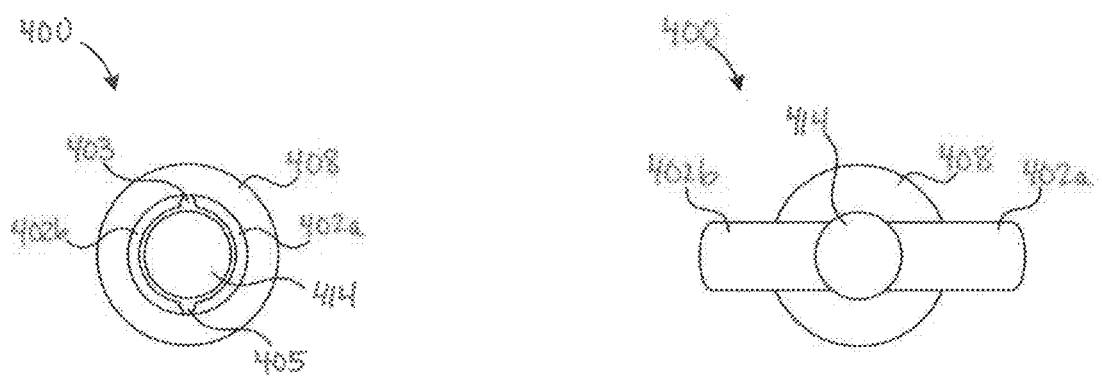
FIG. 4B is a top view of the dissection device shown in FIG. 4A.
FIG. 4D is a top view of the dissection device shown in FIG. 4C.

FIGS. 4A and 4B are cross-sectional top and end views, respectively, of an alternate dissection device 400 in a low-profile state configured in accordance with an embodiment of the present technology. The dissection device 400 can include a tubular shaft 410 and an actuation member 420 configured to be slidably received by the shaft 410. The actuation member 420 can include an elongated push/pull rod 412 and an expander 414 coupled to a distal portion of the push/pull rod 412. The tubular shaft 410 can include a proximal portion 411, a tapered portion 408, and a distal portion 406. As shown in FIG. 4A, the inner diameter of the proximal portion 411 can be greater than the inner diameter of the distal portion 406. For example, the shaft 410 can comprise a deformed hypotube (e.g., made of Nitinol, stainless steel, etc.). The distal portion 406 of the shaft 410 can include a first slot 403 and a second slot 405 (FIG. 4B) spaced apart from the first slot 403 along the circumference of the distal portion 406. The first and second slots 403, 405 can extend along the length of the distal portion 406, thereby dividing the distal portion 406 into a first arm 402a and a second arm 402b. As such, the first and second arms 402a, 402b are configured to bend relative to at least the proximal portion 411 of the shaft, as well as freely of one another.

FIGS. 4C and 4D are cross-sectional top and end views, respectively, of the dissection device 400 in a deployed state configured in accordance with an embodiment of the present technology. As shown in FIGS. 4C and 4D, as the actuation member 420 is advanced distally, the expander 414 forces the first and second arms 402a, 402b outwardly, away from the longitudinal axis of the device 400. In some embodiments, the slots 403, 405 can occupy the same circumference of the distal portion and be spaced 180 degrees or about 180 degrees apart from one another such that arms 402a, 402b expand outwardly within generally the same plane, as shown in FIG. 4D.

Figure 5A:
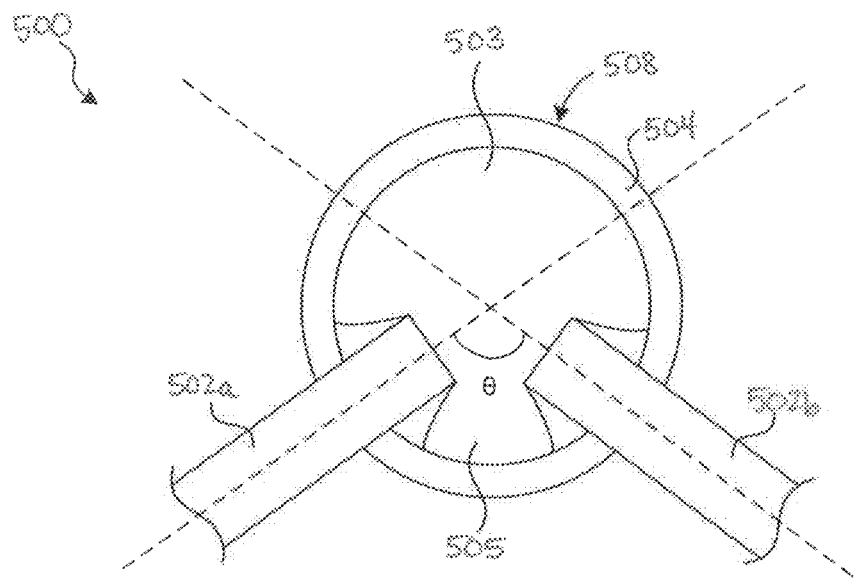
FIG. 5A is a top view of a dissection device configured in accordance with another embodiment of the present technology, shown in a deployed state.
Figure 5B:
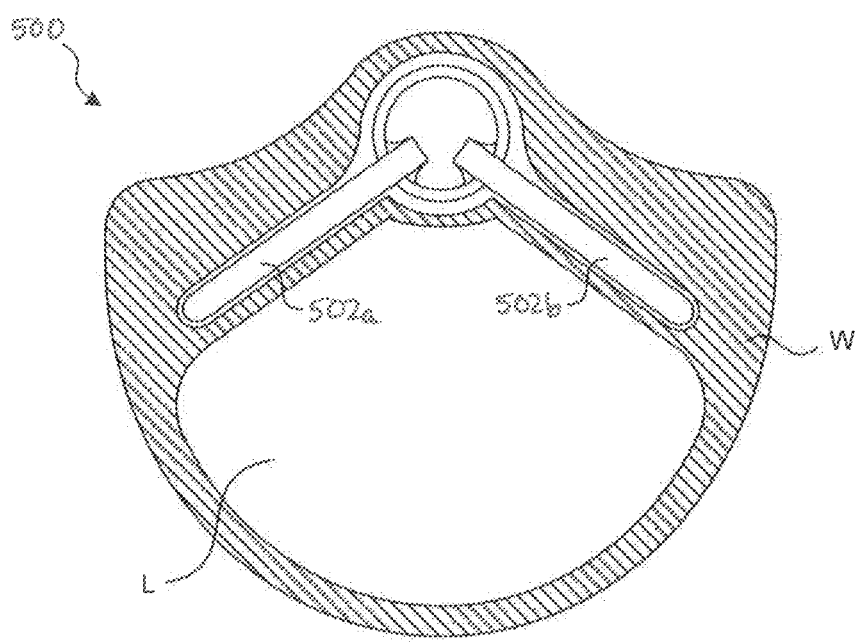
FIG. 5B is a partial cross-sectional end view of the dissection device of FIG. 5A shown deployed in a blood vessel wall.

FIG. 5A is an end view of a dissection device 500 having angled arms 502a, 502b configured in accordance with the present technology (the actuation member is not shown for ease of illustration). The dissection device 500 of FIG. 5A can be generally similar to the dissection device 400 of FIG. 4A, except the first slot 503 of FIG. 5A takes up a larger portion of the circumference of the distal portion than the second slot 505. As a result, the first and second arms 502a, 502b extend outwardly from the shaft at a non-180 degree angle with respect to one another (and thus not within the same plane). Such a configuration can be advantageous, especially when used for creation of dissection pockets within tubular or curved body lumens, such as blood vessels. Because access to the interior portion of the vessel wall is limited to a narrow access channel C within the wall (see FIG. 2B), dissection of the wall begins at the narrow access channel and propagates from both sides of the channel laterally away from the channel along the circumference of the vessel. As the wall tissue can be fragile, it can be advantageous to reduce the amount of stretching of the newly-created wall layers, especially in a direction perpendicular to the longitudinal axis of the vessel. As shown in the anatomical end view of FIG. 5B, the angled arms 502 of the dissection device 500 reduces such stretching by providing a separating force in an angled plane that closely mimics the curvature of the vessel wall V. As such, the slots 503, 505 can have any suitable sizing and/or configuration to achieve a desired arm angle based on the size and curvature of the targeted lumen L. For example, in this and any embodiment of the present technology, the arms can deploy at an angle θ (see FIG. 5A) of between about 100 degrees and about 179 degrees. In some embodiments, the angle θ can be between about 115 degrees and 205 degrees. Additionally, the angle θ can be between about 120 degrees and about 140 degrees. In a particular embodiment, the angle θ can be about 130 degrees.

FIG. 6A is a top view of another embodiment of a dissection device 600 in a low-profile state configured in accordance the present technology. FIG. 6B is an end view of the dissection device 600 shown in FIG. 6A. Referring to FIGS. 6A and 6B together, the dissection device 600 can include an elongated pull member 606 slidably positioned at least partially within a shaft 604. The pull member 606 can include a proximal portion (not shown) and a distal portion 607. The shaft 604 can include a distal portion 603 having first and second arms 602a, 602b. For example, in the embodiment shown in FIGS. 6A and 6B, the distal portion 603 of the shaft 604 is bifurcated, and the bifurcations form the first and second arms 602a, 602b. In these and other embodiments, one or more regions of the shaft 604 can be removed at the distal portion 603 to form the first and second arms 602a, 602b. The distal portion 607 of the pull rod 606 can be coupled to a distal portion of each of the arms 602a, 602b via a coupling element 610, such as a pin or other suitable mechanical linkage. Alternatively, the distal portion 607 of the pull rod 606 can be coupled to a distal portion of each of the arms 602a, 602b via a solder, weld, or swage joint.

FIG. 6C is a top view of the dissection device 600 in the deployed state configured in accordance with an embodiment of the present technology. FIG. 6D is an end view of the dissection device 600 shown in FIG. 6C. Referring to FIGS. 6C and 6D together, to deploy the dissection device 600, the pull rod 606 can be pulled proximally while the shaft 604 can remain relatively fixed. The proximal movement of the pull rod 606 pulls the distal portions of the arms 602a, 602b proximally and forces the arms 602a, 602b to bend outwardly away from the longitudinal axis of the shaft 604. As shown in FIG. 6D, the arms 602a, 602b can extend laterally generally within the same plane (e.g., the first and second arms 602b extend from the shaft 604 in first and second directions, respectively, that are 180 degrees or about 180 degrees of one another). In other embodiments, the arms 602a and 602b can extend at an angle θ with respect to one another that is between about 135 degrees and about 180 degrees. Such a configuration may be particularly advantageous if the desired dissection is within a curved surface, such as a vessel wall.

Figure 7:
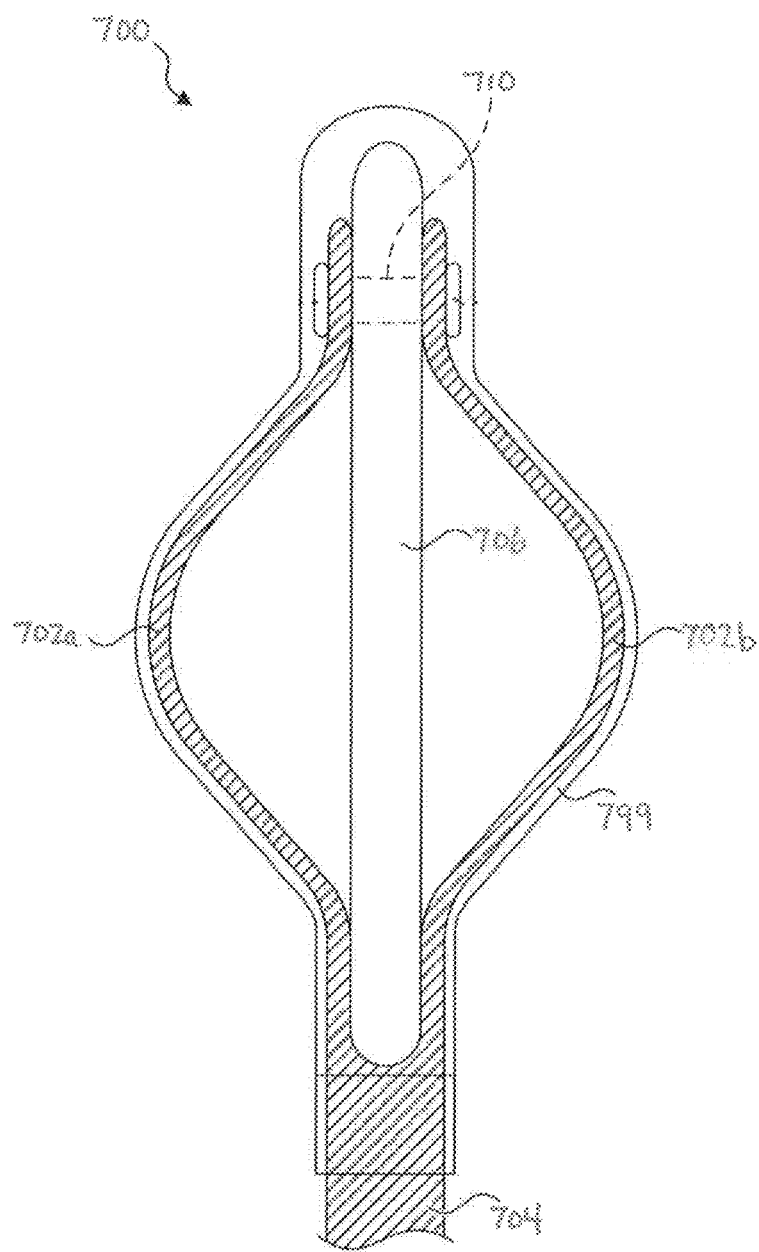
FIG. 7 shows another embodiment of a dissection device having an outer membrane configured in accordance with the present technology.

FIG. 7 is a top view of another embodiment of a dissection device 700 in a deployed state configured in accordance with the present technology. The dissection device 700 can have a shaft 704 and dissection arms 702a, 702b that are generally similar to the shaft 604 and dissections arms 602a, 602b of the dissection device 600 of FIG. 6A. The dissection device 700 of FIG. 7, however, includes a smooth, deformable membrane 799 surrounding at least a portion of the arms 702a, 702b. For example, the membrane can be made of silicone, urethane, nylon, latex, soft PEBAX, or any soft polymer or other suitable material. The membrane 799 reduces frictional forces between the dissection device 700 and the interior of the vessel wall, both during the initial insertion of the dissection device 700 into the wall, and during deployment within the wall.

Figure 8A:
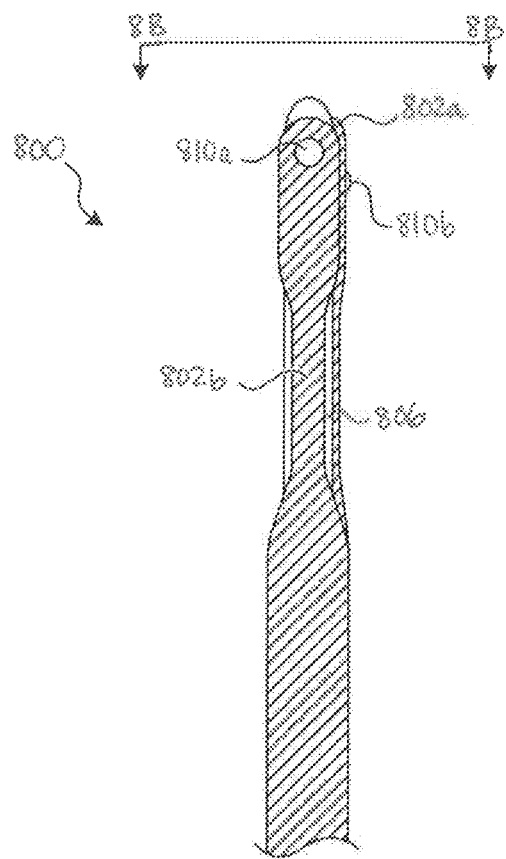
FIG. 8A is a side view of a dissection device in a low profile state configured in accordance with another embodiment of the present technology.
Figure 8B:
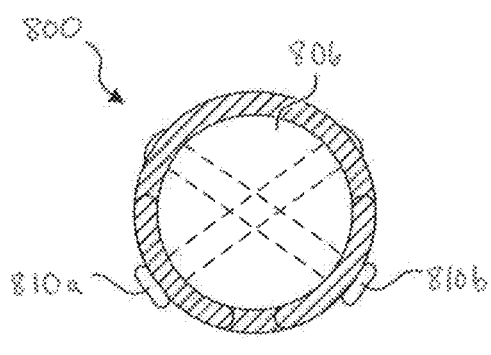
FIG. 8B is an end view of the dissection device shown in FIG. 8A.
Figure 8C:
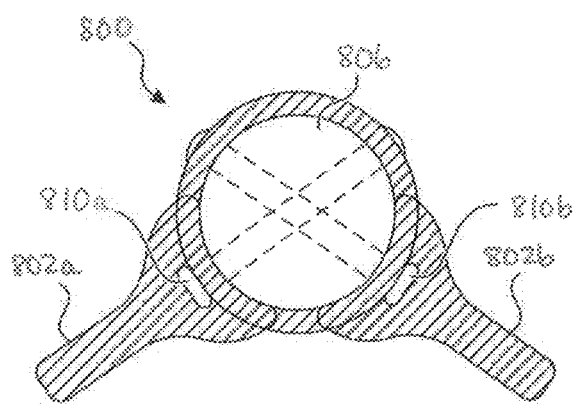
FIG. 8C is an end view of the dissection device shown in FIG. 8A in a deployed state configured in accordance with an embodiment of the present technology.

FIG. 8A is a side view of another embodiment of a dissection device 800 in a low-profile state, FIG. 8B is an end view of the dissection device 800 shown in FIG. 8A, and FIG. 8C is an end view of the dissection device 800 in a deployed state. Referring to FIGS. 8A-8C together, the dissection device 800 can have a shaft 804 and a pull rod 806 that are generally similar to the shaft 604 and pull rod 606 of the dissection device 600 of FIGS. 6A and 6B. The dissection device 800 of FIGS. 8A-8C, however, has first and second dissection arms 802a, 802b that are configured to deploy at a non-180 degree angle (or multiples thereof) relative to one another. As shown in FIGS. 8A-8C, the first and second dissection arms 802a, 802b can be positioned less than 180 degrees or less than about 180 degrees apart along the circumference of the pull rod 806 such that, when deployed, the first and second dissection arms 802a, 802b bend outwardly at angle relative to one another.

Figure 9A:
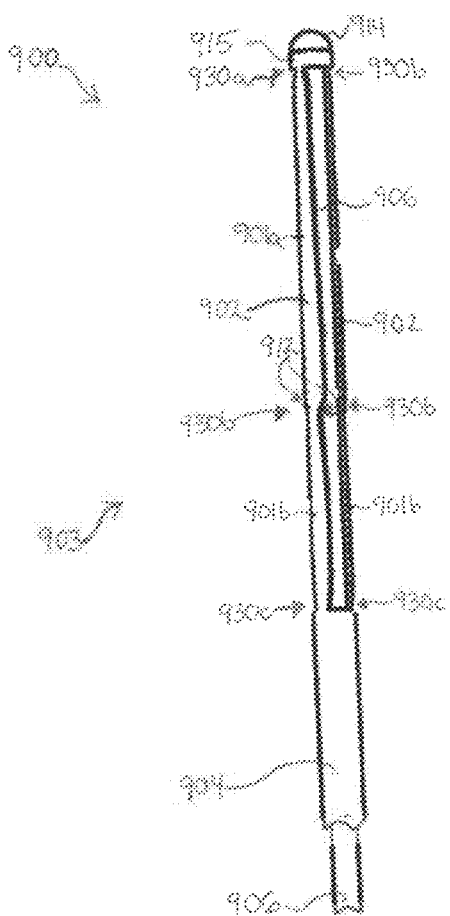
FIGS. 9A and 9B are isometric views of another embodiment of a dissection device in a low-profile state and a deployed state, respectively, configured in accordance with the present technology.
Figure 9B:
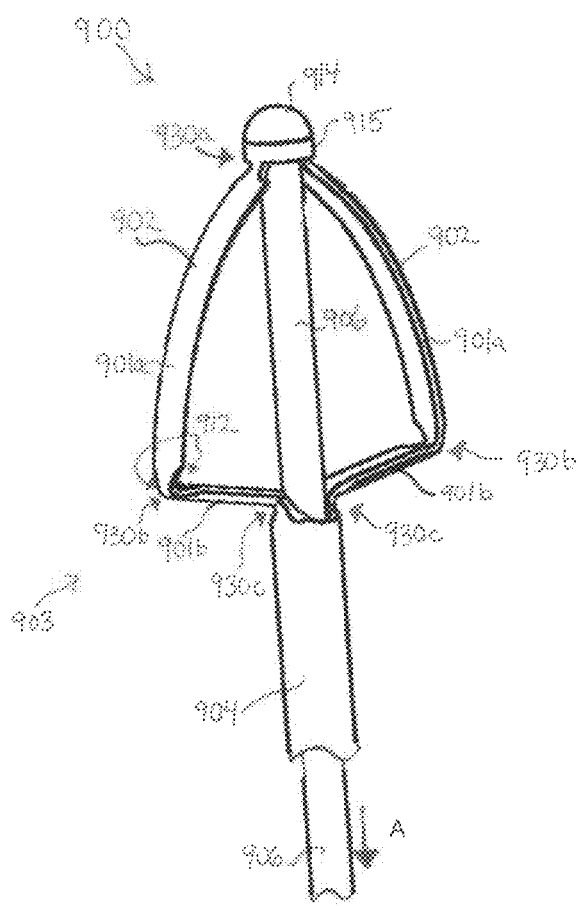

FIGS. 9A and 9B illustrate another embodiment of a dissection device 900 configured in accordance with the present technology, shown in a low-profile state and a deployed state, respectively. The dissection device 900 can include an elongated shaft 904 and a pull rod 906 slidably disposed within the shaft 904. The pull rod 906 can have an atraumatic distal end region 914. The shaft 904 can have a distal portion 903 that includes dissection arms 902 and a distal end region 915. In the embodiment shown in FIGS. 9A and 9B, one or more regions of the shaft 904 have been removed along the distal portion 903 to form the dissection arms 902. In other embodiments, the dissection arms 902 can be separate components coupled to the shaft 904. The distal end region 915 of the shaft 904 can be fixed to the distal end region 914 of the pull rod 906. As such, proximal movement of the pull rod 906 with respect to the elongated shaft 904 (as indicated by arrow A in FIG. 9B) pulls the distal portions of the dissection arms 902 proximally and forces the dissection arms 902 to bend outwardly away from the longitudinal axis of the shaft 904, as shown in FIG. 9B.

The dissection arms 902 can include one or more segments 901 (referred to individually as first and second segments 901*a*, 901*b*) and one or more joints 930 (referred to individually as first-third joints 930*a-c*). The joints 930 can be positioned along the dissection arms 902 between successive segments 901 and/or at the portions of the arms 902 that meet the shaft 904 (e.g., the proximal and distal end portions of the arms 902). The joints 930 can be portions of the dissection arms 902 and/or shaft 904 configured to preferentially flex relative to the segments 901 and/or the shaft 904. In some embodiments, one or more of the joints 930 can be formed by opposing recesses 912 at a desired location along the arm 902 (e.g., a living hinge), and in other embodiments one or more of the joints 930 can be one or more small pins, elastic polymeric elements, mechanical hinges and/or other devices that enable one segment 901 to pivot or bend relative to another.

In the embodiment shown in FIGS. 9A and 9B, each of the dissection arms 902 includes a distal joint 930*a* at its distal end portion, a proximal joint 930*c* at its proximal end portion, and an intermediate joint 930 positioned along the length of the respective arm 902 between the proximal and distal joints 930*a*, 930*c*. In response to longitudinal stresses caused by proximal movement of the pull rod 906, the dissection arms 902 deform into a predetermined shape biased by the configuration and/or relative positions of the joints 930. For example, in the illustrated embodiment, each of the dissection arms 902, when deployed, includes a generally curved distal segment 901*a* and a generally linear proximal segment 901*b* that, taken together, enclose a rounded triangular or "shield-like" shape. In other embodiments, the number of segments 901, the length of each segment 901, the angle between segments 901, and/or the shape of each segment 901 (e.g., linear, curved, etc.) can be varied along a single dissection arm and/or amongst a plurality of dissection arms to achieve a desired dissection pocket DP and/or leaflet L shape (see FIG. 2C). Moreover, the dissection arms 902 can have any suitable size and/or shape based on a desired bending stiffness, angle, and radius of curvature. Additionally, the deployed shape of the dissection arms 902 and/or the amount of tissue separated by the dissection arms 902 may be adjusted by varying the distance traveled by the pull rod 906 in a proximal direction.

One method of using the dissection device 900 is now described with reference to FIGS. 2A-2F. To begin, the dissection device 900 can first be intravascularly positioned adjacent a treatment site within a blood vessel V (e.g., a vein). The dissection device 900 is then advanced through an opening O (FIG. 2A) in an interior surface IS of the vessel wall W and positioned in a space S (FIGS. 2A and 2B) within the vessel wall W. While positioned within the vessel wall W, the pull rod 906 can be pulled proximally to flex or bend the dissection arms 902 outwardly away from the longitudinal axis of the shaft 904. As the dissection arms 902 move outwardly, the dissection arms 902 push against the tissue at the inner periphery P of the space S, thereby separating the tissue at the periphery to enlarge the space S within the vessel wall W. The dissection arms 902 may continue to expand until a dissection pocket DP (FIG. 2B) having a desired shape and/or size is formed within the vessel wall W. In some embodiments, the dissection device 900 can be repositioned within the dissection pocket DP) and/or collapsed and re-deployed one or more times (while remaining within the dissection pocket DP) until a desired dissection pocket DP configuration is achieved. For example, repositioning the dissection device 900 can include moving the dissection device 900, pull rod 906, and/or shaft 904 axially and/or laterally within the dissection pocket DP, as well as rotating the dissection device 900 about its longitudinal axis within the dissection pocket DP.

Figure 10:
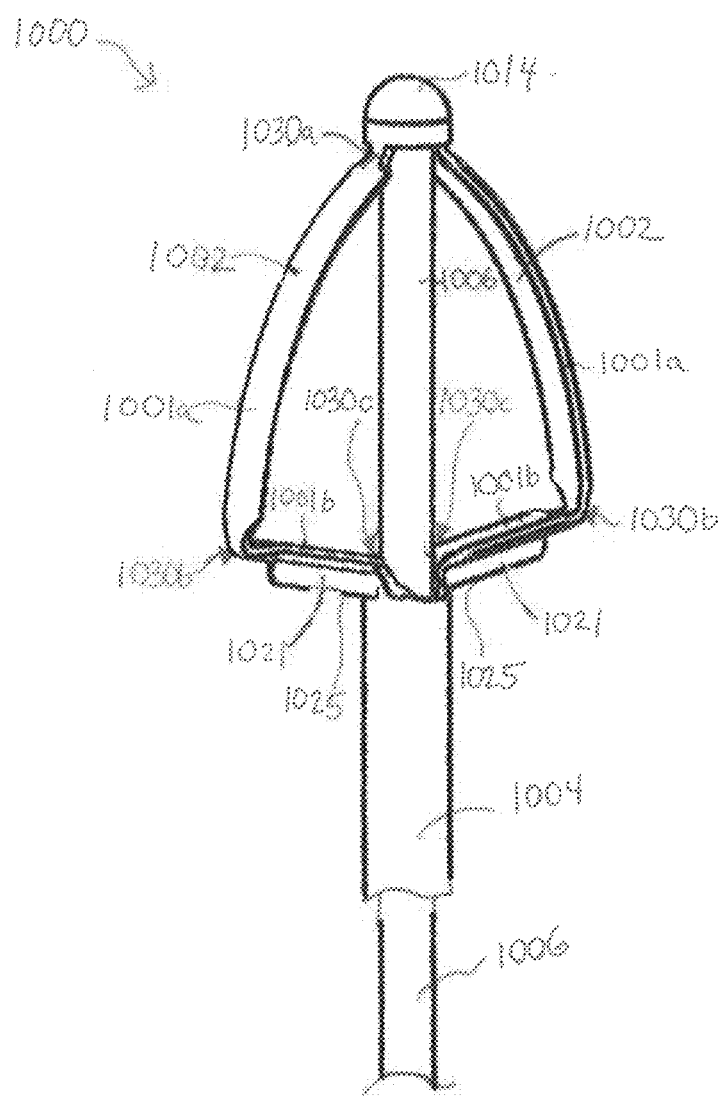
FIG. 10 is an isometric view of another embodiment of a dissection device configured in accordance with the present technology, shown in a deployed state.

FIG. 10 shows another embodiment of a dissection device 1000 configured in accordance with the present technology. The dissection device 1000 can include a shaft 1004, a pull rod 1006, and dissection arms 1002 that are generally similar to the shaft 904, pull rod 906, and dissection arms 902 of the dissection device 900 shown in FIGS. 9A and 9B. For example, the dissection arms 1002 can include two segments 1001 (individually referred to as first and second segments 1001*a*, 1001*b*) and three joints 1030 (referred to individually as first-third joints 1030*a-c*). In contrast to the embodiment shown in FIGS. 9A and 9B, each of the dissection arms 1002 of the dissection device 1000 includes a cutting element 1021 having a sharp edge 1025 configured to cut vessel wall tissue adjacent an opening O in the vessel wall (see FIGS. 2C-2F). For example, the dissection arms 1002 can individually include a blunt or atraumatic dissection surface along the lengths of the second or proximal-most segment 1001*b*, and the cutting element 1021 projects from the respective segment 1001*b* perpendicular to the blunt dissection surface to which it is affixed. In some embodiments, the cutting elements 1021 can project from the surface of the respective dissection arm 1002 a distance of between about 0.2 mm and 2.0 mm. Additionally, the cutting elements 1021 can project a distance of between about 0.5 mm and about 1.5 mm. In a particular embodiment, the cutting element 1021 can project a distance of about 1 mm, or 1 mm.

The individual cutting elements 1021 can extend along all or a portion of the length of the respective second segment 1001*b* and/or dissection arm 1002. In a particular embodiment, a proximal portion of each of the cutting elements 1021 is positioned adjacent to and/or abuts the shaft 1004 when the arms 1002 are in a deployed state. In some embodiments, the cutting elements 1021 can be integral with the dissection arms 1002. In other embodiments, the cutting elements 1021 are separate components attached to the dissection arms 1002. In such embodiments, each of the cutting elements 1021 can be soldered, welded, glued, or otherwise mechanically fixed to the corresponding dissection arm 1002. For example, the proximal segments of the dissection arms 1002 may contain a slot along their respective lengths, and the corresponding cutting element 1021, such as a sharpened blade, can be positioned in the slot and soldered, welded, or otherwise adhered into place. In some embodiments, the sharpened edge of each of the cutting elements 1021 faces away from the respective dissection arm 1002 within a dissection plane defined by the deployed dissection arms 1002. In other embodiments, the dissection device 1000 is configured such that the sharpened portions of the cutting elements 1021 lie in a plane that makes an angle between 0 and 100 degrees with the dissection plane. Moreover, the shape and/or configuration of the dissection arms 1002 and/or cutting elements 1021 can be selected to achieve a desired cutting path of the cutting elements 1021.

In one method of using the dissection device 1000, the dissection device 1000 can be positioned within a space S within a blood and deployed to separate vessel wall tissue and create a dissection pocket DP as detailed above with respect to FIGS. 9A-9B. With reference to FIGS. 2A-2F, the deployed dissection device 1000 can then be pulled proximally within the dissection pocket DP such that the sharpened edges 1025 of the cutting elements 1021 engage and cut tissue at the proximal edge E of the dissection pocket DP, thereby widening the opening O into a mouth M and transforming the dissection pocket DP into a leaflet L (FIGS. 2C-2F). In other embodiments, the cutting elements 1021 can cut the tissue before and/or while the dissection arms 1002 are deployed. If desired, the dissection device 1000 may be repositioned after the dissection pocket DP has been created and before widening the opening O to better position the arms 1002 and/or cutting elements 1021 relative to the opening O. In certain procedures, it may be desirable to collapse and deploy the dissection device 1000 one or more times within the dissection pocket DP (with or without re-positioning the dissection device 1000) and/or pull the cutting elements 1021 proximally one or more times to accomplish a desired dissection pocket DP configuration and/or leaflet L configuration.

FIGS. 11A-11C illustrate another embodiment of a dissection device 1100 configured in accordance with the present technology. FIG. 11A shows the dissection device 1100 in a collapsed or low-profile state, and FIGS. 11B and 11C show the dissection device 1100 in a first deployed state and a second deployed state, respectively. The dissection device 1100 can include an outer sleeve 1150, an elongated shaft 1104 slidably disposed within the outer sleeve 1150, and a pull rod 1106 slidably disposed within the elongated shaft 1104. The pull rod 1106 can have an atraumatic distal end region 1114. The elongated shaft 1104 can have a distal portion 1103, dissection arms 1102 at the distal portion 1103, and a distal end region 1115 coupled to the distal end region 1114 of the pull rod. In the embodiment shown in FIGS. 11A and 11B, one or more regions of the shaft 1104 have been removed along the distal portion 1103 to form the dissection arms 1102. The dissection arms 1102 can be similar to the arms 1002 of the dissection device 1000 shown in FIG. 10, except the arms 1102 have four joints 1130 (referred to individually as first-fourth joints 1130a-1130d) and three segments 1101 (individually labeled first-third segments 1101a-1101c). Additionally, each of the dissection arms 1102 include a cutting element 1121 extending outwardly along a length of the second or intermediate segment 1101b. The cutting element 1121 can have a sharp edge 1125 along all or a portion of its length that is configured to cut vessel wall tissue. In the particular embodiment shown in FIGS. 11A-11C, the third or proximal-most segment 1101c (shown only in FIG. 11C) does not include a cutting element. In other embodiments, the proximal-most segment and/or the third segment 1101c may also include a cutting element.

Figure 2C:
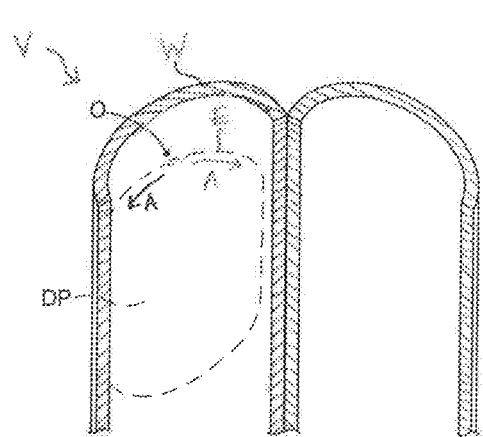
FIG. 2C is a front-elevated, splayed view of the blood vessel in FIGS. 2A and 2B showing a dissection pocket within the blood vessel wall.
Figure 2D:
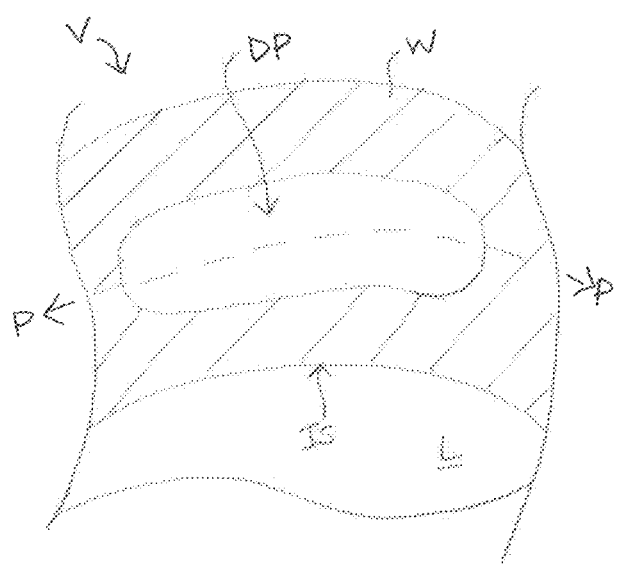
FIG. 2D is a cross-sectional end view of the dissection pocket shown in FIG. 2C.
Figure 2E:
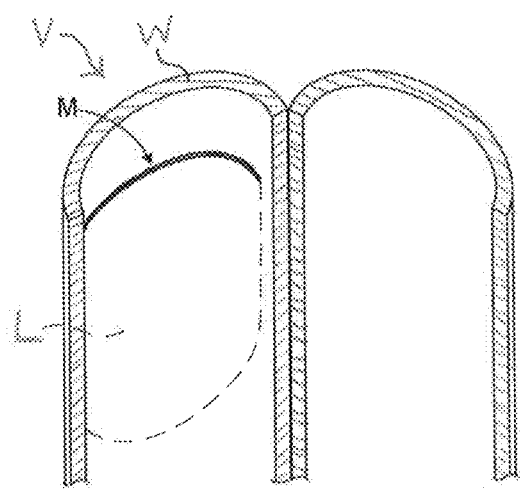
FIG. 2E is a front-elevated, splayed view of the blood vessel in FIGS. 2A-2D, showing a leaflet formed of the blood vessel wall having a mouth.
Figure 2F:
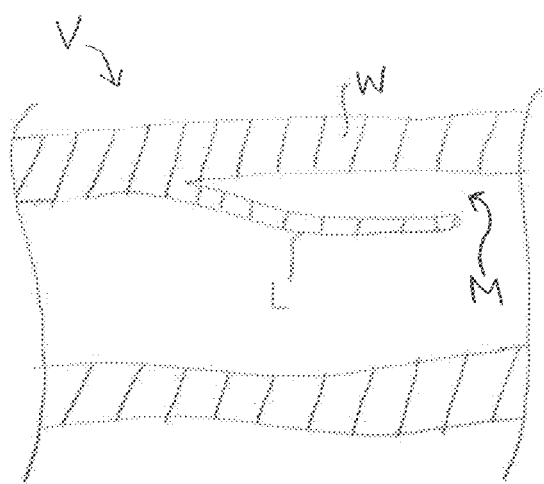
FIG. 2F is a side cross-sectional view showing the leaflet of FIG. 2E.

One method of using the dissection device 1100 will now be described with reference to FIGS. 2A-2F. The dissection device 1100 can be intravascularly positioned adjacent a treatment site within a blood vessel V and advanced through an opening O (FIG. 2A) at an interior surface IS of a blood vessel wall W to be positioned in a space S within the wall W. While positioned in the space S, the dissection device 1100 is configured to (1) transform from the low-profile state (FIG. 11A) to the first deployed state (FIG. 11B) to create a dissection pocket DP within a vessel wall (FIGS. 2C and 2D), and (2) transform from the first deployed state to the second deployed state (FIG. 11C) to widen the opening O (FIGS. 2C-2F) into a mouth M (FIGS. 2E and 2F), thereby transforming the dissection pocket DP into a leaflet L (FIGS. 2E and 2F). To transform the dissection arms 1102 from the low-profile state to the first deployed state, the pull rod 1106 is pulled proximally relative to the outer sleeve 1150 and shaft 1104 (as indicated by arrow A1), thereby forcing the arms 1102 to flex or bend outwardly away from the longitudinal axis of the shaft 1104 such that the sharp edges 1125 of the cutting elements 1121 along the second segments 1101b face proximally. As the pull rod 1106 is pulled proximally, the outer sleeve 1150 remains positioned over the proximal-most or third segments 1101c of the arms 1102, thereby preventing the third segments 1101c from deploying. Accordingly, proximal movement of the pull rod 1106 only deploys the non-constrained first and second segments 1101a, 1101b. As such, the resulting dissection pocket DP (FIGS. 2C and 2D) can have a shape defined by an outline of only the first and second segments 1101a, 1101b.

After forming the dissection pocket DP having a desired shape and size, the outer sleeve 1150 can be retracted as indicated by arrow A2 (FIG. 11C) to fully deploy the third or proximal-most segments 1101c, thereby transforming the dissection device 1100 from the first deployed state to the second deployed state. Releasing the third segments 1101c from the outer sleeve 1150 causes the proximal ends of the second segments 1101b to swing outwardly away from the longitudinal axis of the shaft 1104 such that a longitudinal dimension of the second segments 1101b are generally parallel to a longitudinal dimension of the pull rod 1106 and the sharp edges 1125 of the cutting elements 1121 face laterally away from a longitudinal axis of the shaft 1104. For example, the shaft 1104 and/or arms 1102 can be made of a superelastic and/or shape memory material (e.g., Nitinol) that is heat set during manufacturing to form a predetermined deployed shape. As the second segments 1101b move away from the shaft 1104, the sharp edges 1125 of the cutting elements 1121 engage the vessel wall tissue surrounding the opening O and cut the tissue laterally away from either side of the opening O along the proximal edge E of the dissection pocket DP (see arrows A in FIG. 2C), thereby widening the opening O into a mouth M (FIGS. 2E and 2F) to transform the dissection pocket DP into a leaflet L. If desired, the dissection device 1100 may be repositioned after the dissection pocket DP has been created and before widening the opening O to better position the arms 1102 and/or cutting elements 1102 relative to the opening O.

In certain procedures, it may be desirable to transition back and forth between the first deployed state and the second deployed state (with or without re-positioning the dissection device 1100) to accomplish a desired dissection pocket DP and/or leaflet L configuration. To transform the dissection device 1100 from the second deployed state to the first deployed state, a clinician can (1) push the pull rod 1106 distally while holding the shaft 1104 and the outer sleeve 1150 stationary relative to the pull rod 1106 to force the dissection arms 1102 to collapse towards the pull rod 1106, (2) advance the outer sleeve 1150 distally over the third segments 1101c, and (3) pull the pull-rod 1106 distally to re-deploy the first and second segments 1101a, 1101b of the arms 1102.

In some embodiments, the dissection device 1100 does not include an outer sleeve 1150. In such embodiments, the third or proximal-most segments 1101b of the dissection arms 1102 are non-constrained or otherwise free to bend outwardly away from the longitudinal axis of the shaft 1104 as the pull rod 1106 is moved proximally relative to the shaft 1104. Accordingly, the dissection device 1100 transitions directly from the low-profile state of FIG. 11A to the deployed state shown in FIG. 11C, thereby (1) enlarging the space S (FIGS. 2A-2B) to form a dissection pocket DP (FIGS. 2C-2D) and (2) widening the opening O (cutting tissue outwardly) to form the mouth M in a single step.

FIGS. 12A-12C illustrate another embodiment of a dissection device 1200 configured in accordance with the present technology, shown in a first, second, and third deployed state, respectively. The dissection device 1200 can include an outer sleeve 1250, an elongated shaft 1204 slidably disposed within the outer sleeve 1250, an inner shaft 1240 slidably disposed within the elongated shaft 1204, and a pull rod 1206 slidably disposed within the inner shaft 1240. The pull rod 1206 can have an atraumatic distal end region 1214. The elongated shaft 1204 can have a distal portion 1203, dissection arms 1202 at the distal portion 1203, and a distal end region 1215 coupled to the distal end region 1215 of the pull rod 1206. In the embodiment shown in FIGS. 12A and 12B, one or more regions of the shaft 1204 at the distal portion 1203 have been removed to form the arms 1202. In other embodiments, the arms 1202 can be separate components coupled to the shaft 1204 at the distal portion 1203. The arms 1202 can be similar to the arms 1102 of the dissection device 1000 shown in FIGS. 11A-11C. For example, the arms 1202 can include four joints 1230 (referred to individually as first-fourth joints 1230a-1230d) and three segments 1201 (individually labeled first-third segments 1201a-1201c). Additionally, each of the arms 1202 include a cutting element 1221 extending outwardly along a length of the second or intermediate segment 1201b.

In the embodiment shown in FIGS. 12A-12C, the inner member 1140 includes two pairs of struts 1242 (only one pair visible in FIGS. 12A-12C) configured to pivot about the inner shaft 1240. Each of the struts 1242 can have a distal portion 1244 coupled to the inner shaft 1240 and a proximal portion 1246 (FIG. 12C) coupled to a respective arm 1202. In the illustrated embodiment of the dissection device 1200, the proximal portion 1246 of each of the struts 1242 is fixed to a respective third joint 1230c. In some embodiments, the proximal portion 1246 of each of the struts 1242 includes a tab configured to mate with a slot on a corresponding dissection arm 1202. In other embodiments, the struts 1242 can be coupled to the dissection arms 1202 via other suitable mechanical coupling devices.

In use, the dissection device 1200 is configured to: (1) transform from the low-profile state (not shown) to the first deployed state (FIG. 12A) to create a dissection pocket DP within a vessel wall V (FIGS. 2C and 2D), (2) transform from the first deployed state to the second deployed state (FIG. 12B), and (3) transform from the second deployed state to the third deployed state (FIG. 12C) to widen the opening O into a mouth M (FIGS. 2C-2F), thereby transforming the dissection pocket DP into a leaflet L (FIGS. 2E and 2F). To transform the dissection arms 1202 from the low-profile state to the first deployed state, the pull rod 1206 is pulled proximally relative to the outer sleeve 1250, the shaft 1204, and the inner member 1240 (as indicated by arrow A1 in FIG. 12A), thereby forcing the arms 1202 to bend outwardly away from the longitudinal axis of the shaft 1204. The outer sleeve 1250 remains positioned over the proximal-most or third segments 1201c of the arms 1202 as the pull rod 1206 moves proximally, thereby preventing the third segments 1201c from deploying. Accordingly, only the non-constrained first and second segments 1201a, 1201b deploy to form the dissection pocket DP within the vessel wall.

After forming the dissection pocket DP having a desired geometry, the outer sleeve 1250 can be retracted as indicated by arrow A2 (FIG. 12B) to expose the proximal-most or third segments 1101c, thereby transforming the dissection device 1200 from the first deployed state to the second deployed state. Once the third segments 1201c have been exposed, the inner shaft 1240 can be pulled proximally as indicated by arrow A3 (FIG. 12C) relative to the pull rod 1206 and shaft 1204. As the inner shaft 1204 moves proximally, the proximal portion 1246 of the struts 1242 extend away from the longitudinal axis of the inner shaft 1240 and push the third joints 1230c outwardly. Pushing the third joints 1230c outwardly swings the cutting elements 1221 laterally away from the longitudinal axis of the inner shaft 1240 to engage and cut the vessel wall tissue adjacent the opening O, thereby widening the opening O into a mouth M (FIGS. 2C-2F) to create a leaflet L from the dissection pocket DP. If desired, the dissection device 1200 may be repositioned after the dissection pocket DP has been created and before widening the opening O to better position the arms 1202 and/or cutting elements 1221 relative to the opening O.

In certain procedures, it may be desirable to transition back and forth between the first, second, and/or third deployed states (with or without re-positioning the dissection device 1200) to accomplish a desired dissection pocket DP and/or leaflet L configuration. To transform the dissection device 1200 from the third deployed state to the second deployed state, a clinician can push the inner shaft 1240 distally while holding the shaft 1204, outer sleeve 1250, and pull rod 1206 stationary relative to the inner shaft 1240 to force the proximal portions 1246 of the struts 1242 to collapse towards the inner shaft 1240. To transform the dissection device 1200 from the second deployed state to the first deployed state, a clinician can advance the outer sleeve 1250 distally over the third segments 1202c.

In some embodiments, the dissection device 1200 does not include the outer sleeve 1250, and the third segments 1202c remain exposed as the pull rod 1206 is retracted to deploy the first and second segments 1202a-b. In such embodiments, the dissection device 1200 transitions directly from the low-profile state of FIG. 12A to the deployed state shown in FIG. 12C, thereby (1) enlarging the space S (FIGS. 2A-2B) to form a dissection pocket DP (FIGS. 2C-2D) and (2) widening the opening O (cutting tissue outwardly) to form the mouth M in a single step. It will be appreciated that, regardless of whether the arms 1202 are configured to bend away from the shaft 1204 automatically or with the help of the struts 1242, it may be beneficial to include the struts 1242 as an additional deployment option and/or to fortify one or more of the joints 1230. Moreover, although the dissection device 1200 described with reference to FIGS. 12A-12C includes two pairs of struts 1242 (four struts total), in other embodiments the dissection device 1200 can include more or fewer total struts 1242 and/or more or fewer struts 1242 per arm 1202 (e.g., one strut 1242 per arm 1202, etc.).

Figures 13A, 13B:
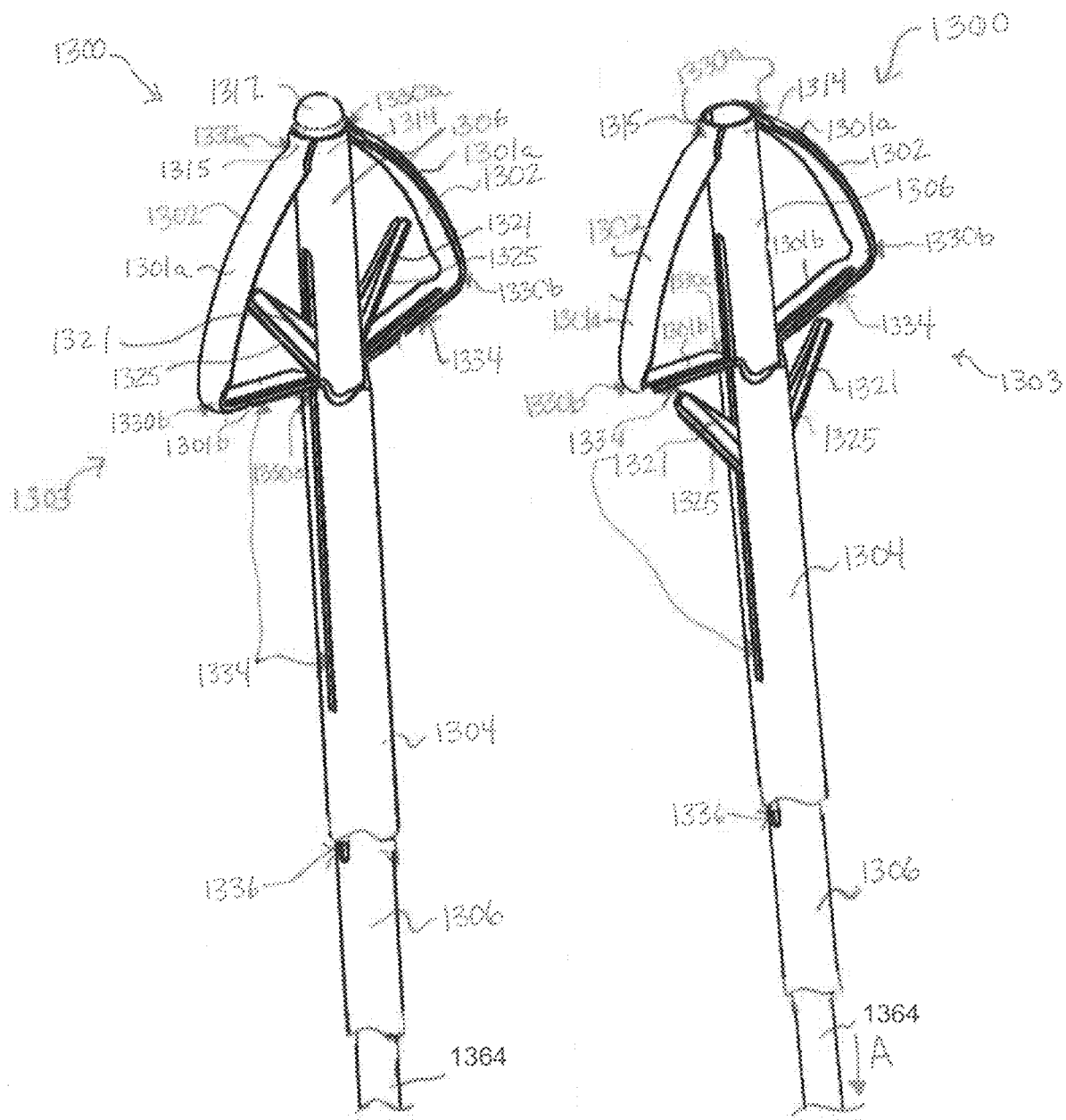
FIGS. 13A and 13B are isometric views of another embodiment of a dissection device configured in accordance with the present technology, shown during various stages of deployment.

In some embodiments of the present technology, the dissection device can include a separate cutting device. For example, FIGS. 13A and 13B show one embodiment of a dissection device 1300 configured in accordance with the present technology that is configured to receive a separate cutting device 1360 (only a portion shown in FIGS. 13A and 13B). FIGS. 13A and 13B show the dissection device 1300 in distal and proximal deployed states, respectively. The dissection device 1300 includes an elongated shaft 1304 and a pull member 1306 slidably disposed within the shaft 1304. The pull member 1306 can be a hollow tubular structure having a distal end region 1314, and the cutting device 1360 can be configured to be slidably disposed within a lumen of the pull member 1306. The elongated shaft 1304 can have a distal portion 1303, dissection arms 1302 at the distal portion 1303, and a distal end region 1315 coupled to the distal end region 1314 of the pull member 1306.

In the embodiment shown in FIGS. 13A and 13B, one or more regions of the shaft 1304 at the distal portion 1303 have been removed to form the dissection arms 1302. As such, the dissection arms 1302 can be continuous and/or integral with the shaft 1304. In other embodiments, dissection arms 1302 can be separate components coupled to the distal portion 1303 of the shaft 1304. The arms 1302 can include three joints 1330 (referred to individually as first-third joints 1330a-1330c) and two segments 1301 (individually labeled first and second segments 1301a, 1301b).

The elongated shaft 1304 can further include two slots 1334 along at least a portion of its length. (Only one slot 1334 is visible in FIGS. 13A and 13B.) In some embodiments, the slots 1334 can be positioned at circumferentially opposing portions of the shaft 1304. In other embodiments, the slots 1334 can have other suitable spacing about the circumference of the shaft 1304. In the embodiment shown in FIGS. 13A and 13B, each of the slots 1334 extend distally along the shaft 1304 to the second or proximal-most segment 1301b of a respective arm 1302. In other embodiments, the slots 1334 may extend to other locations along the shaft 1304 and/or corresponding arm 1302, such as a location distal to the second or proximal-most segment 1301b.

The pull member 1306 can also include two slots 1336 along at least a portion of its length. (Only portions of one slot are visible in FIGS. 13A and 13B.) In some embodiments, the slots 1336 can be positioned at circumferentially opposing portions of the pull member 1306. In other embodiments, the slots 1336 can have other suitable spacing about the circumference of the pull member 1306. In the embodiment shown in FIGS. 13A and 13B, each of the slots 1336 extend distally along the pull member 1306 to a location that is distal to a portion of the pull member 1306 longitudinally aligned with a proximal end of the corresponding arm 1302 in the deployed state. The pull member 1306 can be positioned within the shaft 1304 such that the slots 1336 along the pull member 1306 circumferentially align with the slots 1334 along the shaft 1304.

Figure 13C:
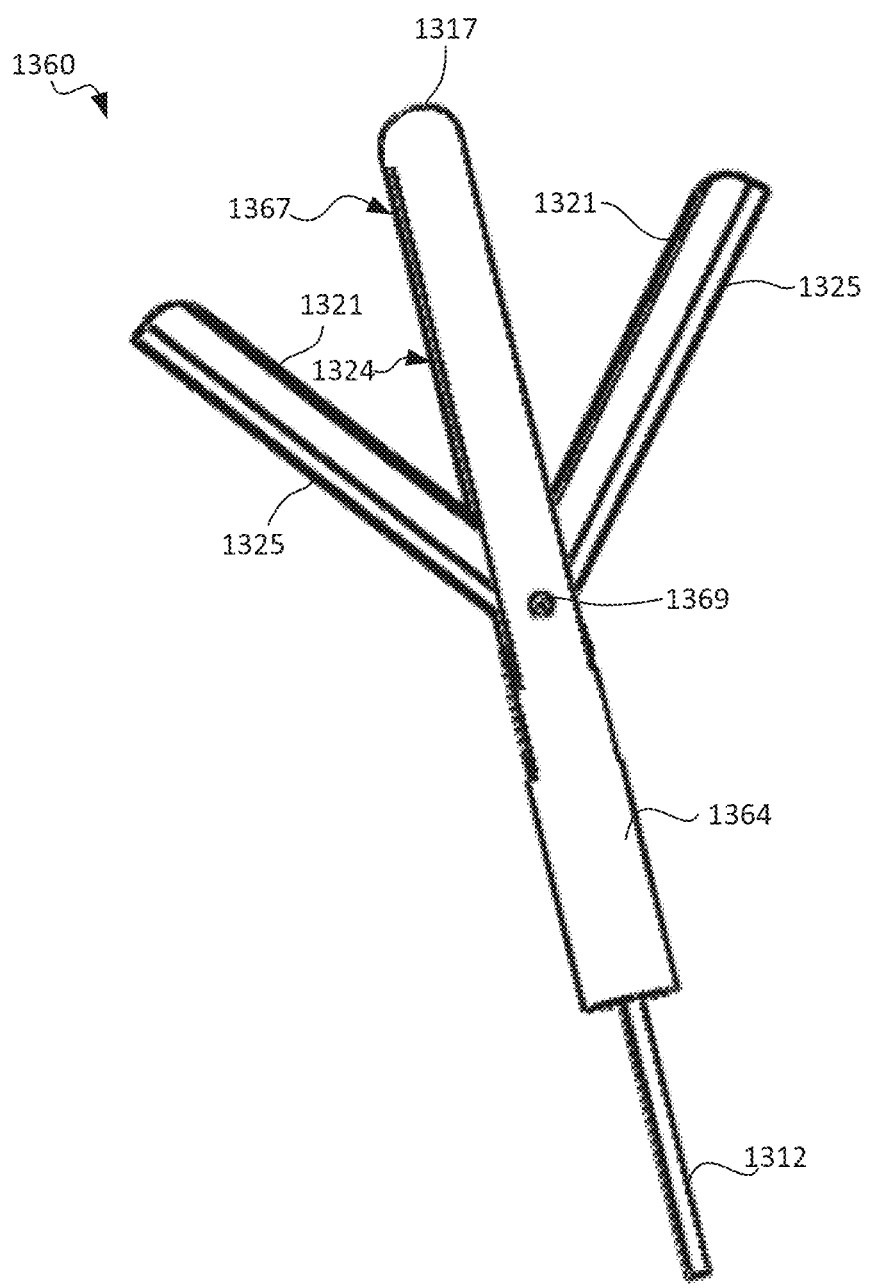
FIG. 13C is an isometric view of a cutting device configured for use with the dissection devices of the present technology.

FIG. 13C is an isolated view of the cutting device 1360. The cutting device 1360 can include an elongated shaft 1364, two cutting elements 1321 coupled to a distal region of the shaft 1364, and an actuator 1312 extending through at least a portion of the shaft 1364. Each of the cutting elements 1321 can have a sharp edge 1325 configured to cut vessel wall tissue. The elongated shaft 1364 can further include an aperture 1367 at its distal region, and can terminate distally at a rounded or atraumatic distal tip portion 1317 (also visible in FIG. 13A). The aperture 1367 can have lateral openings 1324 (only one visible in FIG. 13C). The cutting elements 1321 can be rotatably coupled to the shaft 1364 by a first linkage 1369 and configured to pivot or rotate about the first linkage 1369 between a low-profile or collapsed state (not shown) and a deployed state in which the cutting elements 1321 extend outwardly away from a longitudinal axis of the shaft 1364 in a distal direction. In the embodiment shown in FIG. 13C, the first linkage 1369 is a pin that extends from the elongated shaft 1364 across the aperture 1367 through a slot in each of the cutting elements 1321. In other embodiments, the cutting elements 1321 can be coupled to the shaft 1364 by other suitable mechanical linkages. The cutting elements 1321 can be coupled to a distal portion of the actuator 1312 by a second linkage (not visible in FIG. 13C). In the embodiment shown in FIG. 13C, the second linkage is a pin that extends from the actuator 1312 through a thickness of each of the cutting elements 1321. In other embodiments, the cutting elements 1321 can be coupled to the actuator 1312 by other suitable mechanical linkages. The first linkage 1369 can be fixed relative to the elongated shaft 1364, while the second pin can move axially relative to the shaft 1364.

In the low-profile state (not shown), the cutting elements 1321 can be generally aligned with the elongated shaft 1364 such that the majority of each cutting element 1321 lies within the lateral boundaries of the elongated shaft 1364. In some embodiments, each of the cutting elements 1321 in their entireties lies within the lateral boundaries of the elongated shaft 1364. Moreover, in the low-profile state, a portion of each slot (not shown) in the cutting elements 1321 can be aligned. To deploy the cutting device 1360, the actuator 1312 can be pushed distally (e.g., from the proximal portion), thereby urging the cutting elements 1321 in a distal direction. As the cutting elements 1321 are urged distally, the individual slots slide along the first linkage 1369, thereby forcing the cutting elements 1321 to rotate based on the shape of each slot (similar to the mechanism of action detailed with respect to FIGS. 3A-3D). As the cutting elements 1321 rotate, they extend laterally through the openings 1324 in the elongated shaft 1364. In other embodiments, the cutting device 1360 can be configured such that proximal movement of the actuator 1312 can deploy the cutting elements 1321.

The cutting device 1360 can be positioned within the pull member 1306 such that the cutting elements 1321 are circumferentially aligned with the slots 1334, 1336 along the shaft 1304 and pull member 1306, respectively. Accordingly, when the cutting elements 1321 are in the deployed state, the cutting elements 1321 extend outwardly through the slots 1334, 1336 away from the longitudinal axis of the shaft 1364. The cutting elements 1321 can extend from the shaft 1364 in a distal direction such that the cutting elements 1321 are angled with respect to the longitudinal axis of the shaft 1364. In the embodiment shown in FIGS. 13A and 13B, the sharp edges 1325 of the cutting elements 1321 face proximally when the cutting elements 1321 are in a deployed state. In other embodiments, the sharp edges 1325 can face distally when the cutting elements 1321 are in a deployed state.

One method of using the dissection device 1300 will now be described with reference to FIGS. 2A-2F. The dissection device 1300 is first advanced through an opening O in a vessel wall W and positioned within an access space S (FIGS. 2A and 2B). The pull member 1306 can be pulled proximally relative to the elongated shaft 1304 and the cutting device shaft 1364 to bend the arms 1302 away from the longitudinal axis of the shaft 1304 to form a dissection pocket DP (FIGS. 2C and 2D). The cutting device 1360 can then be advanced and/or otherwise positioned within the pull member 1306 in a low-profile state (not shown) such that the cutting elements 1321 are adjacent a distal portion of the slot 1336. The cutting device 1360 is then actuated to pivot the cutting elements 1321 into the deployed state, away from the longitudinal axis of the pull member 1306. As shown in FIG. 13A, the cutting elements 1321 can deploy within an interior region defined by the deployed arms 1302 (e.g., within the dissection pocket DP). The shaft 1364 of the cutting device 1360 can then be pulled proximally relative to the shaft 1304 and the pull member 1306 to pull the cutting elements 1321 through the slots 1334 along the second or proximal-most segments 1301b of the dissection arms 1302. As the cutting elements 1321 pass through the slots 1334 in the respective arms 1302, all or a portion of the length of each sharp edge 1325 engages and cuts tissue adjacent the opening O in the vessel wall W to form a mouth M (FIGS. 2C-2F). In some embodiments, the degree of rotation of the cutting elements 1321 and/or the angle at which the cutting elements 1321 extend from the shaft 1364 can be adjusted depending on the length or shape of the mouth M desired. Likewise, the distance the shaft 1364 is pulled proximally can also be varied to achieve a desired length or shape of the mouth M.

FIGS. 14A and 14B are isometric views of another embodiment of a dissection device 1400 configured in accordance with the present technology, shown at various stages of deployment. The dissection device 1400 can be generally similar to the dissection device 1300 shown in FIGS. 13A and 13B. For example, the dissection device 1400 can include an elongated shaft 1404, dissection arms 1402, a pull member 1406, a cutting device 1460, and cutting elements 1421 similar to the shaft 1304, arms 1302, pull member 1306, cutting device 1360, and cutting elements 1321 respectively, of FIGS. 13A and 13B. The cutting device 1460 of the dissection device 1400 of FIGS. 14A and 14B, however, is configured such that, when the cutting elements 1421 are in the deployed state, the cutting elements 1421 extend outwardly from the pull member 1406 in a distal direction such that the cutting elements 1421 are angled with respect to the longitudinal axis of the pull member 1406. In the embodiment shown in FIGS. 14A and 14B, the cutting elements 1421 include sharp edges 1425 that face proximally when the cutting elements 1421 are in a deployed state. In other embodiments, the sharp edges 1425 can face distally when the cutting elements 1421 are in a deployed state.

Figure 14C:
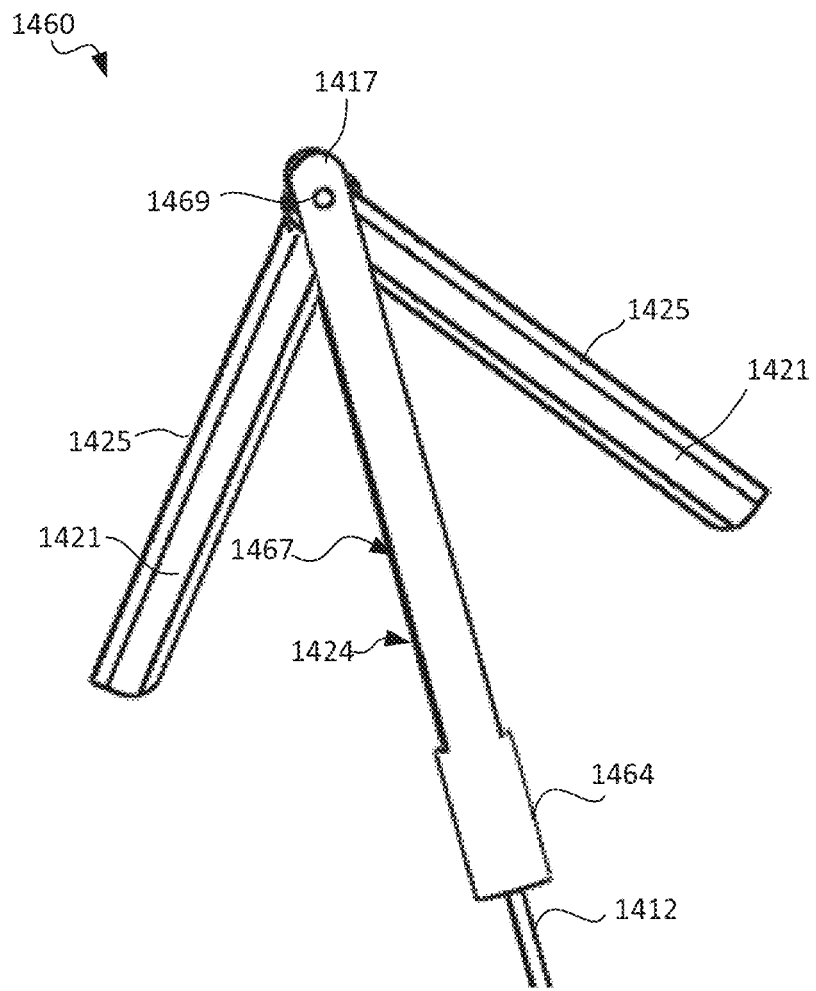
FIG. 14C is an isometric view of a cutting device configured for use with the dissection devices of the present technology.

FIG. 14C is an isolated view of a variation of the cutting device 1460 shown in FIGS. 14A and 14B. The cutting device 1460 can include an elongated shaft 1464, two cutting elements 1421 coupled to a distal region of the shaft 1464, and an actuator 1412 (not shown in FIGS. 14A and 14B) extending through at least a portion of the shaft 1464. Each of the cutting elements 1421 can have a sharp edge 1425 configured to cut vessel wall tissue. The elongated shaft 1464 can further include an aperture 1467 at its distal region, and can terminate distally at a rounded or atraumatic distal tip portion 1417 (also visible in FIG. 14B). The aperture 1467 can have lateral openings 1424 (only one visible in FIG. 14C). The cutting elements 1421 can be rotatably coupled to the shaft 1464 by a first linkage 1469 positioned at or near a distal end of the shaft 1464. The cutting elements 1421 can be configured to pivot or rotate about the first linkage 1469 between a low-profile or collapsed state (not shown) and a deployed state in which the cutting elements 1421 extend outwardly away from a longitudinal axis of the shaft 1464. In the embodiment shown in FIGS. 14A and 14B, the cutting elements 1421 extend outwardly perpendicular to the shaft 1404 and/or slightly in a distal direction, while in FIG. 14C, the cutting elements 1421 extend outwardly away from the shaft 1464 in a proximal direction. However, in the embodiment shown in FIGS. 14A and 14B and the embodiment shown in FIG. 14C, the sharp edges 1425 faces in a distal direction when the cutting elements 1421 are in a deployed state.

In the embodiment shown in FIG. 14C, the first linkage 1469 is a pin that extends from the elongated shaft 1464 across the aperture 1467 through a slot in each of the cutting elements 1421. In other embodiments, the cutting elements 1421 can be coupled to the shaft 1464 by other suitable mechanical linkages. The cutting elements 1421 can be coupled to a distal portion of the actuator 1412 by a second linkage (not visible in FIG. 14C). In the embodiment shown in FIG. 14C, the second linkage is a pin that extends from the actuator 1412 through a thickness of each of the cutting elements 1421. In other embodiments, the cutting elements 1421 can be coupled to the actuator 1412 by other suitable mechanical linkages. The first linkage 1469 can be fixed relative to the elongated shaft 1464, while the second pin can move axially relative to the shaft 1464.

In the low-profile state (not shown), the cutting elements 1421 can be generally aligned with the elongated shaft 1464 such that the majority of each cutting element 1421 lies within the lateral boundaries of the elongated shaft 1464. In some embodiments, each of the cutting elements 1421 in their entireties lies within the lateral boundaries of the elongated shaft 1464. Moreover, in the low-profile state, a portion of each slot (not shown) in the cutting elements 1421 can be aligned. To deploy the cutting device 1460, the actuator 1412 can be pushed distally (e.g., from the proximal portion), thereby urging the cutting elements 1421 in a distal direction. As the cutting elements 1421 are urged distally, the individual slots slide along the first linkage 1469, thereby forcing the cutting elements 1421 to rotate based on the shape of each slot (similar to the mechanism of action detailed with respect to FIGS. 3A-3D). As the cutting elements 1421 rotate, they extend laterally through the openings 1424 in the elongated shaft 1464. In other embodiments, the cutting device 1460 can be configured such that proximal movement of the actuator 1412 can deploy the cutting elements 1421.

The cutting device 1460 can be positioned within the pull member 1406 such that the cutting elements 1421 are circumferentially aligned with the slots 1434, 1436 along the shaft 1404 and pull member 1406, respectively. Accordingly, when the cutting elements 1421 are in the deployed state, the cutting elements 1421 extend outwardly through the slots 1434, 1436 away from the longitudinal axis of the shaft 1464. The cutting elements 1421 can extend from the shaft 1464 in a distal direction such that the cutting elements 1421 are angled with respect to the longitudinal axis of the shaft 1464. In the embodiment shown in FIGS. 14A and 14B, the sharp edges 1425 of the cutting elements 1421 face proximally when the cutting elements 1421 are in a deployed state. In other embodiments, the sharp edges 1425 can face distally when the cutting elements 1421 are in a deployed state.

In one method of use, the dissection device 1400 can be advanced through an opening O in a vessel wall W and positioned within an access space S (FIG. 2A). The pull member 1406 can be pulled proximally relative to the elongated shaft 1204 and the cutting device shaft 1464 to bend the arms 1402 away from the longitudinal axis of the shaft 1404 and separate tissue within the vessel wall to form a dissection pocket DP (FIG. 2B). The cutting device 1460 can then be advanced and/or otherwise positioned within the pull member 1406 in a low-profile state (not shown) such that the cutting elements 1421 are adjacent a portion of the slots 1434, 1436 that are proximal to the second or proximal-most segments 1401b of the dissection arms 1402 in the deployed state. The members 1423 of the cutting device 1460 can then be actuated to rotate or pivot the cutting elements 1421 into the deployed state, away from the longitudinal axis of the pull member 1406. As shown in FIG. 14A, the cutting elements 1421 can deploy outside of an interior region defined by the deployed arms 1402 (e.g., outside the dissection pocket DP). The shaft 1464 of the cutting device 1460 can then be pushed distally relative to the shaft 1404 and the pull member 1406 (indicated by arrow A in FIG. 14B) to push the cutting elements 1421 through the slots 1434 along the second or proximal-most segments 1401b of the dissection arms 1402. As the cutting elements 1421 pass through the slots 1434 in the respective arms 1402, all or a portion of the length of each sharp edge 1425 engages tissue along the proximal edge E the dissection pocket DP (FIGS. 2C-2D) from outside the dissection pocket DP, while the second or proximal-most segments 1401b of the dissection arms 1402 support tissue at or adjacent the proximal edge E from inside the dissection pocket DP. Each of the sharp edges 1425 move distally through the slots 1434 and cut the tissue extending laterally from the opening O, thereby forming a mouth M (FIGS. 2C-2F). In some embodiments, the degree of rotation of the cutting elements 1421 and/or the angle at which the cutting elements 1421 extend from the shaft 1464 can be adjusted depending on the length or shape of the mouth M desired. Likewise, the distance the shaft 1464 is pulled proximally can also be varied to achieve a desired length or shape of the mouth M.

FIGS. 15A and 15B illustrate a further embodiment of a dissection device 1500 configured in accordance with another embodiment of the present technology. FIGS. 15A and 15B show the dissection device 1500 in a low-profile state and a deployed state, respectively. The dissection device 1500 can include an outer shaft 1551 and an inner shaft 1504 slidably disposed within the outer shaft 1504. The outer shaft 1551 can have a distal portion 1553 and two longitudinal slots 1555 (only one visible in FIGS. 15A and 15B) extending along a length of the distal portion 1553. The inner shaft 1504 can have a distal portion 1503, dissection arms 1502 at the distal portion 1502, and a tapered distal region 1513. In the embodiment shown in FIGS. 15A and 15B, one or more regions of the inner shaft 1504 have been removed at the distal portion 1503 to form the dissection arms 1502.

The inner shaft 1504 and the outer shaft 1551 can be coupled at their respective distal regions, and the inner shaft 1504 can be positioned within the outer shaft 1551 such that the dissection arms 1502 circumferentially align with the slots 1553 in the outer shaft 1551. Proximal movement of the outer shaft 1551 with respect to inner shaft 1504 (as indicated by arrow A in FIG. 15B) pulls the distal portions of the dissection arms 1502 proximally and forces the dissection arms 1502 to bend outwardly away from the longitudinal axis of the inner shaft 1504 through the respective slots 1555 in the outer shaft 1551.

Because the dissection device 1500 does not include a pull member, a central lumen of the shaft 1504 can be used to house and/or deliver one or more additional devices, such as, for example, a separate cutting device (e.g., the cutting device 1360 of FIGS. 13A and 13B, the cutting device 1460 of FIGS. 14A and 14B, etc.), an inner dilator and/or a guide member (e.g., a guide wire, a guide needle, etc.). For example, in some embodiments, the dissection device 1500 can be positioned over an inner dilator and/or guide member and advanced to a desired dissection location within a vessel wall. Once the dissection device 1500 is positioned, the inner dilator and/or guide member may be withdrawn and replaced with a cutting device (e.g., the cutting device 1360 of FIGS. 13A and 13B, the cutting device 1460 of FIGS. 14A and 14B, etc.). In such embodiments, the cutting device can include a distal portion configured to mate with a distal portion of the dissection device (e.g., via a spring latch, a press fit, a screw fit, etc.). Accordingly, proximal movement of the cutting device relative to the inner and outer shafts 1504, 1551 of the dissection device 1504 can deploy the dissection arms 1502. In other embodiments, the dissection device 1504 does not include an outer shaft 1551.

FIGS. 16A and 16B show another embodiment of a dissection device 1600 configured in accordance with the present technology. The dissection device 1600 can include an elongated shaft 1604, a pull rod 1606 slidably disposed within the elongated shaft 1604, and a separate cutting device 1660 configured to be slidably disposed over at least a portion of the shaft 1604. In some embodiments, the cutting device 1660 may be positioned between shaft 1604 and pull rod 1606. The pull rod 1606 can have an atraumatic distal end region 1614. The shaft 1604 can have a distal portion 1603 (FIG. 16A), dissection arms 1602 at the distal portion 1603, and a distal end region 1615 coupled to the distal end region 1614 of the pull rod 1606. In the embodiment shown in FIGS. 16A and 16B, one or more regions of the shaft 1604 have been removed along the distal portion 1603 to form the dissection arms 1602. In other embodiments, the dissection arms 1602 can be separate components coupled to the shaft 1604. Proximal movement of the pull rod 1606 with respect to the elongated shaft 1604 pulls the distal portions of the dissection arms 1602 proximally and forces the dissection arms 1602 to bend outwardly away from the longitudinal axis of the shaft 1604, as shown in FIGS. 16A and 16B.

The dissection arms 1602 can include one or more segments 1601 (referred to individually as first-third segments 1601 a-c) and one or more joints 1630 (referred to individually as first-fourth joints 1630a-d) configured to preferentially flex relative to the segments 1601 and/or the shaft 1604. The elongated shaft 1604 can further include two slots 1634 along at least a portion of its length. In some embodiments, the slots 1634 can be positioned at circumferentially opposing portions of the shaft 1604. In other embodiments, the slots 1634 can have other suitable spacing about the circumference of the shaft 1604. In the embodiment shown in FIGS. 16A and 16B, each of the slots 1634 extend distally along the shaft 1604 to the second segment 1601b of the corresponding arm 1602. In other embodiments, the slots 1634 may extend to other locations along the shaft 1604 and/or corresponding arm 1602, such as a location distal or proximal to the second segment 1601b.

FIG. 17 is an isolated view of the cutting device 1660. The cutting device 1660 can include an elongated shaft 1664 (only a portion shown) configured to be positioned over the shaft 1604. The shaft 1664 can have a bifurcated distal portion 1663. The bifurcations of the distal portion 1663 can form two arms 1662. In other embodiments, the arms 1662 are separate components coupled to the shaft 1664 via a hinge joint, a solder, a weld, or other suitable attachment means. In a particular embodiment, the arms 1662 can include one or more joints (not shown) along their lengths (e.g., at a proximal end portion) that bias the arms 1662 to preferentially flex when deployed.

The cutting device 1660 can be positioned over the shaft 1604 such that the arms 1662 circumferentially align with the dissection arms 1602. Each of the arms 1662 can include a coupling element 1672, such as a tab or protrusion, that extends around at least a portion of the circumference of the respective dissection arm 1602, thereby securing each of the arms 1662 to a respective dissection arm 1602 and ensuring that a cutting element 1621 of the arms 1662 extends through the slot 1634 in the respective dissection arm 1602. Each of the coupling elements 1672 can be configured to slide along at least a portion of the respective dissection arm 1602. In other embodiments, the coupling elements 1672 can be a component of the dissection arms 1602, and in yet other embodiments, the coupling elements 1672 are separate components from both the cutting device 1660 and the dissection arms 1602.

As shown in FIG. 17, each of the arms 1662 can include a cutting element 1621, such as a sharpened blade. For example, in the embodiment shown in FIG. 17, each of the arms 1662 has a slot 1665 along a portion of its respective distal region, and the corresponding cutting element 1621 is fixed within the slot 1665 (e.g., via soldering, welding, glue, a press fit, etc.). In other embodiments, one or more of the cutting elements 1621 can be integral with the arms 1662. In a deployed state, the cutting elements 1621 can extend distally from the shaft 1664 at an angle. Each of the cutting elements 1621 can have a sharp edge 1625 configured to cut vessel wall tissue. The cutting elements 1621 can be positioned such that, when the cutting device 1660 is in a low-profile state, the sharp edges 1625 face radially inwardly.

The cutting device 1660 can be positioned over the shaft 1604 such that the arms 1602 and/or cutting elements 1621 circumferentially align with the slots 1634 along the shaft 1604. Accordingly, in use the cutting device 1660 can be pushed distally over the shaft 1604. As the arms 1662 are advanced distally over the deployed arms 1602, the arms 1662 are forced to bend outwardly away from the longitudinal axis of the shaft 1664 to conform to the deployed shape of the third or proximal-most segment 1601c of the dissection arms 1602. The sharp edge 1625 of the cutting element 1621 slides along the slot 1634 in the respective arm 1602 and projects through the slot 1634 to engage and cut vessel wall tissue.

FIGS. 18-20 are side views of cutting devices having different cutting elements configured in accordance with the present technology. For example, FIG. 18 shows a cutting device 1860 having arms 1862 and a cutting element 1821 coupled to each arm 1862. Each cutting element 1821 has a curved sharp edge 1825. The distance which the cutting element 1821 extends from the arm 1862 varies along the length of the cutting element 1821. FIG. 19 illustrates another embodiment of a cutting device 1960 having arms 1962 and a cutting element 1921 coupled to each arm 1962. Each cutting element 1921 can include a leading point and a sharp edge 1925 that faces distally. The cutting element 1921 is configured such that the sharp edge 1925 slides under the tissue to be cut. FIG. 20 shows a further embodiment of a cutting device 2060 having arms 2062 and a triangular cutting element 2021 coupled to each arm 2062. Each cutting element 2021 can include sharp edge 2025. A point of the triangular cutting element 2021 is configured to pierce tissue, then cut the tissue as it slides along the tissue.

Figure 21A:
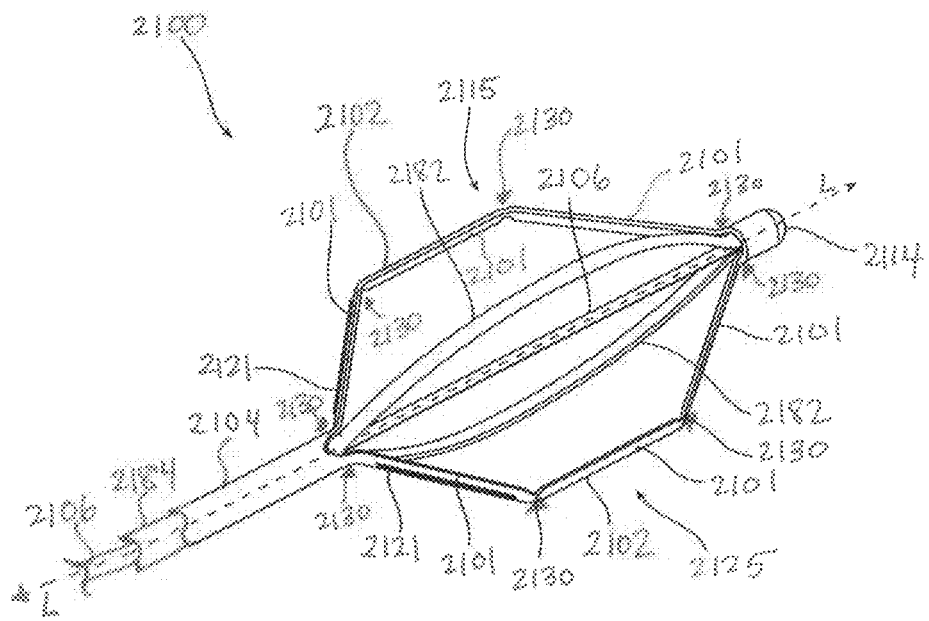
FIG. 21A is a perspective, partially cross-sectional side view of a dissection device configured in accordance with another embodiment of the present technology, shown in a deployed state.
Figure 21B:
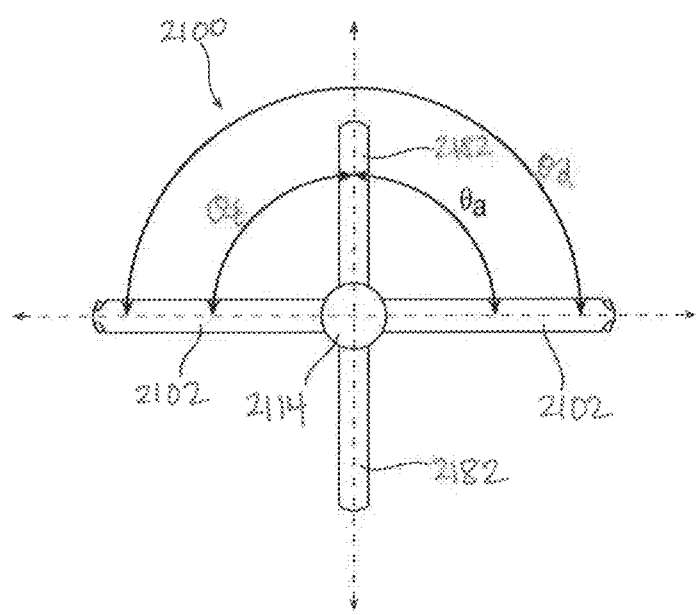
FIG. 21B is an end view of the dissection device of FIG. 21A.

FIG. 21A is a perspective, partial cross-sectional side view of a dissection device 2100 in a deployed state having tensioning members 2182 configured in accordance with the present technology. FIG. 21B is an end view of the dissection device 2100 shown in FIG. 21A. Referring to FIGS. 21A-21B together, the dissection device 2100 can include an outer shaft 2104 (e.g., a hypotube), an inner shaft 2184 (e.g., a hypotube) slidably disposed within at least a portion of the outer shaft 2104, and a pull member 2106 slidably disposed within at least a portion of the inner shaft 2184. The outer shaft 2104 has a proximal portion (not shown) and a distal portion 2115, and the inner shaft 2184 has a proximal portion (not shown) and a distal portion 2125. The outer shaft 2104, the inner shaft 2184, and the pull member 2106 can be coaxially aligned and coupled at an atraumatic distal tip 2106 (e.g., via an adhesive, solder, a weld, or other suitable mechanical fixation devices).

The dissection device 2100 can further include one or more dissection arms 2102 extending distally from the outer shaft 2104 and one or more tensioning arms 2182 extending distally from the inner shaft 2184. In one embodiment, the dissection arms 2102 are formed from portions of the outer shaft 2104, and the tensioning arms 2182 are formed from portions of the inner shaft 2184. The dissection arms 2102 can alternatively be separate components attached to the outer shaft 2104, and/or the tensioning arms 2182 can be separate components attached to the inner shaft 2184. Additionally, in some embodiments (not shown), the dissection arms 2102 can be coupled to the inner shaft 2184 while the tensioning arms 2182 can be coupled to the outer shaft 2104. Upon axial movement of the outer shaft 2104, the inner shaft 2184, and/or the pull member 2106 relative to one another, one or more of the dissection arms 2102 and/or tensioning arms 2182 can extend radially outwardly from a longitudinal axis L of the dissection device 2100 to create a dissection pocket within a vessel wall, as described in greater detail below.

The outer shaft 2104 and the dissection arms 2102 together can define a dissection unit, and they can be made from stainless steel, Nitinol, PEEK and other generally suitable materials with sufficient stiffness and bending characteristics (e.g., elastic or super elastic) that can impart the desired forces. The dissection arms 2102 can be spaced apart about the circumference of the outer shaft 2104 such that, in a low-profile state (see FIG. 22A), the distal portion 2115 of the outer shaft 2104 includes a plurality of openings between the dissection arms 2102 that extend along a length of the outer shaft 2104. Although in FIGS. 21A-21B the dissection device 2100 includes two dissection arms 2102, in other embodiments the dissection device 2100 can have more or fewer than two dissection arms 2102 (e.g., one dissection arm, three dissection arms, four dissection arms, etc.).

As best shown in FIG. 21B, the dissection arms 2102 can be positioned at circumferentially opposite portions of the outer shaft 2104 such that an angle $\theta_d$ between the dissection arms 2102 is about 180 degrees. In other embodiments, the dissection arms 2102 can be positioned at an angle $\theta_d$ that is between about 10 degrees and about 180 degrees, or between about 50 degrees and about 130 degrees (e.g., 60 degrees, 120 degrees, etc.). In some embodiments, it can be advantageous to increase the angle $\theta_d$ between the dissection arms 2102 to more closely mirror the curvature of the vessel wall (and thus reduce stress on the vessel wall), as discussed in greater detail below with reference to FIGS. 22A-22B.

Referring still to FIGS. 21A-21B, each of the dissection arms 2102 can include one or more segments 2101 and one or more joints 2130 between successive segments 2101. The joints 2130 can be portions of the dissection arms 2102 configured to preferentially flex compared to the segments 2101, such as by forming small opposing recesses at locations along the dissection arms 2102 shown in FIG. 21A (e.g., a living hinge), or the flexible joints 2130 can be small pins, elastic polymeric elements, or other devices that enable one segment 2101 to pivot or bend relative to another. In FIGS. 21A-21B, the first and second dissection arms 2102 include three generally linear segments 2101 of substantially equal lengths. In other embodiments, the number of segments 2101, the length of each segment 2101, the angle between segments 2101, and/or the shape of each segment 2101 (e.g., linear, curved, etc.) can be varied amongst a single dissection arm 2102 and/or a plurality of dissection arms 2102 to achieve a desired shape or geometry of the dissection pocket.

The dissection arms 2102 can be configured for blunt and/or sharp dissection of the vessel wall. For example, in the illustrated embodiment, the dissection arms 2102 individually include a blunt or atraumatic dissection surface along their lengths and a cutting element 2121 projecting from the blunt dissection surface of the proximal-most segment 2101. In some embodiments, the cutting elements 2121 can project from the respective dissection arm 2102 perpendicular to the blunt dissection surface on which they are affixed. In some embodiments, one or more of the cutting elements 2121 can project from the surface of the respective dissection arm 2102 a distance of between about 0.2 mm and 2.0 mm. Additionally, the cutting elements 2121 can project a distance of between about 0.5 mm and about 1.5 mm. In a particular embodiment, one or more of the cutting elements 2121 can project a distance of about 1 mm, or 1 mm. Selection of an appropriate cutting element projection distance can be advantageous, as the projection distance can affect the amount of cutting force that the cutting element can apply to the wall tissue before "bottoming out" (e.g., when the wall tissue contacts the surface of the respective dissection arm surrounding the cutting element). For example, the greater the projection distance, the greater the cutting force that can be applied. The cutting elements 2121 can be soldered, welded, glued, or otherwise mechanically fixed to the dissection arms 2102. In some embodiments (not shown), the proximal-most section of the dissection arms 2102 can be exclusively comprised of a cutting element. In other embodiments, the first and/or second dissection arms 2102 can be configured for sharp dissection along their entire lengths and/or configured for blunt dissection along their entire lengths.

Referring still to FIG. 21A, the inner shaft 2184 and the tensioning arms 2182 can define a tensioning unit, and they can be made from stainless steel, Nitinol, PEEK and other generally suitable materials with sufficient stiffness and bending characteristics (e.g., elastic or super elastic) that can impart the desired forces). The tensioning arms 2182 can be spaced apart about the circumference of the inner shaft 2184 such that, in a low-profile state (FIG. 22A), the distal portion 2125 of the inner shaft 2184 includes openings between the tensioning arms 2182 that extend along a length of the inner shaft 2184. Although in FIGS. 21A-21B the dissection device 2100 includes two tensioning arms 2182, in other embodiments, the dissection device 2100 can have more or fewer tensioning arms 2182 (e.g., one tensioning arm, three tensioning arms, four tensioning arms, etc.).

As best shown in FIG. 21B, the tensioning arms 2182 can be positioned at circumferentially opposite portions of the inner shaft 2184 such that an angle $\theta_t$ between the tensioning arms 2182 is about 180 degrees. In other embodiments, the tensioning arms 2182 can be positioned at an angle $\theta_t$ that is between about 10 degrees and about 180 degrees, or between about 50 degrees and about 130 degrees (e.g., 60 degrees, 120 degrees, etc.). Additionally, the inner shaft 2184 and the outer shaft 2104 can be positioned relative to one another such that the tensioning arms 2182 and the dissection arms 2102 are positioned at an angle $\theta_a$ that is generally uniform about the circumference of the dissection device 2100. For example, as shown in FIG. 21B, when the dissection device 2100 includes two dissection arms 2102 and two tensioning arms 2182, the arms 2102, 2182 can deploy at an angle $\theta_a$ of about 90 degrees. In other embodiments, the dissection device 2100 can have other configurations.

Figure 22A:
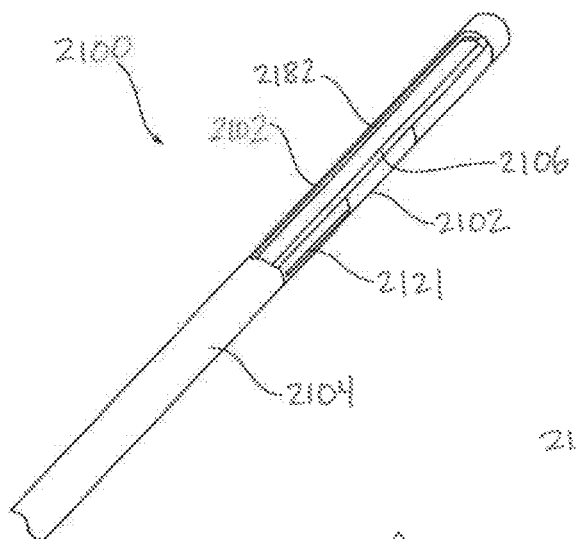
FIG. 22A is a top perspective view of the dissection device of FIGS. 21A and 21B in a low-profile state configured in accordance with an embodiment of the present technology. The delivery catheter constraining the device has been removed for ease of illustration.
Figure 22B:
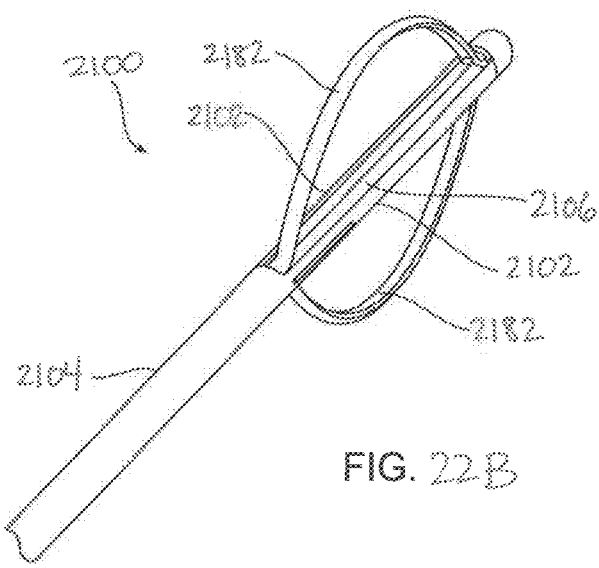
FIG. 22B is a top perspective view of the dissection of FIGS. 21A and 21B in a first deployed state configured in accordance with an embodiment of the present technology.
Figure 22C:
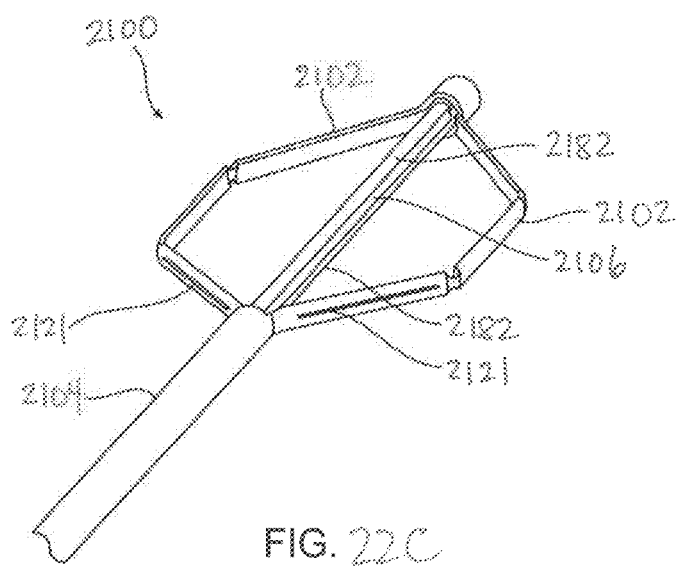
FIG. 22C is a top perspective view of the dissection of FIGS. 21A and 21B in a second deployed state configured in accordance with an embodiment of the present technology.

FIG. 22A shows the dissection device 2100 in a collapsed or low-profile state, a FIG. 22B shows the dissection device 2100 in a deployed state with only the tensioning arms 2182 deployed, and FIG. 22B shows the dissection device 2100 in a deployed state with only the dissection arms 2102 deployed. To deploy the tensioning arms 2182, the inner shaft 2184 can be pushed distally relative to the pull member 2106 (or the pull member 2106 can be pulled proximally relative to the inner shaft 2184). To deploy the dissection arms 2102, the outer shaft 2104 can be pushed distally relative to the pull member 2106, or the pull member 2106 can be pulled proximally relative to the outer shaft 2104. The tensioning arms 2182 can be deployed independently of the dissection arms 2102 (and vice versa) such that the tensioning arms 2182 can be deployed to a desired extent irrespective of the state of the dissection arms 2102.

A method of using the dissection device 2100 will now be described with reference to FIGS. 2A-2F and FIG. 23. To begin, the dissection device 2100 can be intravascularly positioned in the low-profile state at a treatment site within the lumen of a blood vessel V. Although in some embodiments the dissection device 2100 is intravascularly delivered within a delivery device (e.g., a delivery sheath), such a delivery device is not shown in FIGS. 22A-22C to provide a better view of the dissection and tensioning arms 2102, 2182 in the low-profile state. Once positioned at the treatment site, the dissection device 2100 can then be advanced through an opening O (FIG. 2A) at an interior surface of the vessel wall W at the treatment site and positioned in a space S within the vessel wall W (FIG. 2A). Before and/or during deployment of the dissection arms 2102, the tensioning arms 2182 can be deployed (FIG. 22B) to create a tension T (FIG. 23) in the dissection pocket DP that is generally transverse to the plane of dissection (e.g., aligned with dissection force D in FIG. 23).

Before, during, and/or after deployment of the tensioning arms 2182, the outer shaft 2104 can be pushed distally relative to the pull member 2106 to deploy the dissection arms 2102. As the dissection arms 2102 flex outwardly away from a longitudinal axis of the outer shaft 2104, a surface of the leading segment (e.g., radially furthest from the longitudinal axis of the device 2100) of the respective dissection arm 2102 pushes outwardly against the vessel wall at the periphery of the space in which the dissection device 2100 is positioned, thereby forcing the tissue to separate (e.g., via blunt or sharp dissection). For example, the dissection arms 2102 can apply a dissection force D (FIG. 23) that separates the vessel wall W into an outer layer OL and an inner layer IL (depicted schematically in FIG. 23). The outer layer OL can include intimal, medial, and/or adventitial tissue, and the inner layer IL can include intimal, medial, and/or adventitial tissue. For example, expansion of the dissection arms 2102 can separate an intimal layer from a medial layer, a medial layer from an adventitial layer, a sub-medial layer from a sub-medial layer, an intimal and sub-medial layer from a sub-medial layer, etc.

Figure 23:
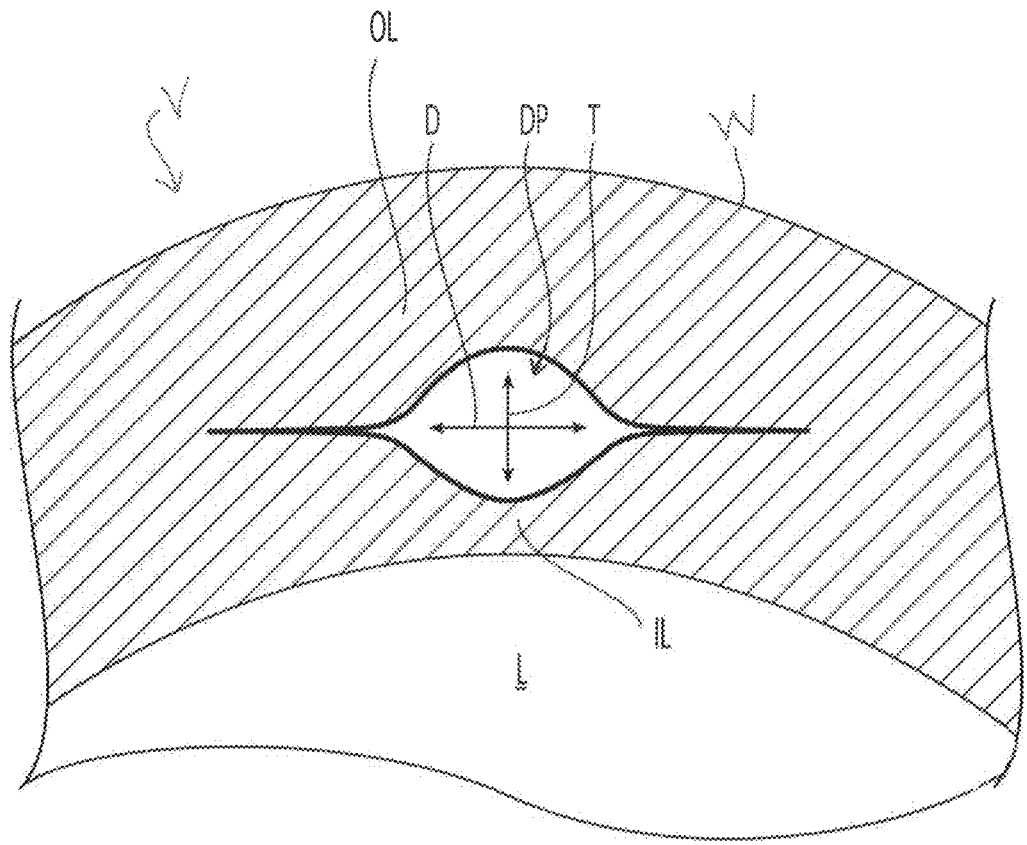
FIG. 23 is a schematic end view of a portion of a vessel wall, showing a dissection pocket during formation using the dissection devices configured in accordance with the present technology.

In some procedures, it may be beneficial to deploy the dissection arms 2102 and the tensioning arms 2182 simultaneously. In such a scenario, the dissection arms 2102 can widen the dissection pocket DP in a direction D (FIG. 23) while the tensioning arms 2182 can widen the dissection pocket DP in a direction T (FIG. 23). This widening in a secondary direction can provide additional dissection force and further enlarge the space S and/or dissection pocket DP.

To widen the opening O to form a mouth M (FIG. 2C) (and thus a leaflet L), the dissection device 2100 can be pulled proximally, thereby forcing the cutting elements 2121 into contact with the vessel wall tissue adjacent the opening (e.g., extending laterally away from the opening O). Depending on the size of the mouth M desired, before retraction of the device 2100, the pull member 2106 can be pulled proximally to move the dissection arms 2102 inwardly towards the longitudinal axis L of the device 2100, thereby decreasing the reach of the cutting elements 2121 (and thus the size of the mouth M). In some embodiments, the device 2100 can widen the opening O while being retracted in the low-profile state, as the proximal portion of the cutting elements 2121 create the mouth M. This widening may also facilitate the ability of the cutting elements 2121 to create mouth M by putting the opening in tension as the cutting elements 2121 engage the tissue.

Because the inner shaft 2184 and the outer shaft 2104 can move axially independently of one another, the dissection arms 2102 and the tensioning arms 2182 can be controlled independently of one another such that they can be deployed or expanded at different times and at different rates. Such independent control of the dissection and tensioning arms 2102, 2182 ensures that a desired tensioning force (e.g., a constant force) is applied as the dissection propagates laterally within the vessel wall W and frees up additional slack tissue that requires additional tensioning. For this reason, fine control of the expansion rate of the tensioning arms 2182 can be advantageous for creation of a dissection pocket DP within a vessel wall W. It is believed that because the vessel wall is generally circular, tension does not increase linearly as the width of the dissection pocket and/or space within the vessel wall increases. For example, as the dissection arms 2102 begin to expand, it may be advantageous to increase the amount of perpendicular tension applied to the vessel wall (from within the dissection pocket DP and/or space S) at a relatively high rate, as even small increases in the width of the dissection pocket DP and/or space S can create relatively large lengths of slack tissue between the tensioning arm 2182 and the nearest edge of the growing dissection pocket DP and/or space S. As the dissection makes its way around the curvature of the dissection pocket DP and/or space S, small increases in the width of the dissection pocket DP and/or space S may require less tension than would the same increase in width earlier in the dissection process. For this reason, it may be advantageous for the tensioning arms 2182 to expand to a greater extent and/or rate in the early stages of expansion of the dissection arms 2102, and then to a relatively lesser extent and/or rate near the end of the dissection arm expansion.

Figure 24A:
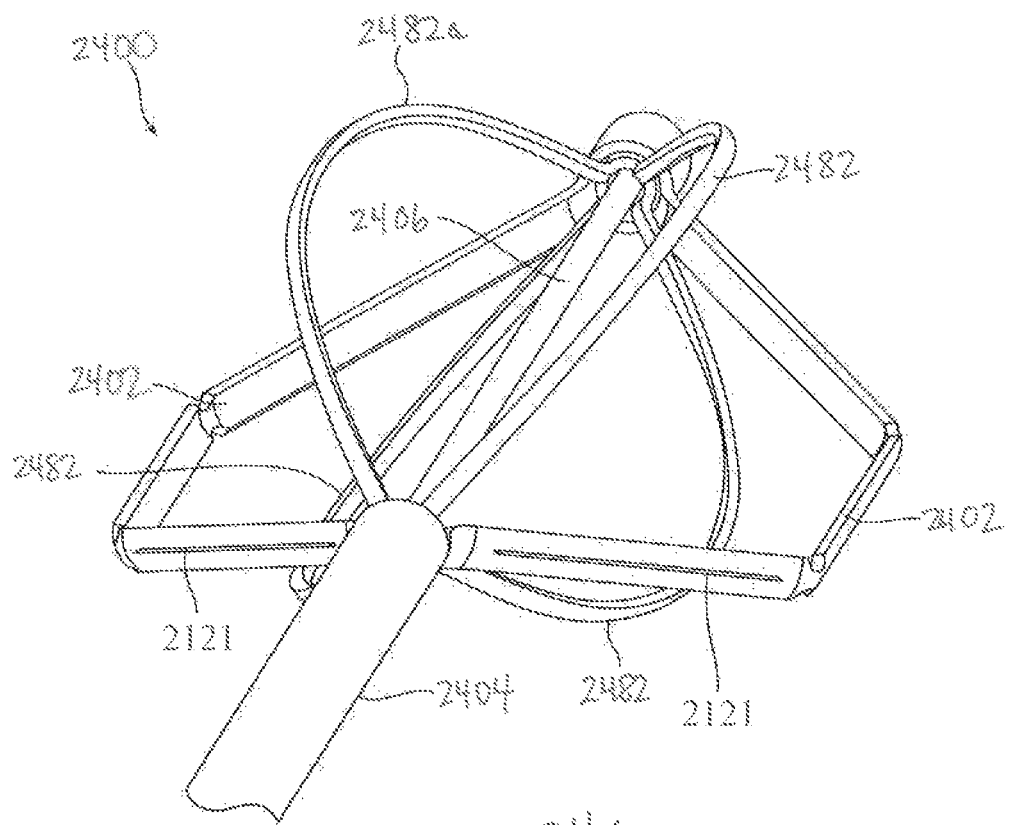
FIG. 24A is an axial perspective view of another embodiment of a dissection device configured in accordance with the present technology.
Figure 24B:
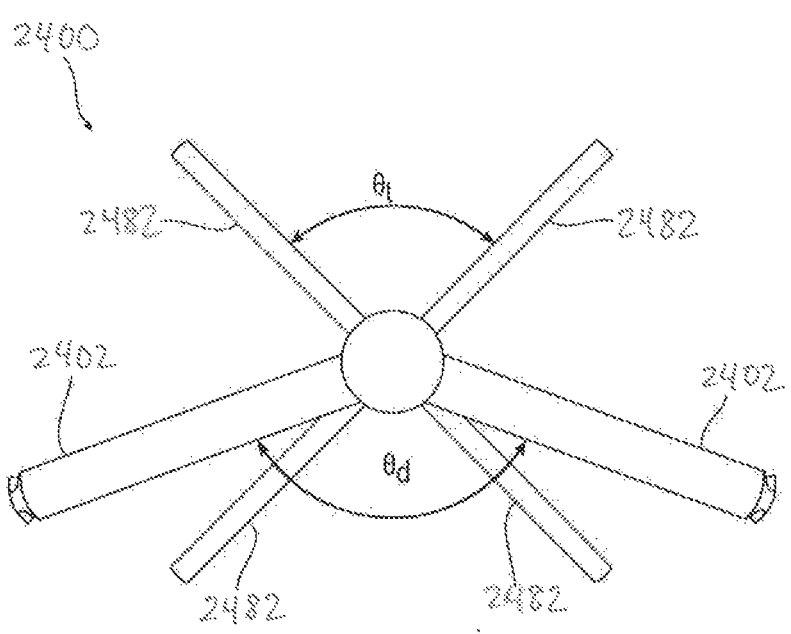
FIG. 24B is an end view of the dissection device shown in FIG. 24A.

FIG. 24A is an axial perspective view of another dissection device 2400 shown in a deployed state in accordance with the present technology, and FIG. 24B is an end view of the dissection device 2400 shown in FIG. 24A. The dissection device 2400 can be generally similar to the dissection device 2100 shown in FIGS. 21A-22C, except the dissection device 2400 includes four tensioning arms 2482 and two angled dissection arms 2402. Referring to FIGS. 24A and 24B together, the centerline of the dissection arms 2402 are less than 180 degrees from each other (see, $\theta_d$ in FIG. 24B), such that the dissection arms 2402 do not expand outward along the same plane. In one such embodiment, the angle $\theta_d$ between the dissection arms 2402 is about 140 degrees. In other embodiments, the angle $\theta_d$ between the dissection arms 2402 is between about 100 and about 180 degrees. This angled dissection may be advantageous to accommodate the curvature of the vessel wall.

Additionally, in the embodiment shown in FIGS. 24A and 24B, the dissection device 2400 does not include any tensioning arms at 0 and 180 degrees. In the illustrated embodiment, each tensioning arm 2482 expands outward at an angle of approximately 25 degrees from the central vertical axis (or between 0 and 50 degrees). This configuration may enhance the stability of the device relative to the vessel wall to inhibit or prevent unintended rotation of the entire device upon deployment of the tensioning arms 2482. Furthermore, this configuration provides tension to the tissue in close proximity to the plane of dissection.

Figure 25:
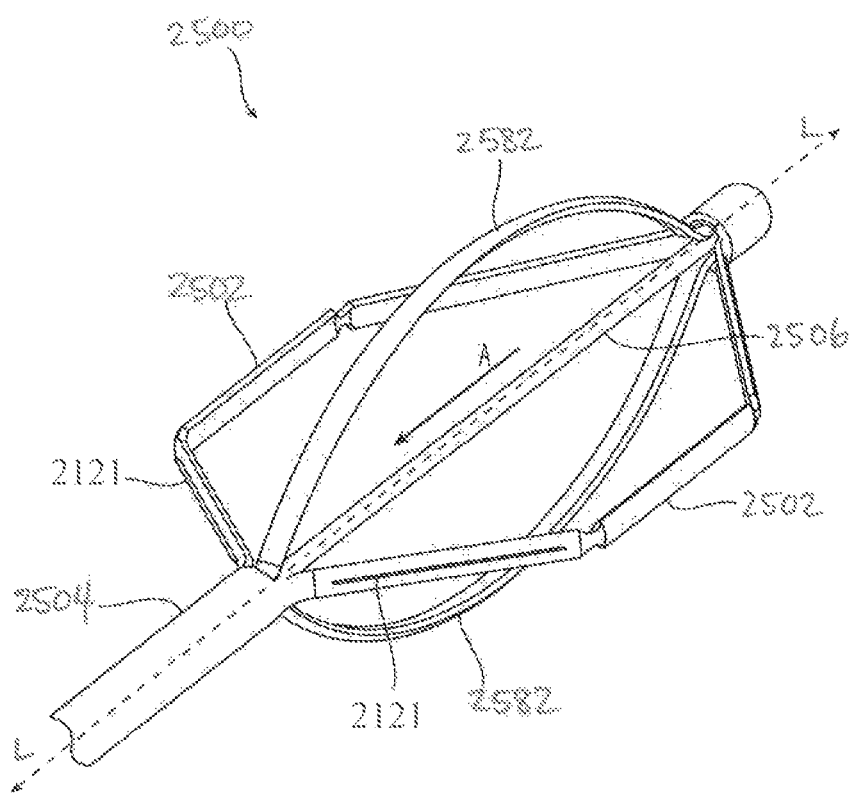
FIG. 25 is a side perspective view of another embodiment of a dissection device configured in accordance with the present technology.

FIG. 25 is an axial perspective view of another dissection device 2500 shown in a deployed state in accordance with the present technology. The dissection device 2500 can be generally similar to the dissection device 2100 shown in FIGS. 21A-21C, except the dissection device 2500 does not include an inner shaft, and the dissection arms 2502 and the tensioning arms 2582 are both coupled to the outer shaft 2504. As such, the dissection arms 2502 and the tensioning arms 2582 are not controlled independently. Actuation can be accomplished by retracting the pull member 2506 relative to the outer shaft 2506, or by advancing the outer shaft 2506 distally relative to the pull member 2506.

Figure 26:
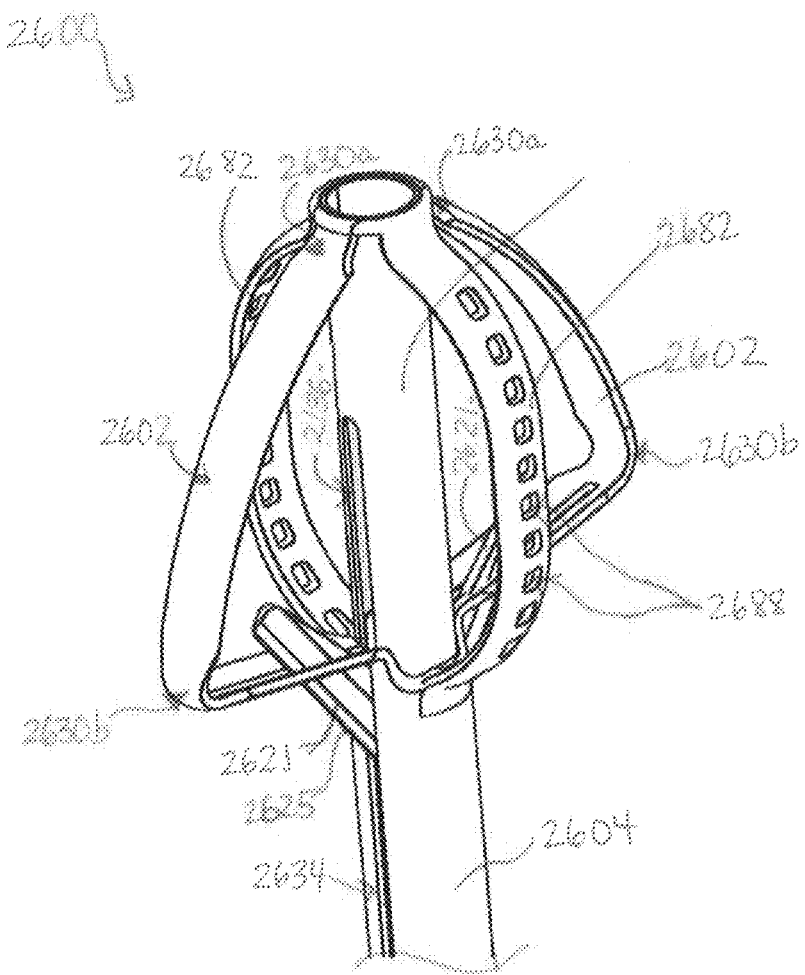
FIG. 26 is an isometric view of another embodiment of a dissection device configured in accordance with the present technology.

FIG. 26 shows another embodiment of a dissection device configured in accordance with the present technology. The dissection device 2600 includes tensioning arms 2682. Each of the tensioning arms 2682 can include a plurality of openings along its length. Such a configuration can provide improved flexibility to the tensioning arms 2682.

3.0 ADDITIONAL EMBODIMENTS OF DISSECTION DEVICES

Figure 27A:
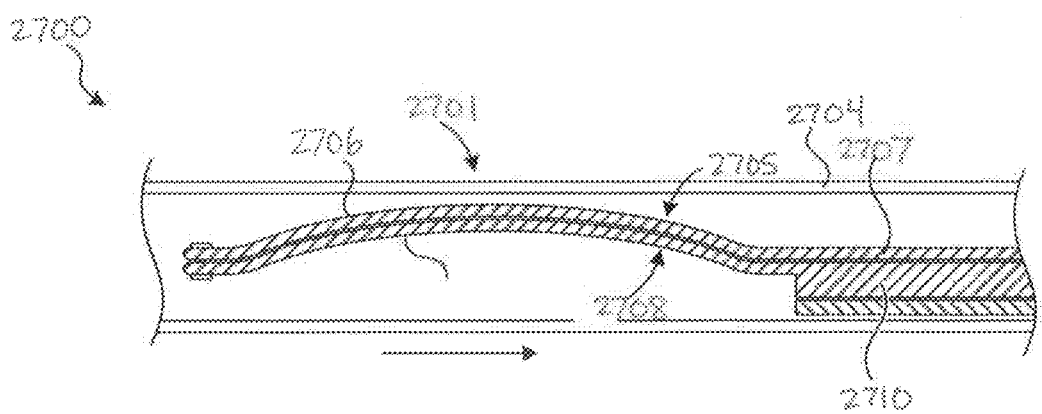
FIG. 27A is a side view of a dissection device in a low-profile state configured in accordance with an embodiment of the present technology.

FIG. 27A is a cross-sectional side view of a dissection device 2700 in a low-profile state configured in accordance with another embodiment of the present technology. As shown in FIG. 27A, the dissection device 2700 can include a retractable sheath 2704 and a dissection device 2701 slidably positioned within the retractable sheath 2704. The dissection device 2701 can include an outer member 2705 and an inner member 2709. The inner member 2709 can include a proximal portion 2710 positioned within the outer member 2705 and an arm 2709 that extends distally from a distal portion of the proximal portion 2710. The outer member 2705 can include a proximal portion 2707 which surrounds at least a portion of the proximal inner member 2710. The outer member 2705 can also include a distal portion 2706 that extends distally from a distal portion of the proximal outer member 2707. A distal region of the distal outer member 2706 can be coupled to a distal region of the distal inner member 2709. As shown in FIG. 27A, in the low-profile state, the dissection device 2701 can have a generally linear shape with a slight bend. For example, the distal inner member 2709 can have a radius of curvature that is slightly less than that of the distal outer member 2706, such that the distal inner member 2709 sits within or "spoons" with the distal outer member 2706. At least the distal inner member 2709 and the distal outer member 2706 can be made of a shape memory material such that, once the sheath 2704 is withdrawn, the distal inner and outer members 2709, 2706 can assume their natural, curved shapes, as shown in FIG. 27B.

Figure 27B:
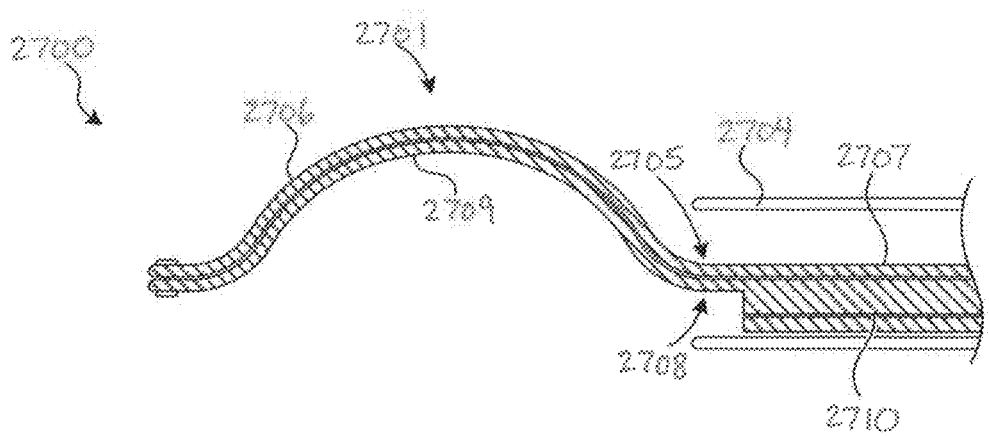
FIG. 27B is a side view of the dissection device shown in FIG. 27A in a first deployed state configured in accordance with an embodiment of the present technology.
Figure 27C:
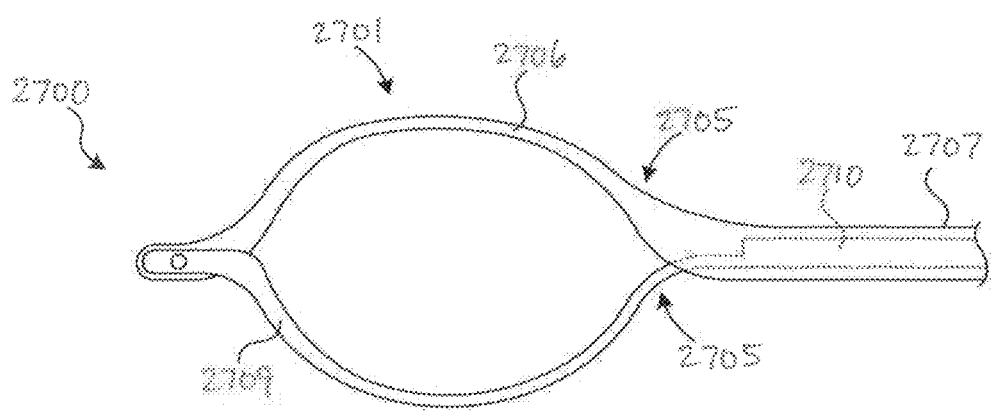
FIG. 27C is a top view of the dissection device shown in FIGS. 27A and 27B in a second deployed state configured in accordance with an embodiment of the present technology.

FIG. 27C is a top view of the dissection device 2700 shown in FIGS. 27A and 27B in a second deployed state configured in accordance with an embodiment of the present technology. As shown in FIG. 27C, the proximal portions (not shown) of the outer and inner members 2705, 2709 can be rotated in opposite directions to force the distal members 2706, 2709 to flex and fan out, together sweeping out at least a portion of the dissection pocket.

FIGS. 28A-28D are top views of a dissection device 2800 showing various states configured in accordance with an embodiment of the present technology. As shown in FIG. 28A, the dissection device 2800 can include a first elongated member 2802, a second elongated member 2806 positioned generally parallel to the first elongated member 2802, and a connecting member 2804 coupled to the distal regions of the first and second members 2802, 2806. The first member 2802 can be coupled to a first side of the connecting member 2804, and the second member 2806 can be coupled to a second side of the connecting member 2804 that is opposite the first side. As such, proximal and distal movement of the first and second members 2802, 2804 (similar to a train drive) can cause the connecting member 2804 to rotate about the distal regions, thereby sweeping out at least a portion of the periphery of a dissection pocket along its outermost edge.

Figure 29A:
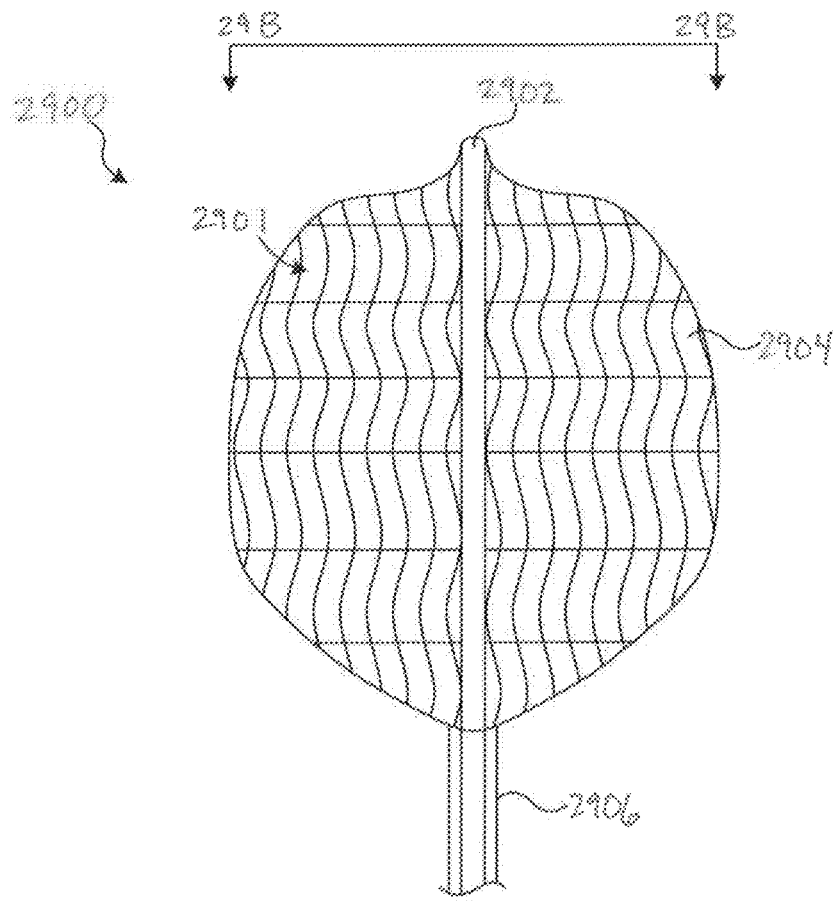
FIG. 29A is a top view of a dissection device configured in accordance with an embodiment of the present technology.
Figure 29B:
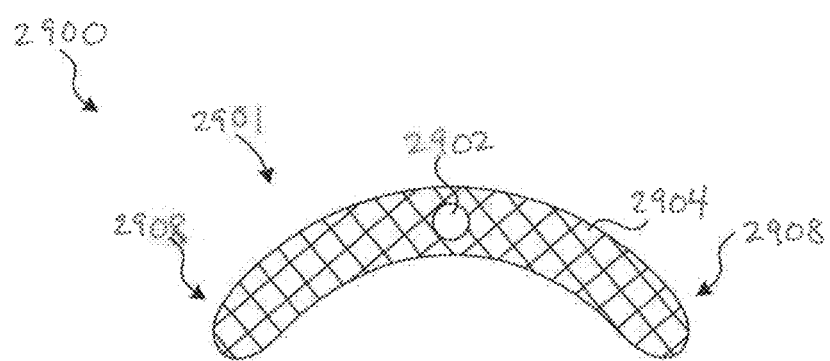
FIG. 29B is an end view of the dissection device shown in FIG. 29A.

FIG. 29A is a top view of a dissection device 2900 in a deployed state configured in accordance with an embodiment of the present technology, and FIG. 29B is an end view of the dissection device 2900 shown in FIG. 29A. As shown in FIGS. 29A and 29B, the dissection device 2900 can include a dissection device 2901 and a retractable sheath 2906. The dissection device 2901 can include a braided wire cage 2904 made of a spring material or shape memory material coupled to a support member 2902. The cage 2904 can be configured to collapse into a low-profile state during delivery (within the sheath 2906). During deployment, the dissection device 2901 can be advanced distally from the sheath 2906 (or the sheath 2906 can be withdrawn), thereby allowing the cage 2904 to assume an expanded, deployed configuration. For example, the cage 2901 can have a rounded shape, or any shape desired for the dissection pocket. As best shown in FIG. 29B, in one embodiment the cage 2901 can curve inwardly such that the lateral portions 2909 of the cage bend back towards the longitudinal axis of the support member 2902. As such, the curved cage 2904 can better align the with curvature of the lumen at the treatment site.

Figure 30C:
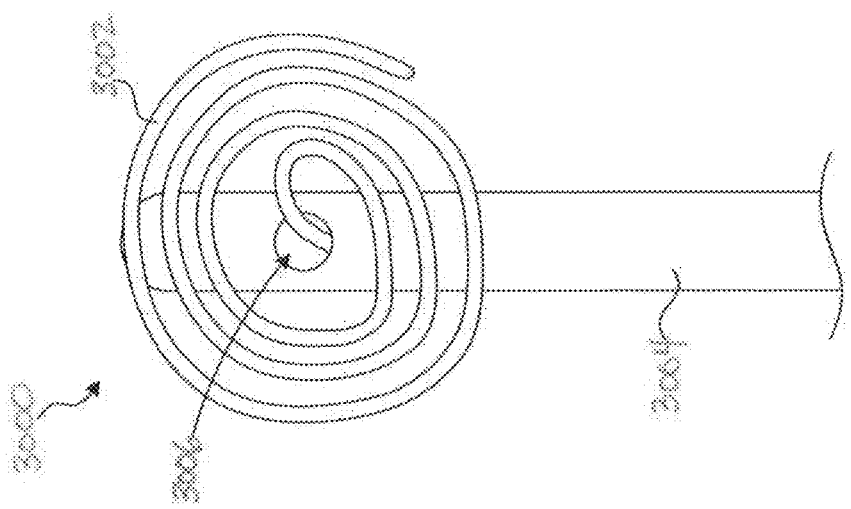
FIGS. 30A-30C are top views of a dissection device during various stages of deployment configured in accordance with an embodiment of the present technology.
Figure 30B:
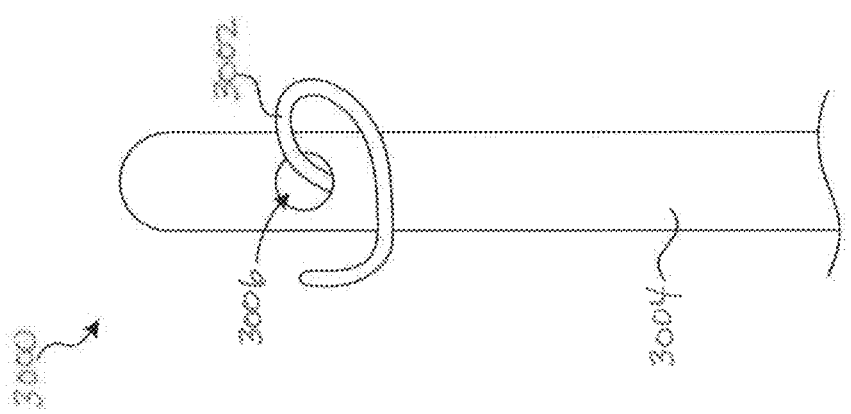
Figure 30A:
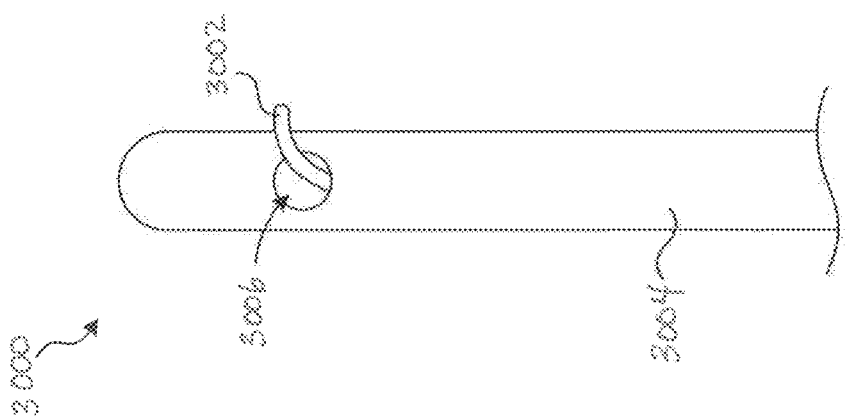

FIGS. 30A-30C are top views of a dissection device 3000 during various stages of deployment configured in accordance with an embodiment of the present technology. As shown in FIGS. 30A-30C, the dissection device 3000 can include a shaft 3004 having an opening 3006 at a distal region and an expandable member 3002 positioned at least partially within a lumen of the shaft 3004. The expandable member 3002 can have a proximal portion (not shown) and a distal portion configured to be advanced through the opening 3006 in the shaft 3004 during deployment. As the expandable member 3002 is advanced through the opening 3006, the expandable member 3002 coils about itself, thereby amassing a larger surface area as more of the expandable member 3002 is fed through the opening 3006. As such, the periphery of the expandable member 3002 can form at least a portion of the periphery of the dissection pocket.

Figure 31:
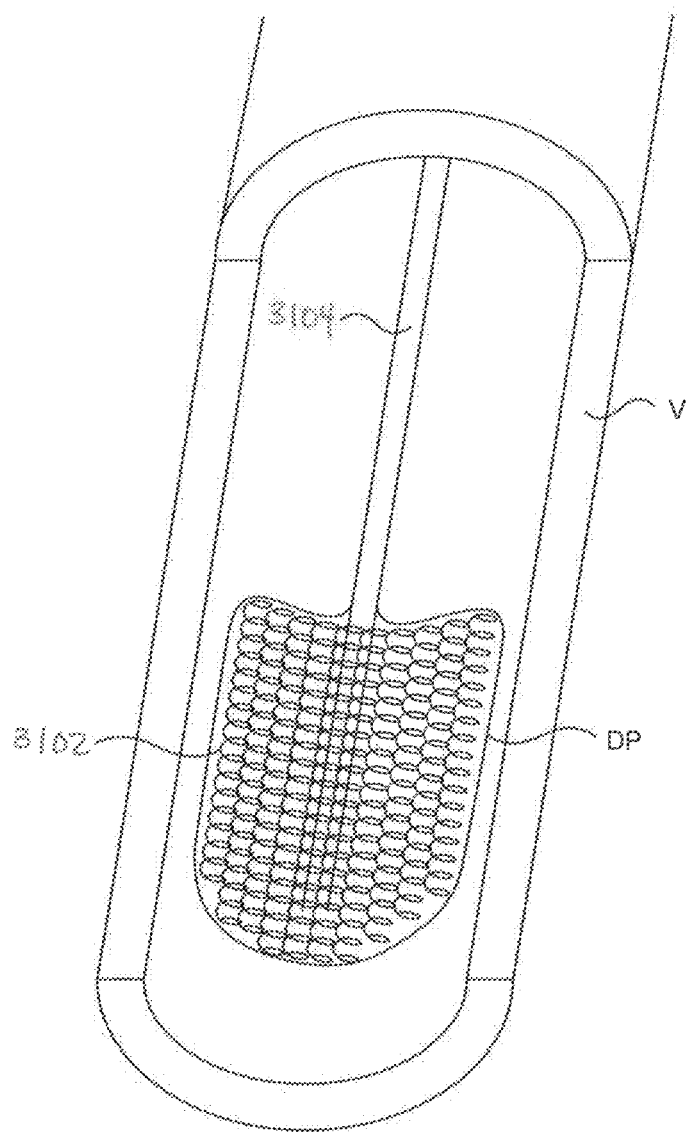
FIG. 31 is a top perspective view of a dissection device shown within a blood vessel and configured in accordance with an embodiment of the present technology. The blood vessel is shown in partial cross-section for ease of illustration.

FIG. 31 is a top perspective view of a dissection device 3100 shown within a blood vessel V and configured in accordance with an embodiment of the present technology. The blood vessel V is shown in partial cross-section for ease of illustration. As shown in FIG. 31, the dissection device 3100 can include an elongated tubular shaft 3104 and a coiled wire 3102 configured to be advanced through the shaft 3104 and deployed within the vessel wall to form or enlarge a dissection pocket DP. The wire 3102 can be made of a shape memory material. As such, when the wire 3102 is advanced past the shaft 3104, it assumes a densely packed, coiled shape.

Figure 32A:
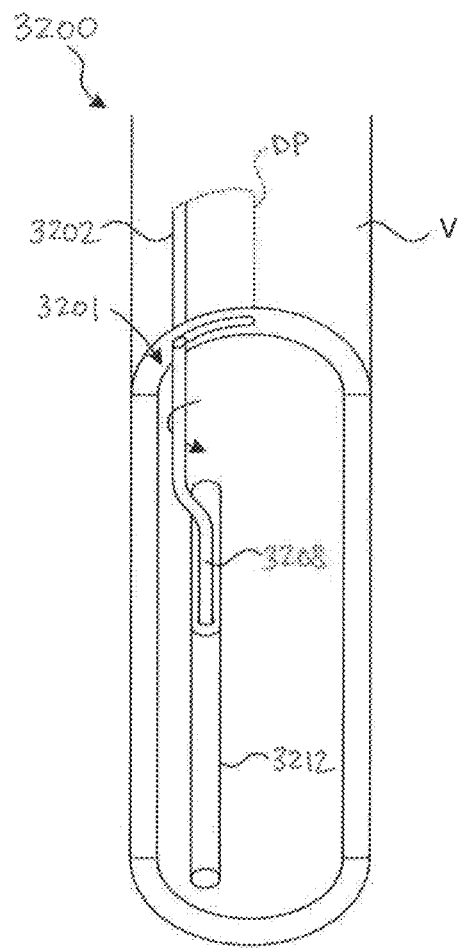
FIG. 32A is a top perspective view of a dissection device shown within a blood vessel and configured in accordance with an embodiment of the present technology. The blood vessel is shown in partial cross-section for ease of illustration.
Figure 32B:
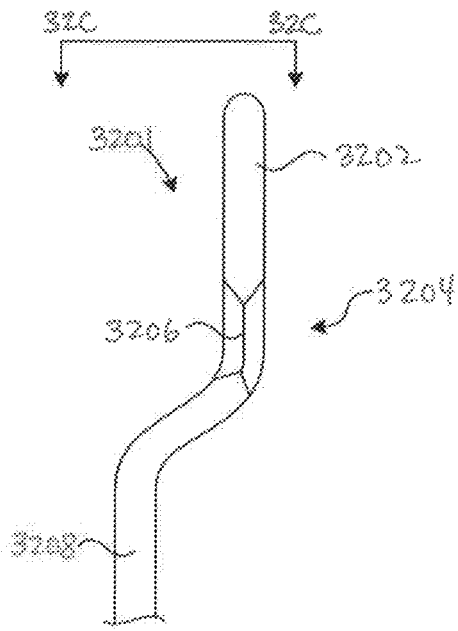
FIG. 32B is a top, isolated view of the dissection device shown in FIG. 32A configured in accordance with an embodiment of the present technology.
Figure 32C:
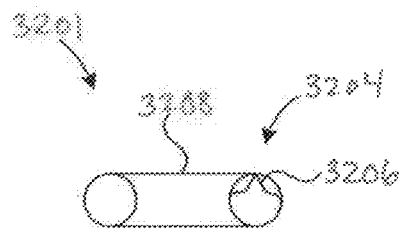
FIG. 32C is an end view of the dissection device shown in FIG. 32B configured in accordance with an embodiment of the present technology.

FIG. 32A is a top perspective view of a dissection device 3200 shown within a blood vessel V and configured in accordance with an embodiment of the present technology. The blood vessel is shown in partial cross-section for ease of illustration. FIG. 32B is an isolated top view of the dissection component 3201 shown in FIG. 32A, and FIG. 32C is an end view of FIG. 32B. Referring to FIGS. 32A-32C together, the dissection device 3200 can include a delivery shaft 3212 and a dissection component 3210 which is curved for example in a bayonet shape and slidably positioned within the shaft 3212. As shown in FIGS. 32B and 32C, the dissection device 3201 can include a proximal portion 3209 (only a portion of which is shown in FIG. 32B), a cutting portion 3204 having a cutting edge 3206, and a distal portion 3202. The cutting portion 3204 can be positioned distal to a bend in the device 3201, and proximal of the distal portion 3202. The distal portion 3202 can be generally atraumatic. As shown in FIG. 32A, the dissection device 3201 can be advanced distally from the delivery device shaft 3212 (positioned with the lumen of the vessel V), inserted into the vessel wall, and rotated to sweep out a dissection pocket DP in the vessel wall.

Figure 33A:
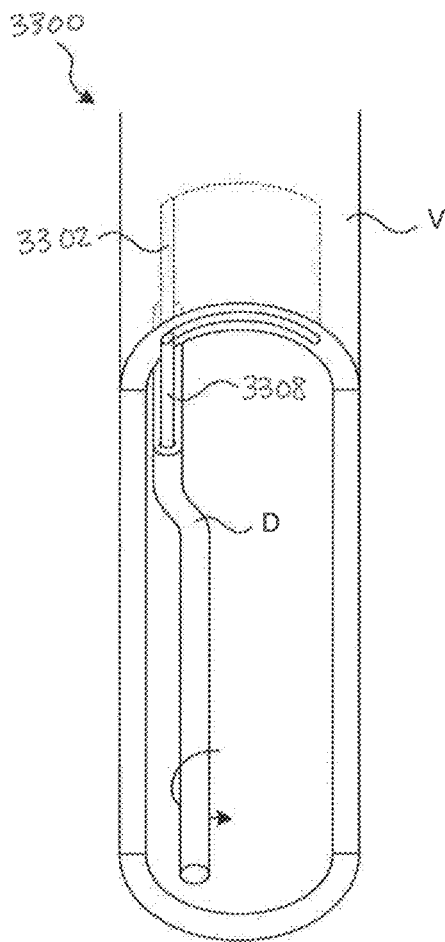
FIG. 33A is a top perspective view of a dissection device shown within a blood vessel and configured in accordance with an embodiment of the present technology. The blood vessel is shown in partial cross-section for ease of illustration.
Figure 33B:
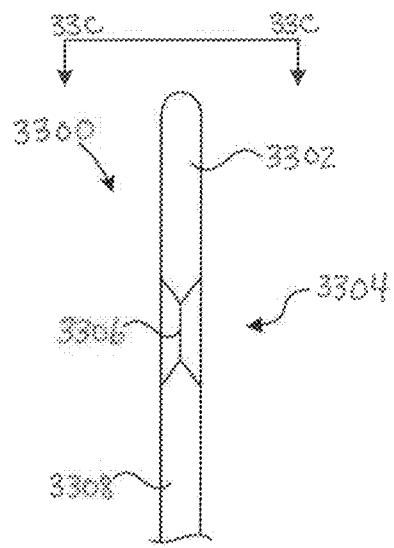
FIG. 33B is a top, isolated view of the dissection device shown in FIG. 33A configured in accordance with an embodiment of the present technology.
Figure 33C:
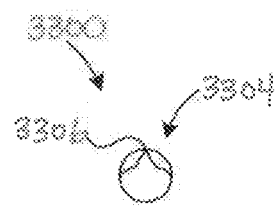
FIG. 33C is an end view of the dissection device shown in FIG. 33B configured in accordance with an embodiment of the present technology.

FIG. 33A is a top perspective view of a dissection device 3300 shown within a blood vessel V and configured in accordance with an embodiment of the present technology. The blood vessel is shown in partial cross-section for ease of illustration. FIG. 33B is an isolated top view of the dissection device 3301 shown in FIG. 33A, and FIG. 33C is an end view of FIG. 33B. Referring to FIGS. 33A-33C together, the dissection device 3300 of FIGS. 33A-33C can be generally similar to the dissection device 3200 of FIGS. 32A-32C, except the dissection device 3300 of FIGS. 33A-33C is generally linear and the delivery shaft 3312 is curved in a bayonet shape.

FIG. 34A is a top perspective view of another embodiment of a dissection device 3400 shown within a blood vessel V and configured in accordance with an embodiment of the present technology. The blood vessel V is shown in partial cross-section for ease of illustration. As shown in FIG. 34A, the dissection device 3400 can include an elongated hollow shaft 3402 and a gel 3404 configured to be delivered through the shaft 3402 and into the vessel wall at a specific pressure and flow rate configured to form or enlarge a dissection pocket DP. FIG. 34B is a cross-sectional end view of the gel 3404 shown positioned within the vessel wall. The gel 3404 may optionally be removed via aspiration via hollow shaft 3402 after the pocket is created. Alternately, the gel may be disbursed or reabsorbed.

4.0 EXAMPLES

The following examples are illustrative of several embodiments of the present technology:

1. A device for separating tissue within a wall of a blood vessel, the device comprising:
   an elongated shaft having a longitudinal axis, a proximal portion, and a distal portion configured to be (1) intravascularly delivered to a treatment site within the blood vessel, (2) advanced through an opening at an interior surface of the blood vessel wall to a space within the wall, and (3) positioned within the space within the wall of the blood vessel at the treatment site;
an elongated member slidably positioned within the elongated shaft;
a dissection arm at the distal portion of the shaft, the arm having a longitudinal axis and moveable between a low-profile state and a deployed state via axial movement of the elongated member relative to the shaft, and wherein—
  in the low-profile state, the longitudinal axis of the arm is parallel to the longitudinal axis of the elongated shaft,
  in the deployed state, a portion of the arm flexes outwardly away from the longitudinal axis of the shaft, and
  the arm is configured to be deployed within the space such that, as the arm moves from the low-profile state to the deployed state, the arm pushes against vessel wall tissue at a periphery of the space, thereby separating tissue at the periphery to form a dissection pocket having a predetermined shape.

2. The device of example 1 wherein the device further comprises a tensioning arm at the distal portion, the tensioning arm having a low-profile state and a deployed state, and wherein, in the deployed state, the tensioning arm flexes outwardly away from the longitudinal axis of the shaft.

3. The device of example 1 or example 2 wherein the dissection arm is configured to flex outwardly within a first plane, and wherein the device further comprises one or more tensioning arms at the distal portion, the tensioning arm having a low-profile state and a deployed state, and further wherein, in the deployed state, the tensioning arm flexes outwardly away from the longitudinal axis of the shaft within a second plane that is angled relative to the first plane.

4. The device of any of examples 1-3 wherein the arm is a first arm and wherein the device further includes a second arm at the distal portion, wherein an outline of the first and second arms in the deployed state defines the predetermined shape of the dissection pocket.

5. The device of any of examples 1-4 wherein the arm is integral with the shaft.

6. The device of any of examples 1-5 wherein a distal end portion of the elongated member is coupled to a distal end portion of the elongated shaft.

7. The device of any of examples 1-6, further comprising a cutting element positioned along at least a portion of the arm and configured to cut vessel wall tissue adjacent the opening to widen the opening.

8. The device of any of examples 1-7, further comprising:
a tensioning arm at the distal portion, the tensioning arm having a low-profile state and a deployed state, and wherein, in the deployed state, the tensioning arm flexes outwardly away from the longitudinal axis of the shaft.
a cutting element positioned along at least a portion of the arm and configured to cut vessel wall tissue adjacent the opening to widen the opening.

9. A dissection device, comprising:
an elongated shaft having a proximal region and a distal region, wherein the distal region is configured to be positioned within a space within a blood vessel at a treatment site;
a tensioning unit at the distal region of the shaft including a tensioning arm configured to flex outwardly away from the longitudinal axis of the shaft to create tension in the tissue surrounding the space; and
a dissection unit at the distal region of the shaft including a dissection arm configured to flex outwardly away from the longitudinal axis of the shaft to push against vessel wall tissue surrounding the space to separate the vessel wall tissue and enlarge the space.

10. The device of any of examples 1-9 wherein the dissection device does not include a balloon.

11. The device of any of examples 1-10 wherein the tensioning arm is a first tensioning arm, and wherein the tensioning unit includes a seconding tensioning arm positioned opposite the first tensioning arm about the circumference of the shaft.

12. The device of any of examples 1-10 wherein the dissection arm is a first dissection arm, and wherein the dissection unit includes a second dissection arm positioned opposite the first dissection arm about the circumference of the shaft.

13. The device of any of examples 1-12 wherein:
the tensioning arm is a first tensioning arm, and wherein the tensioning unit includes a seconding tensioning arm positioned opposite the first tensioning arm about the circumference of the shaft; and
the dissection arm is a first dissection arm, and wherein the dissection unit includes a second dissection arm positioned opposite the first dissection arm about the circumference of the shaft.

14. The device of any of examples 1-3 wherein the dissection arm includes a cutting element having a sharp edge configured to cut vessel wall tissue.

15. The device of any of examples 1-14, further including an elongated member positioned within the shaft and configured to move axially relative to the shaft.

16. The device of any of examples 1-15 wherein the dissection unit is configured to be deployed independently of the tensioning unit.

17. A method, comprising:
intravascularly positioning a dissection device within a blood vessel, wherein the dissection device includes an elongated shaft having a distal portion and a dissection arm at the distal portion;
advancing the distal portion through an opening in an interior surface of the blood vessel wall, thereby positioning the distal portion in a space within the wall; and
while the distal portion is positioned within the space, separating tissue at a periphery of the space with the dissection arm by flexing a portion of the arm outwardly away from a longitudinal axis of the shaft, thereby creating a dissection pocket within the vessel wall.

18. The method of example 17 wherein the dissection device further comprises an elongated member slidably disposed within the elongated shaft, and wherein the method includes axially moving the elongated member relative to the elongated shaft to flex the arm outwardly away from the longitudinal axis of the shaft.

19. The method of example 17 wherein the dissection device further comprises a tensioning arm at the distal portion, and wherein the method includes creating tension within the tissue surrounding the space with the tensioning arm by flexing the tensioning arm away from the longitudinal axis of the shaft into contact with the tissue.

20. The method of example 17 wherein creating tension within the tissue occurs before, during, and/or after separating vessel wall tissue with the dissection arm.

21. The method of example 17 wherein the dissection device further comprises a cutting element, and wherein the method further includes cutting vessel wall tissue adjacent the opening with the cutting element.

22. The method of example 21 wherein cutting vessel wall tissue occurs before, during, and/or after separating tissue at the periphery of the space.

23. The method of example 21, further including pushing the cutting element distally relative to the arm to cut the vessel wall tissue.

24. The method of example 21, further including pulling the cutting element proximally to cut the vessel wall tissue.

25. The method of example 21, further including pulling the cutting element proximally relative to the arm to cut the vessel wall tissue.

26. The method of example 21, further including advancing the cutting element along an outer surface of the arm to cut the vessel wall tissue.

27. The method of example 21, further including advancing the cutting element along a slot within the arm to cut the vessel wall tissue.

28. The method of example 21 wherein the cutting element is integral with the arm.

29. The method of example 21 wherein the cutting element is a separate component from the shaft, and wherein the method further includes positioning the cutting element at or near the opening by advancing the cutting element through or over the shaft.

30. The method of example 21 wherein the cutting element is a separate component from the shaft, and wherein the method further includes:
   removing the distal portion from the dissection pocket; and
   positioning the cutting element at or near the opening.

31. The method of example 21 wherein cutting vessel wall tissue occurs at a first time, and wherein the method further includes cutting vessel wall tissue at a second time.

32. The method of example 31, further including repositioning the cutting element between cutting vessel wall tissue the first time and cutting vessel wall tissue the second time.

33. The method of example 32 wherein repositioning the cutting element occurs while a portion of the dissection device remains positioned within the dissection pocket.

34. The method of example 17 wherein the space within the vessel wall is a first space, and wherein the method further includes:
   flexing the arm outwardly away from a longitudinal axis of the shaft at a first time to separate tissue at the periphery of the space;
   collapsing the arm towards the longitudinal axis of the shaft after flexing the arm the first time; and
   after collapsing the arm, flexing the arm outwardly away from a longitudinal axis of the shaft at a second time to separate tissue.

35. The method of example 34, further including repositioning the distal portion before flexing the arm outwardly the second time.

36. The method of example 35 wherein repositioning the distal portion includes at least one of: moving the distal portion axially within the dissection pocket, moving the distal portion laterally within the dissection pocket, and rotating the distal portion about its longitudinal axis within the dissection pocket.

37. The method of example 17, further including separating tissue at the periphery of the space by ejecting a fluid from the distal portion while separating tissue at the periphery of the space with the arm.

38. The method of example 21 wherein cutting vessel wall tissue adjacent the opening with the cutting element and flexing the portion of the arm outwardly away from the longitudinal axis of the shaft to create the dissection pocket within the vessel wall occurs at the same time.

39. The method of example 21 wherein cutting vessel wall tissue adjacent the opening with the cutting element transforms the dissection pocket into a valve leaflet.

40. A device for separating tissue within a wall of a blood vessel, the device comprising:
   an first elongated shaft having a longitudinal axis, a proximal portion, and a distal portion configured to be (1) intravascularly delivered to a treatment site within the blood vessel, (2) advanced through an opening at an interior surface of the blood vessel wall to a space within the wall, and (3) positioned within the space within the wall of the blood vessel at the treatment site;
   a second elongated shaft positioned within the first elongated shaft;
   a dissection arm at the distal portion of the first elongated shaft, the arm having a longitudinal axis and moveable between a low-profile state and a deployed state via axial movement of the second elongated shaft relative to the first elongated shaft, and wherein—
      in the deployed state, a portion of the arm flexes outwardly away from the longitudinal axis of the shaft, and
      the arm is configured to be deployed within the space such that, as the arm moves from the low-profile state to the deployed state, the arm pushes against vessel wall tissue at a periphery of the space, thereby separating tissue at the periphery to form a dissection pocket having a predetermined shape; and
   a cutting device configured to be slidably received within a lumen of the second elongated shaft, the cutting device including a shaft and a cutting element rotatably coupled to the shaft, and wherein, in a deployed state, the cutting element is configured to extend outwardly away from the longitudinal axis of the shaft.

41. The device of any of examples 1-16 and 40 wherein the cutting element has a sharp edge, and wherein, in the deployed state, the sharp edge faces proximally.

42. The device of any of examples 1-16, 40 and 41 wherein the cutting element has a sharp edge, and wherein, in the deployed state, the sharp edge faces distally.

43. The device of any of examples 1-16 and 40-42 wherein the first elongated shaft includes a slot extending along at least a portion of its length, and wherein, when the cutting element is in a deployed state, the cutting element extends through the slot.

44. The device of any of examples 1-16 and 40-43 wherein the slot is a first slot and the second elongated shaft includes a second slot extending along at least a portion of its length, wherein the second elongated shaft is positioned within the first elongated shaft such that the first and second slots are circumferentially aligned, and wherein the cutting element is configured to extend through the first and second in a deployed state.

45. The device of any of examples 1-16 and 40-44 wherein the second elongated shaft includes a slot extending along at least a portion of its length, and wherein the cutting element is configured to extend through the slot in a deployed state.

46. The device of any of examples 1-16 and 40-45 wherein the dissection arm includes a slot extending along at least a portion of its length, and wherein the cutting element is configured to move in a longitudinal direction through the slot in a deployed state.

47. The device of any of examples 1-16 and 40-46 wherein the dissection arm includes a slot extending along at least a portion of its length, and wherein the cutting element is configured to move in a longitudinal direction through the slot when the cutting arm is in a deployed state and when the dissection arm is in a deployed state.

48. The device of any of examples 1-16 and 40-47 wherein the dissection arm includes a slot extending along at least a portion of its length, and wherein the cutting element is configured to move in a longitudinal direction through the slot when the cutting arm is in a deployed state and when the dissection arm is in a deployed state.

49. The device of any of examples 1-16 and 40-48 wherein the dissection arm includes a first segment and a second segment separated by a flexible joint.

50. The device of any of examples 1-16 and 40-49 wherein the dissection arm includes first, second, and third segments, and wherein the first and second segments are separated by a first flexible joint and the second and third segments are separated by a second flexible joint, and wherein the second segment includes a cutting element extending along at least a portion of its length.

51. The device of any of examples 1-16 and 40-50 wherein the dissection arm is a first dissection arm and the device includes a second dissection arm, and wherein the cutting element is configured to extend outwardly away from the shaft within an interior region defined by an outline of the first and second dissection arms in a deployed state.

5.0 CONCLUSION

The dissection devices of the present technology may have multiple advantages over conventional dissection devices, such as balloon-based systems. For example, cutting elements may be more easily integrated with the controlled dissection device because the general strength and rigidity of the dissection arms enable the cutting elements to be fixed to the arms via a variety of robust fixation methods (e.g., via welding, soldering, adhesive, mechanical fixation, etc.) and/or guided by the arms, for example, with slots or other coupling features. Conversely, cutting elements are generally limited to being affixed to the surface of conventional balloons using an adhesive because of the elasticity of balloons. Moreover, because the dissection arms are more rigid than balloons, the arms maintain their shape during deployment such that the surface along which the cutting elements are affixed does not bend or stretch during deployment. In contrast, the surface of a balloon stretches and changes shape during inflation, which can affect the shape of the cutting elements.

Another advantage of the controlled dissection devices of the present technology is that they provide precise control over the shape of the dissection pocket during dissection, as well as greater predictability of the resulting shape of the dissection pocket. Balloon-based dissection devices expand in the direction of least resistance; thus, there is very little control over the amount of tension applied at each point during the dissection. As a result, a balloon may over-stretch a thin flap (in the direction of the vessel lumen) prior to or instead of performing any lateral dissection. Such stretching can result in an unpredictable dissection pocket shape, leaflet tearing, and/or insufficient dissection. Conversely, the controlled dissection devices described with above reference to FIGS. 2A-34B are generally more rigid (e.g., non-elastic under operating forces) than balloons and expand to a substantially pre-defined shape or otherwise controlled configuration even in the presence of large and/or unpredictable tissue forces.

Yet another advantage of the controlled dissection devices of the present technology is that they enable complex dissection techniques. For example, the controlled dissection devices of the present technology can generate non-symmetric dissection pockets (i.e., non-symmetric if viewing the device end-on, about a latitudinal midline of the device). The lengths, angles, shapes, etc. of the dissection arms of the present technology can be configured to achieve a desired shape regardless of tissue forces present at the treatment site. Another complex dissection technique of the present technology is the independent control of the tensioning and dissection arms. The tensioning arms can expand along one or more particular planes, and the dissection arms can expand along one or more distinct planes as detailed above.

The controlled dissection devices configured in accordance with the present technology also provide high resolution and clarity of visualization during expansion under ultrasound as compared to an expandable balloon-based system. For example, the metallic surfaces of the dissection arms can include strands of polyvinyl alcohol ("PVA") or other material viewable under ultrasound, and therefore the expansion can be monitored clearly. Various locations on and/or components of the controlled dissection devices (e.g., the dissection elements, the tensioning elements, the blades, etc.) can include such a viewable material that provides real-time monitoring of the shape of the dissection pocket during the procedure. In contrast, the surface of a urethane balloon, PET balloon, and/or latex balloon can be difficult to perceive under ultrasound, and thus it can be difficult to differentiate the balloon from thin layers of tissue surrounding the balloon.

Any of the dissection devices and/or components thereof (e.g., shaft, cutting elements, dissection arms, tensioning arms, pull rod, etc.) described herein, can be made from stainless steel, Nitinol, PEEK and other generally suitable materials with sufficient stiffness and bending characteristics (e.g., elastic or super elastic) that can impart the desired forces. For example, any of the dissection arms and/or tensioning arms described herein can be made of a super-elastic and/or shape memory material and can be heat-set during manufacturing to be biased in a particular shape and/or bend direction that corresponds to a desired dissection pocket DP and/or leaflet L shape. Alternately, the bias may be created by pre-bending the components to the desired bend direction to impart some memory to the components.

In all of the above embodiments involving dissection and/or tension arms, the flexibility of the arms may be tailored to achieve a desired geometry and force on the tissue. For example the dissection or tensioning arms may vary in width. Alternately, the dissection or tensioning arms may have a cut out pattern that increases the flexibility of the arms in a bend direction while maintaining rigidity in a non-bend direction. For example the dissection arms may be wide but have a series of square holes to create a ladder pattern. This pattern allows the arms to bend more easily while resisting twisting and thus able to deliver more force in the plane of dissection.

In all of the above embodiments, the dissection device may also be configured to hydrodissect vessel wall tissue simultaneously with mechanical dissection. In a particular embodiment, the dissection device can include a hydrodissection device, such as a needle or tube fluidly coupled to a pressurized fluid source, such as a syringe, pressurized fluid bag, or pump. The tip of the needle can be configured to deliver a focused fluid flow through a nozzle, to create a hydrodissection force. In another embodiment, one or more shafts of the dissection device can be fluidly coupled to a pressurized fluid source and may include one or more fluid delivery ports at its distal portion.

In all embodiments, the dissection device is configured to fit through an opening in a vessel wall access, as well as a delivery device and/or system (for delivery through the vasculature and/or to gain access to an interior portion of the vessel wall) having an outer diameter which is less than or equal to 20 F, or less than or equal to 19 F, or less than or equal to 16 F, or less than or equal to 14 F (corresponding to outer diameters of 0.260 inches, 0.234 inches, 0.209 inches or 0.192 inches, respectively). This size range is appropriate for treatment of veins through a femoral venous or internal jugular access site, or for treatment of arteries through a femoral arterial or carotid artery access site, with the smaller sizes providing more options for access vessel size and access/closure methods. In some embodiments, the dissection device may have an outer diameter that is less than or equal to 0.150 inches, or less than or equal to 0.124 inches, or less than or equal to 0.099 inches, or less than or equal to 0.072 inches (for use with, for example, a delivery device and/or system having an outer diameter of 20 F, 19 F, 16 F, or 14 F, respectively). In these and other embodiments, the delivery device and/or system also includes a lumen for an intravascular imaging device, such as a 3.2 F intravascular ultrasound catheter with an imaging lumen of 0.060 inches inner diameter. In this embodiment, the lumen of the delivery device and/or system may be reduced to accommodate the imaging device lumen and associated wall dimensions. In such embodiments, for example, the dissection device may have an outer diameter that is less than or equal to 0.096 inches, or less than or equal to 0.060 inches, or less than or equal to 0.034 inches (for use with, for example, a delivery device and/or system having an outer diameter that is 20 F, 19 F, or 16 F, respectively).

Although many of the embodiments are described above with respect to devices, systems, and methods for intravascular creation of autologous venous valves and/or valve leaflets, other applications and other embodiments in addition to those described herein are within the scope of the technology. For example, the devices, systems, and methods of the present technology can be used in any body cavity or lumen or walls thereof (e.g., arterial blood vessels, venous blood vessels, urological lumens, gastrointestinal lumens, etc.) and used for surgical creation of autologous valves as well as repair of autologous and/or synthetic valves. Additionally, several other embodiments of the technology can have different states, components, or procedures than those described herein. For example, although several embodiments of the present technology include two dissection arms, in other embodiments the dissection device can have more or fewer than two dissection arms (e.g., one dissection arm, three dissection arms, four dissection arms, etc.) For example, in some embodiments, the dissection device can include a single dissection member having a first portion configured to extend laterally away from the longitudinal axis of the shaft in a first direction and a second portion configured to extend laterally away from the longitudinal axis of the shaft in a second direction opposite the first direction. Moreover, it will be appreciated that specific elements, substructures, advantages, uses, and/or other features of the embodiments described with reference to FIGS. 2A-34B can be suitably interchanged, substituted or otherwise configured with one another in accordance with additional embodiments of the present technology. For example, the tensioning arms described with reference to FIGS. 21A-26 can be combined with any of the dissection devices shown in FIGS. 2A-20 and 27A-34B. Likewise, the cutting elements described in FIGS. 3A-3D, 10-22 and 24A-26 can be combined with any of the dissection arms, tensioning arms, and/or dissection devices described herein.

Furthermore, suitable elements of the embodiments described with reference to FIGS. 2A-34B can be used as standalone and/or self-contained devices. A person of ordinary skill in the art, therefore, will accordingly understand that the technology can have other embodiments with additional elements, or the technology can have other embodiments without several of the features shown and described below with reference to FIGS. 2A-34B. For example, the dissection devices, systems, and methods of the present technology can be used with any of the device devices, systems, and methods disclosed in U.S. patent application Ser. No. 13/035,752, filed Feb. 2, 2011, U.S. patent application Ser. No. 13/926,996, filed Jun. 25, 2013, U.S. patent application Ser. No. 13/035,919, filed Feb. 25, 2011, U.S. patent application Ser. No. 13/450,432, filed Apr. 19, 2012, U.S. patent application Ser. No. 14/377,492, filed Aug. 7, 2014, PCT Application No. PCT/US2014/011209, filed Jan. 10, 2014, U.S. patent application Ser. No. 14/499,969, filed Sep. 26, 2014, U.S. Provisional Patent Application No. 61/969,262, filed Mar. 24, 2013, and U.S. Provisional Patent Application No. 61/969,263, filed Mar. 24, 2013, all of which are incorporated by reference herein their entireties.

We claim:

1. A device for separating tissue within a wall of a blood vessel, the device comprising:
   an elongated shaft having a longitudinal axis, a proximal portion and a distal portion, wherein—
      the distal portion is configured to be (1) intravascularly delivered to a treatment site within the blood vessel, (2) advanced through an opening at an interior surface of the blood vessel wall to a space within the wall, and (3) positioned within the space within the wall of the blood vessel at the treatment site, and
      the distal portion has a diameter of at most 0.150 inch for gaining access into the space within the wall;
   an elongated member slidably positioned within the elongated shaft, wherein the elongated member includes a lumen configured to be advanced over a needle to deliver the distal portion into the space within the wall of the blood vessel;
   a dissection arm at the distal portion of the elongated shaft, the dissection arm having a longitudinal axis and moveable between a low-profile state and a deployed state via axial movement of the elongated member relative to the elongated shaft, the dissection arm including a cutting element, wherein—
      in the low-profile state, the longitudinal axis of the dissection arm is parallel to the longitudinal axis of the elongated shaft,
      in the deployed state, a portion of the dissection arm flexes outwardly away from the longitudinal axis of the elongated shaft such that the cutting element faces in a proximal direction to cut vessel wall tissue adjacent the opening to widen the opening, and
      the dissection arm is configured to be deployed within the space such that, as the arm moves from the low-profile state to the deployed state, the dissection arm pushes against vessel wall tissue at a periphery of the space, thereby separating tissue at the periphery to form a dissection pocket having a predetermined shape; and a tensioning arm at the distal portion of the elongated shaft, the tensioning arm having a low-profile state and a deployed state, wherein—
in the deployed state, the tensioning arm flexes outwardly away from the longitudinal axis of the elongated shaft to create tension in the dissection pocket generally transverse to a plane of dissection, and
at least a portion of the dissection arm and at least a portion of the tensioning arm extend along a longitudinal segment of the distal portion.

2. The device of claim 1 wherein the dissection arm is configured to flex outwardly within a first plane, and wherein, in the deployed state, the tensioning arm flexes outwardly away from the longitudinal axis of the elongated shaft within a second plane that is angled relative to the first plane.

3. The device of claim 1 wherein the dissection arm is a first arm and wherein the device further includes a second arm at the distal portion, wherein an outline of the first and second arms in the deployed state defines the predetermined shape of the dissection pocket.

4. The device of claim 1 wherein the dissection arm is integral with the elongated shaft.

5. The device of claim 1 wherein a distal end portion of the elongated member is coupled to a distal end portion of the elongated shaft.

6. The device of claim 1 wherein the dissection arm includes a first segment and a second segment separated by a flexible joint.

7. The device of claim 6 wherein the cutting element extends along at least a portion of the second segment.

8. The device of claim 1 wherein the dissection arm includes first, second, and third segments, and wherein the first and second segments are separated by a first flexible joint and the second and third segments are separated by a second flexible joint, and wherein the third segment includes a cutting element extending along at least a portion of its length.

9. The device of claim 1 wherein the distal portion of the elongated shaft has a maximum diameter of 0.072 inch.

10. The device of claim 1 wherein the needle is a hydrodissection needle fluidically coupled to a pressurized fluid source and configured to deliver a focused fluid flow through a nozzle to create a hydrodissection force.

11. A device for separating tissue within a wall of a blood vessel, the device comprising:
a first elongated shaft having a longitudinal axis, a proximal portion and a distal portion, wherein the distal portion is configured to be (1) intravascularly delivered to a treatment site within the blood vessel, (2) advanced through an opening at an interior surface of the blood vessel wall to a space within the wall, and (3) positioned within the space within the wall of the blood vessel at the treatment site, wherein the distal portion has a diameter of at most 0.150 inch for gaining access into the space within the wall;

a second elongated shaft positioned within the first elongated shaft, wherein the second elongated shaft includes a lumen configured to extend over a needle for delivery of the distal portion of the first elongated shaft into the space within the wall of the blood vessel created by the needle;

a dissection arm at the distal portion of the first elongated shaft, the dissection arm having a longitudinal axis and moveable between a low-profile state and a deployed state via axial movement of the second elongated shaft relative to the first elongated shaft, and wherein—
in the deployed state, a portion of the dissection arm flexes outwardly away from the longitudinal axis of the first elongated shaft, and
the dissection arm is configured to be deployed within the space such that, as the dissection arm moves from the low-profile state to the deployed state, the dissection arm pushes against vessel wall tissue at a periphery of the space, thereby separating tissue at the periphery to form a dissection pocket having a predetermined shape; and a cutting element positioned along at least a portion of the dissection arm and configured to cut the vessel wall tissue adjacent the opening to widen the opening.

12. The device of claim 11 wherein the cutting element has a sharp edge, and wherein, in the deployed state, the sharp edge faces proximally.

13. The device of claim 11 wherein the cutting element has a sharp edge, and wherein, in the deployed state, the sharp edge faces distally.

14. The device of claim 11 wherein the dissection arm is a first dissection arm, the cutting element is a first cutting element, and the device includes a second dissection arm and a second cutting element, and wherein the second cutting element is positioned along at least a portion of the second dissection arm.

15. The device of claim 11 wherein the distal portion of the first elongated shaft has a maximum diameter of 0.99 inch.

16. The device of claim 11 wherein the first elongated shaft is sized to fit within a 16F delivery catheter.

17. The device of claim 11, further comprising a tensioning arm coupled to the distal portion of the first elongated, the tensioning arm having a low-profile state and a deployed state in which the tensioning arm flexes outwardly away from the longitudinal axis of the shaft, wherein at least a portion of the dissection arm and at least a portion of the tensioning arm extend along the same longitudinal segment of the distal portion.

18. The device of claim 11 wherein the needle is a hydrodissection needle fluidically coupled to a pressurized fluid source and configured to deliver a focused fluid flow through a nozzle to create a hydrodissection force.

* * * * *

UNITED STATES PATENT AND TRADEMARK OFFICE
CERTIFICATE OF CORRECTION

PATENT NO. : 10,603,018 B2
APPLICATION NO. : 14/972006
DATED : March 31, 2020
INVENTOR(S) : Fletcher T. Wilson et al.

It is certified that error appears in the above-identified patent and that said Letters Patent is hereby corrected as shown below:

In the Specification

In Column 3, Line 37, delete "respectively," and insert -- respectively. --.
In Column 12, Line 11, delete "DP)" and insert -- DP --.
In Column 22, Line 35, delete "1601 a-c)" and insert -- 1601a-c) --.
In Column 25, Line 44, delete "forces)." and insert -- forces. --.
In Column 31, Line 55, delete "shaft." and insert -- shaft, --.

Signed and Sealed this
Twentieth Day of September, 2022

Katherine Kelly Vidal
*Director of the United States Patent and Trademark Office*